US008758826B2

(12) United States Patent
Bevier

(10) Patent No.: US 8,758,826 B2
(45) Date of Patent: Jun. 24, 2014

(54) CANNABINOID RECEPTOR BINDING AGENTS, COMPOSITIONS, AND METHODS

(75) Inventor: Jonathan Austin Bevier, Graton, CA (US)

(73) Assignee: Wet Inc., Graton, CA (US)

( * ) Notice: Subject to any disclaimer, the term of this patent is extended or adjusted under 35 U.S.C. 154(b) by 0 days.

(21) Appl. No.: 13/541,400

(22) Filed: Jul. 3, 2012

(65) Prior Publication Data

US 2013/0011484 A1 Jan. 10, 2013

Related U.S. Application Data

(60) Provisional application No. 61/504,655, filed on Jul. 5, 2011.

(51) Int. Cl.

| | |
|---|---|
| *A61K 9/00* | (2006.01) |
| *A61K 9/14* | (2006.01) |
| *A61K 31/05* | (2006.01) |
| *A61K 31/352* | (2006.01) |
| *A61K 31/343* | (2006.01) |
| *A61P 17/00* | (2006.01) |
| *A61K 31/353* | (2006.01) |
| *A61K 9/70* | (2006.01) |
| *A61K 9/51* | (2006.01) |
| *A61K 47/10* | (2006.01) |
| *A61K 47/48* | (2006.01) |

(52) U.S. Cl.

CPC ............ *A61K 31/352* (2013.01); *A61K 31/353* (2013.01); *A61K 31/05* (2013.01); *A61K 9/7015* (2013.01); *A61K 9/7061* (2013.01); *A61K 9/5153* (2013.01); *A61K 47/10* (2013.01); *A61K 47/48861* (2013.01); *A61K 47/48884* (2013.01); *A61K 47/48923* (2013.01)

USPC ........... 424/491; 424/489; 424/490; 424/400; 428/402; 514/733; 514/456; 514/454; 514/468

(58) Field of Classification Search
None
See application file for complete search history.

(56) References Cited

U.S. PATENT DOCUMENTS

| | | | | |
|---|---|---|---|---|
| 6,328,992 | B1 * | 12/2001 | Brooke et al. | 424/449 |
| 6,706,281 | B2 * | 3/2004 | Oshlack et al. | 424/457 |
| 2003/0049320 | A1 * | 3/2003 | Bhagwatwar et al. | 424/486 |
| 2003/0223938 | A1 | 12/2003 | Nagy et al. | |
| 2007/0072939 | A1 | 3/2007 | Kupper | |

OTHER PUBLICATIONS

Vervaet et al., Production of pellets via extrusion-spheronization without the incorporation of microcrystalline cellulose: a critcal review, Eur. J. Pharm Biopharm., 2009, pp. 38-46.*
Tam et al., Chemistry and applications of nanocrystalline cellulose and its derivatives: a nanotechnology prespective, the Canadian J. Chem. Engeering, 2011, vol. 89, pp. 1191-1206, article published online on Jun. 6, 2011.*
Hoag Eds. Pharmaceutical Dosage Forms, Tablets vol. 2 Rational Design and Formulation, Chapter 17, Informa Healthcare, New York, 2008, pp. 510-512.*
Beck Eds. Nanocosmetics and Nanomedicines, new Approaches for skin care, Chapter 1, Springer, Berlin, 2011, p. 12.*
C.C. Berry et al., Dextran and Albumin Derivatised Iron Oxide Nanoparticles: Influence on Fibroblasts in Vitro, Biomaterials, Mar. 30, 2003, vol. 24, Elsevier Ltd., United Kingdom.

* cited by examiner

*Primary Examiner* — Kevin S Orwig
*Assistant Examiner* — Ping Cao
(74) *Attorney, Agent, or Firm* — Cislo & Thomas, LLP

(57) ABSTRACT

A composition comprising a cannabinoid receptor binding agent attached to a particle for the treatment of skin conditions. The particle may be a nanoparticle, such as nanocrystalline cellulose. The particle may further be modified with functional moieties. Drug delivery properties may be modified by coating the particles or using vesicles to deliver the cannabinoid receptor binding agent and particle. A substrate may be used to deliver the composition to the skin.

17 Claims, 47 Drawing Sheets

| NAME | STRUCTURAL FORMULA |
|---|---|
| $\Delta^9$-Tetrahydrocannabinol $\Delta^9$-THC-C5 |  |
| (−)-$\Delta^8$-*trans*-(6a$R$,10a$R$)-$\Delta^8$-Tetrahydrocannabinol $\Delta^8$-THC-C5 |  |

| NAME | STRUCTURAL FORMULA |
|---|---|
| Δ⁹-Tetrahydro-cannabinolic acid A<br>Δ⁹-THCA-C₅ A | |
| Δ⁹-Tetrahydro-cannabinolic acid B<br>Δ⁹-THCA-C₅ B | |

FIGURE 4B

| NAME | STRUCTURAL FORMULA |
|---|---|
| Cannabidiol | |
| Cannabidiolic Acid | |

FIGURE 4C

| NAME | STRUCTURAL FORMULA |
|---|---|
| Cannabinol |  |
| Cannabinolic Acid |  |

| NAME | STRUCTURAL FORMULA |
|---|---|
| Cannabigerol | |
| Cannabigerolic acid | |

FIGURE 4E

| NAME | STRUCTURAL FORMULA |
|---|---|
| Cannabielsoic Acid A |  |
| Cannabielsoic Acid B |  |

| NAME | STRUCTURAL FORMULA |
|---|---|
| Cannabichromene | |
| Cannabichromenic Acid | |

FIGURE 4G

| NAME | STRUCTURAL FORMULA |
|---|---|
| Cannabicyclol | |
| $\Delta^9$-Tetrahydrocannabivarin $\Delta^9$-THCV-C$_3$ | |

FIGURE 4H

| NAME | STRUCTURAL FORMULA |
|---|---|
| Cannabivarol |  |
| Cannabidivarol |  |

CANNABINOID RECEPTOR BINDING AGENTS, COMPOSITIONS, AND METHODS

CROSS-REFERENCE TO RELATED APPLICATION

This patent application claims the benefit of U.S. Provisional Patent Application Ser. No. 61/504,655, entitled "Cannabinoid Receptor Binding Agents, Compositions, and Methods," filed Jul. 5, 2011, which application is incorporated in its entirety here by this reference.

TECHNICAL FIELD

The present invention relates generally to compositions and methods for administration of cannabinoid receptor binding agents. In particular aspects, the present invention relates to compositions and methods for topical delivery of cannabinoid receptor binding agents, and related therapeutic uses, methods of manufacture, kits, diagnostics and other products and processes.

BACKGROUND

The cannabinoid system has been the subject of much and ongoing study. While not completely characterized, the mammalian system involves at least two cannabinoid receptors, cannabinoid receptors 1 and 2 ("CB1" and "CB2"). See, review, Oesch, S, and J. Gertsch, "Cannabinoid receptor ligands as potential anticancer agents—high hopes for new therapies?" Journal of Pharmacy and Pharmacology 61: 839-853 (2009). Cannabinoid receptors have been found throughout the dermis and organ surface cells, see, review, Kupczyk, P. et al, "Cannabinoid system in the skin—a possible target for future therapies in dermatology," Experimental Dermatology 18: 669-679 (2009).

SUMMARY

Disclosed are compositions and methods for administration of a cannabinoid receptor binding agent, and in particular aspects, for local administration. Such administration may include compositions and methods for topical administration, including transdermal and mucosal delivery of cannabinoid receptor binding agent. Particular aspects include local administration of a cannabinoid receptor binding agent with a particle, and in particular embodiments, a cannabinoid receptor binding agent attached to a nanoparticle. Compositions, methods, and related aspects are further described herein.

BRIEF DESCRIPTION OF DRAWINGS

FIGS. 4A-I presents graphical illustrations of the chemical structure of particular *cannabis*-related compositions.

DETAILED DESCRIPTION OF THE INVENTION

Definitions and Related Matters

Figure 1:
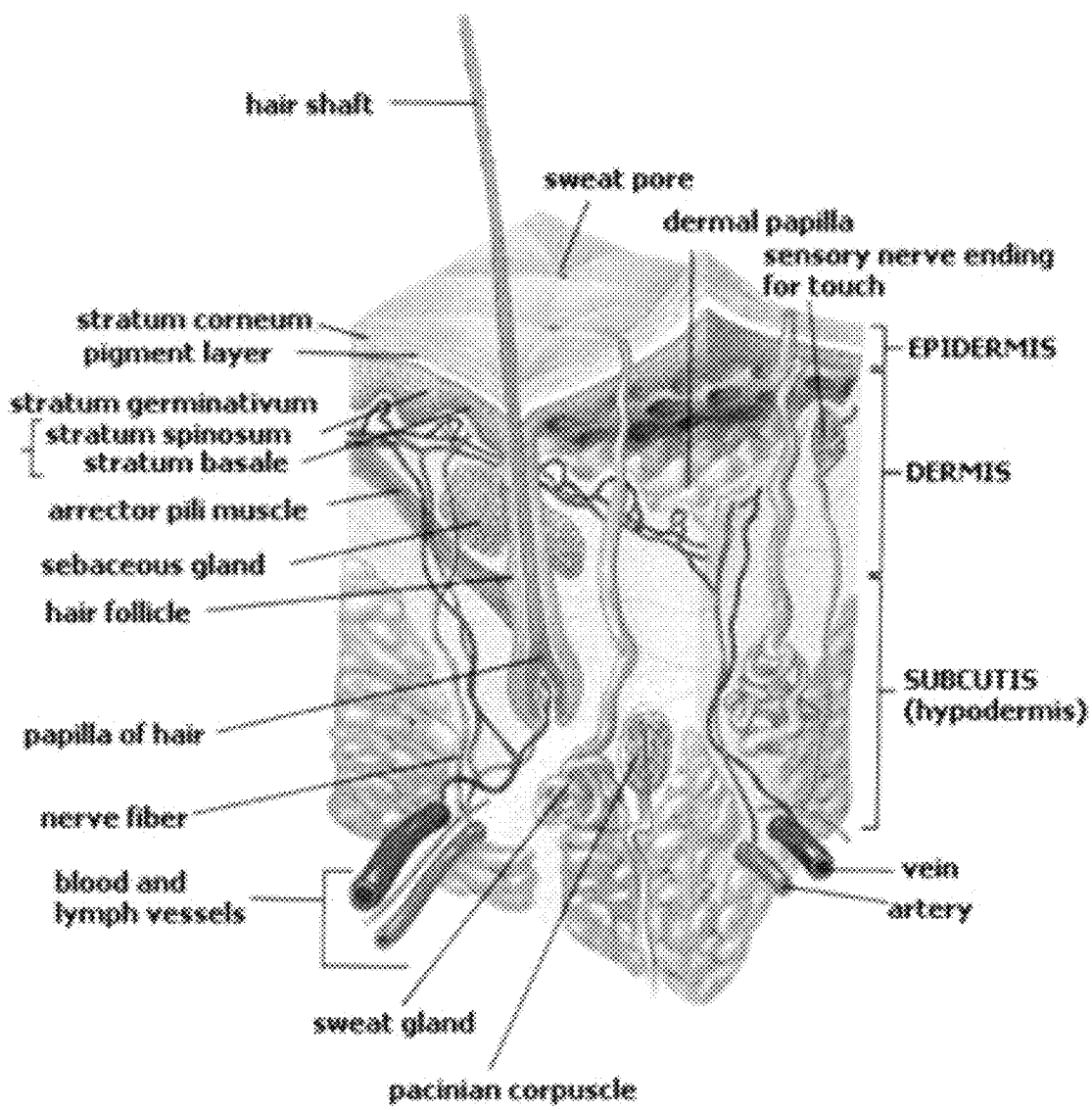
FIG. 1 is a graphic depiction of the structure of mammalian, and particularly human, skin, adapted from the National Cancer Institute, http://training.seer.cancer.gov/melanoma/anatomy/.
Figure 2:
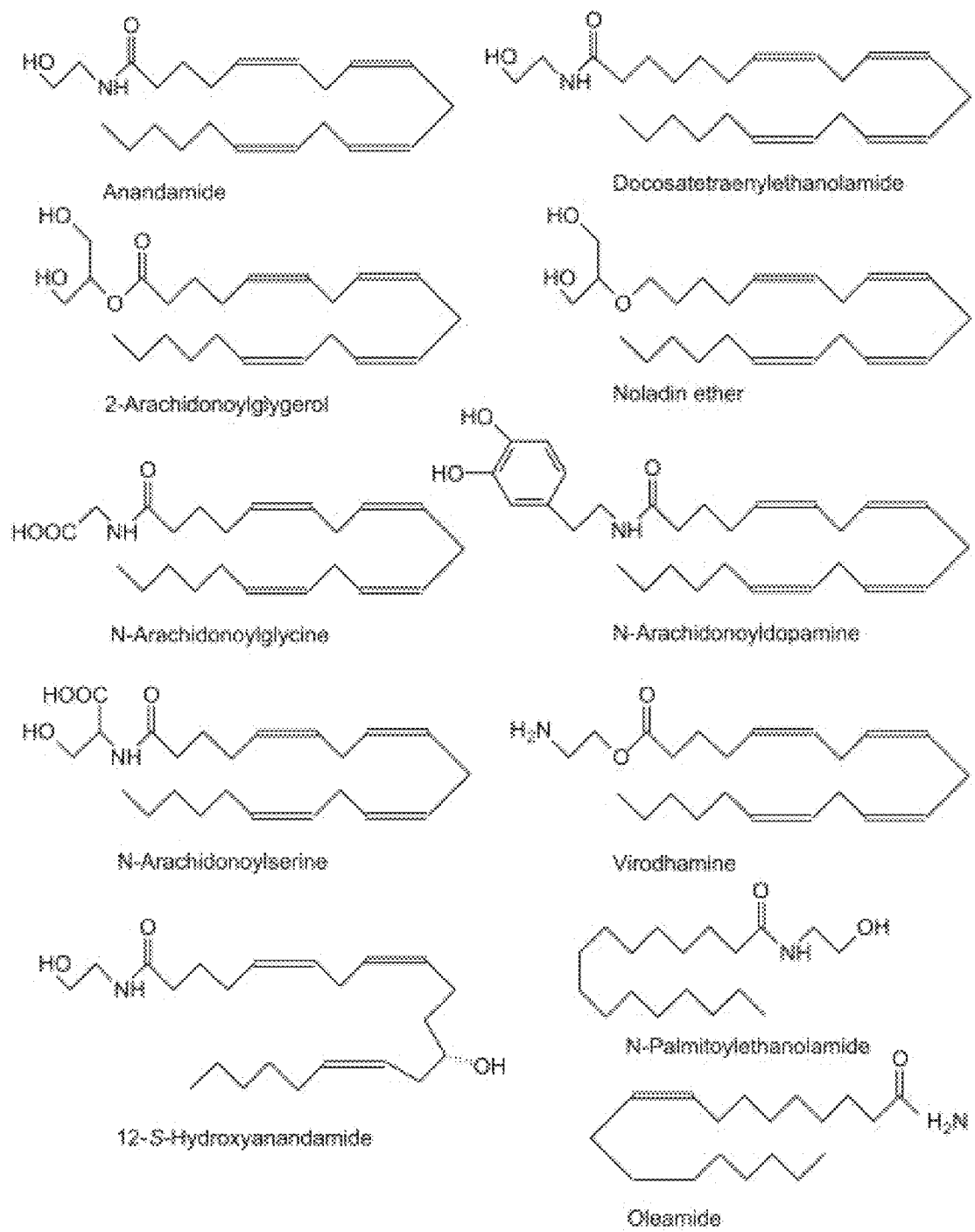
FIG. 2 is a graphic depiction of major endocannabinoids identified from: Hiley, R.C., "Endocannabinoids and the Heart," Journal of Cardiovascular Pharmacology, Author manuscript; available in PMC 2009 October 1, published in final edited form as: Journal of Cardiovascular Pharmacology 53: 267-275 (2009).
Figure 3A:
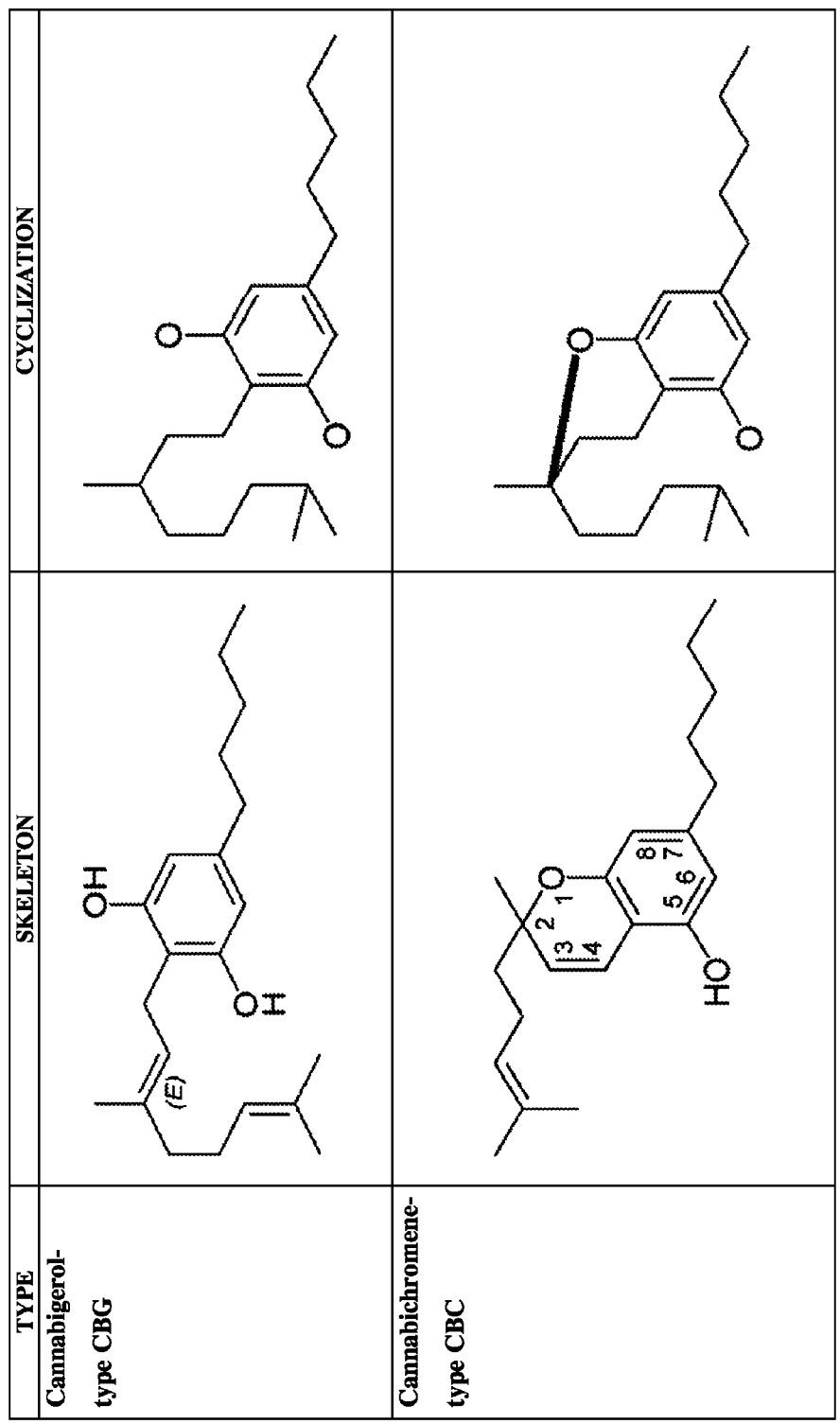
FIGS. 3A-D is a table containing graphic depictions of the main classes of natural cannabinoids.
Figure 3B:
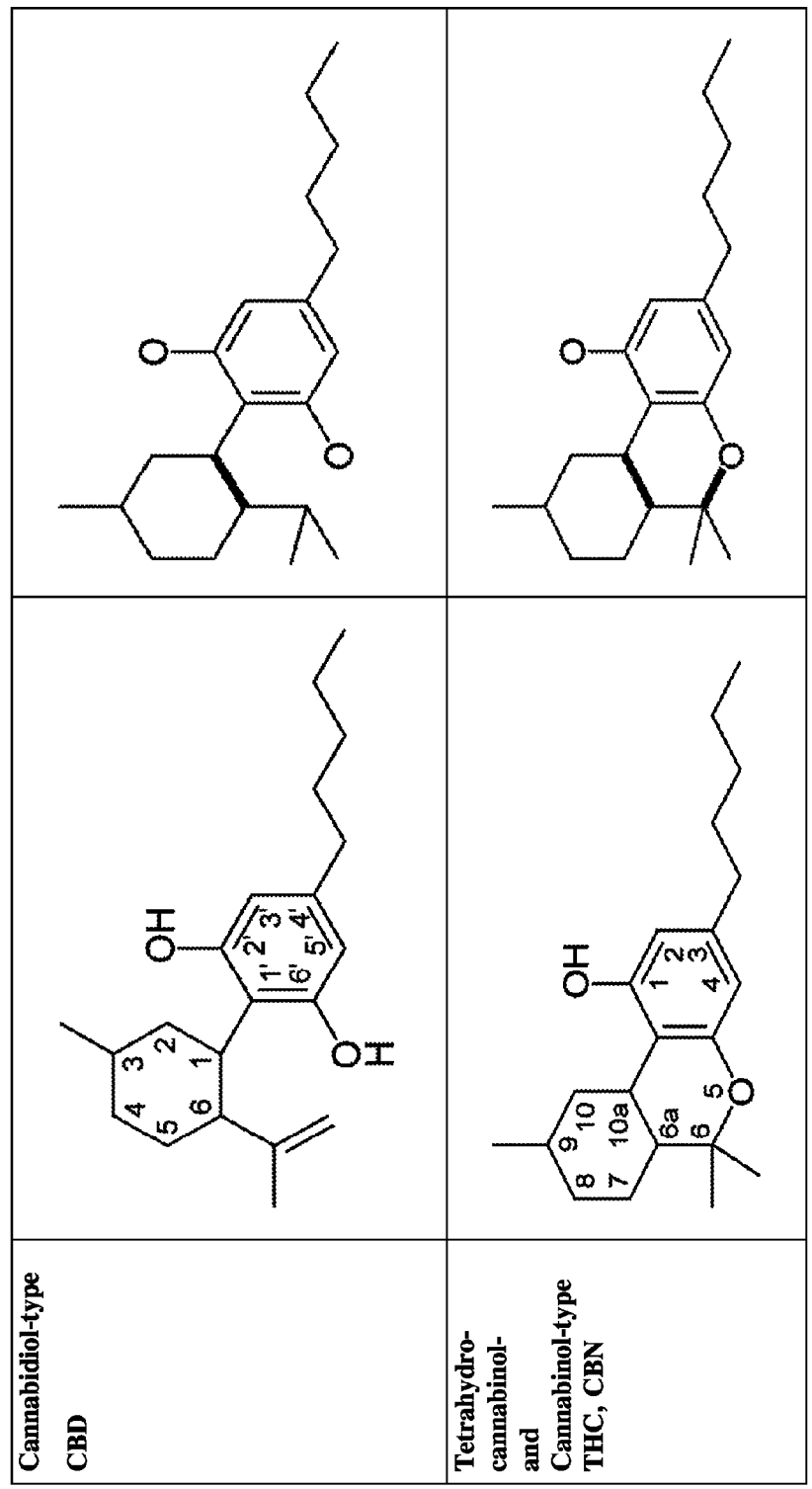
Figure 3C:
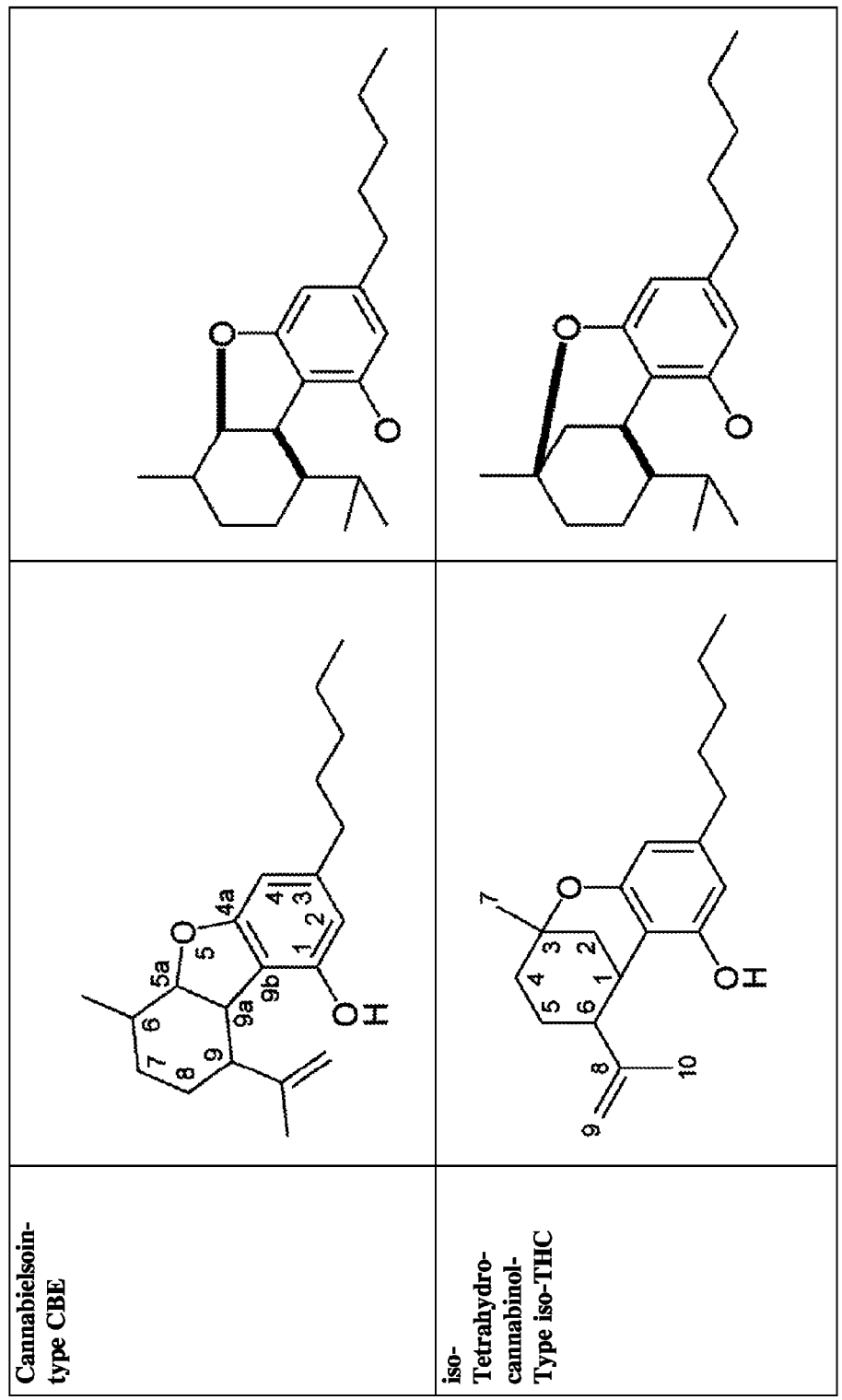
Figure 3D:
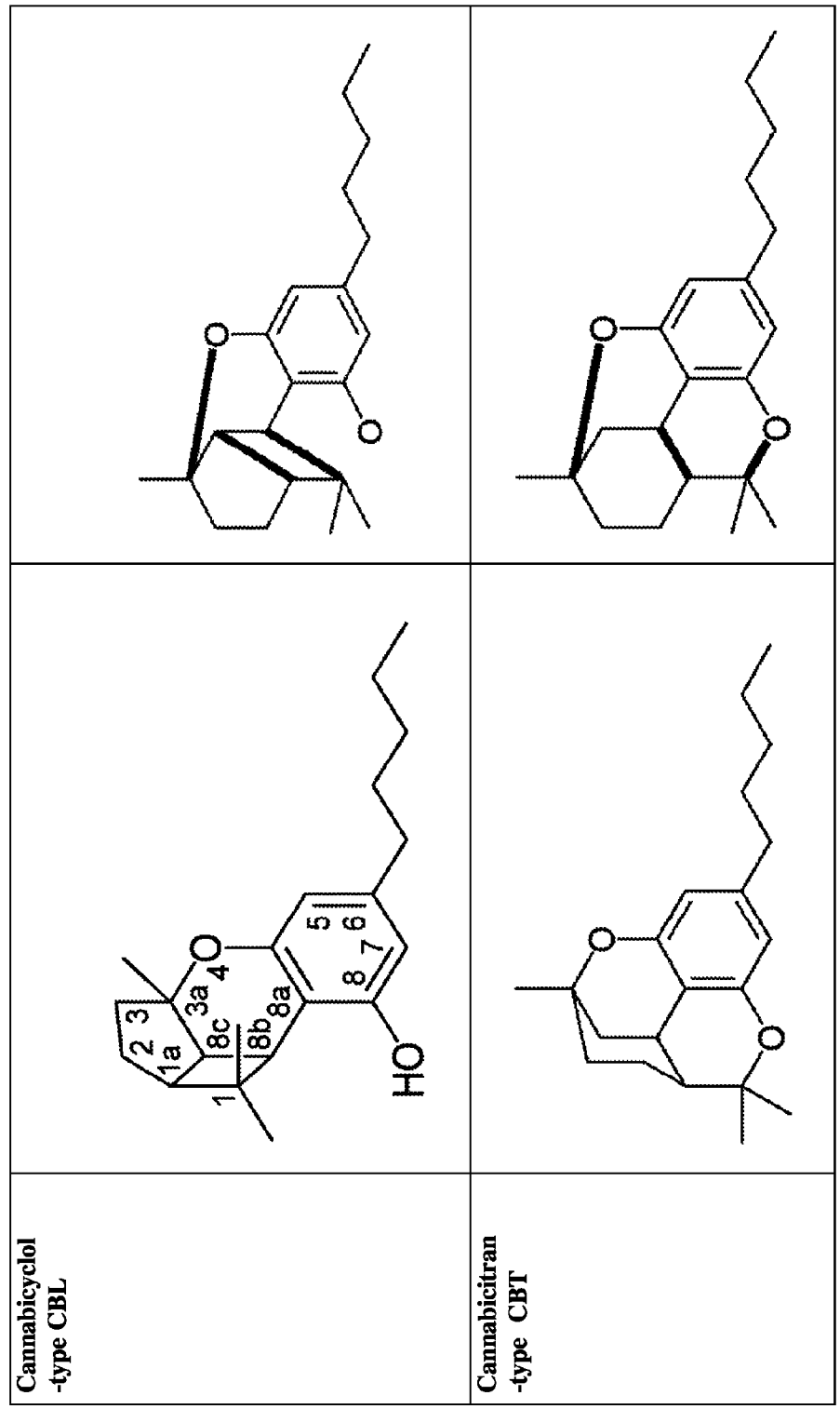
Figure 4A:
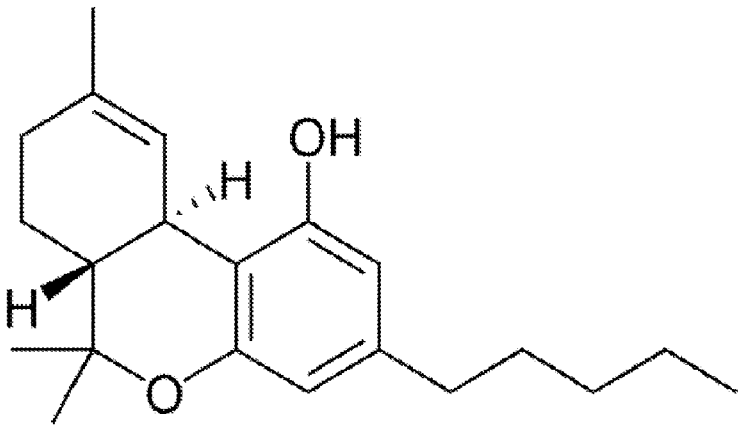
Figure 4A:
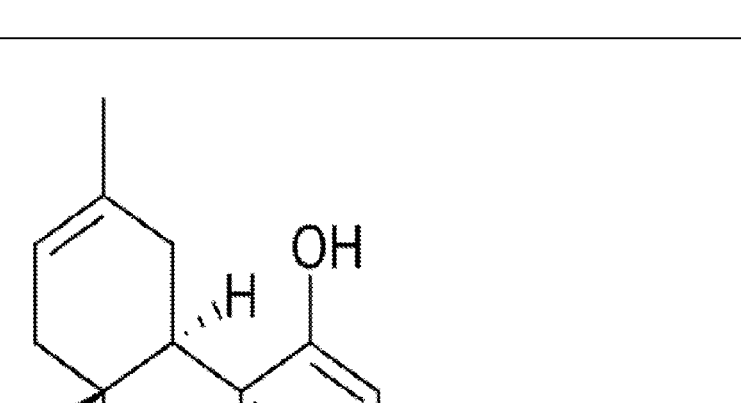
Figure 4D:
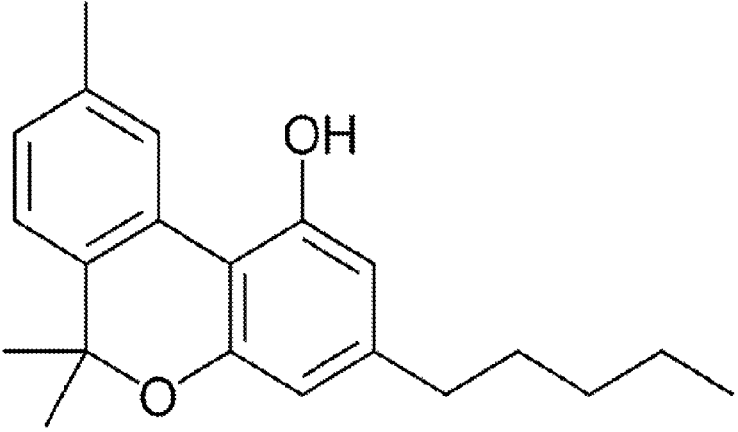
Figure 4D:
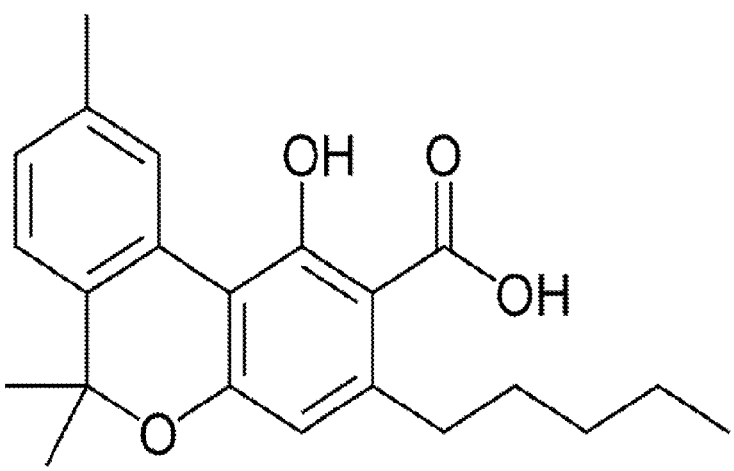
Figure 4F:
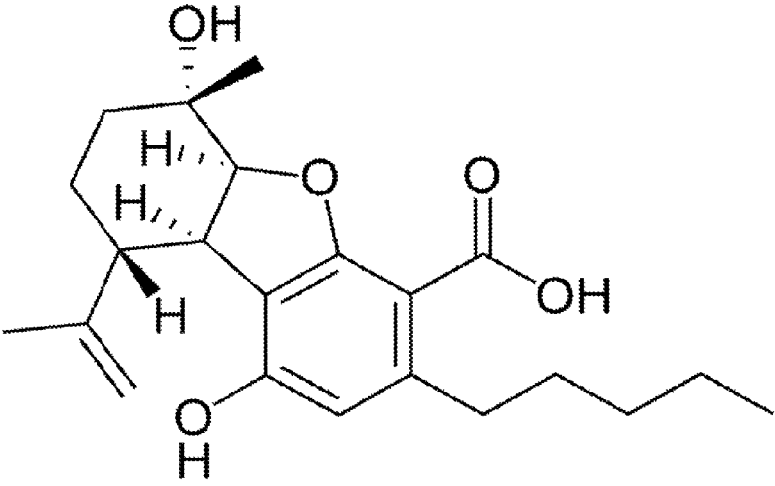
Figure 4F:
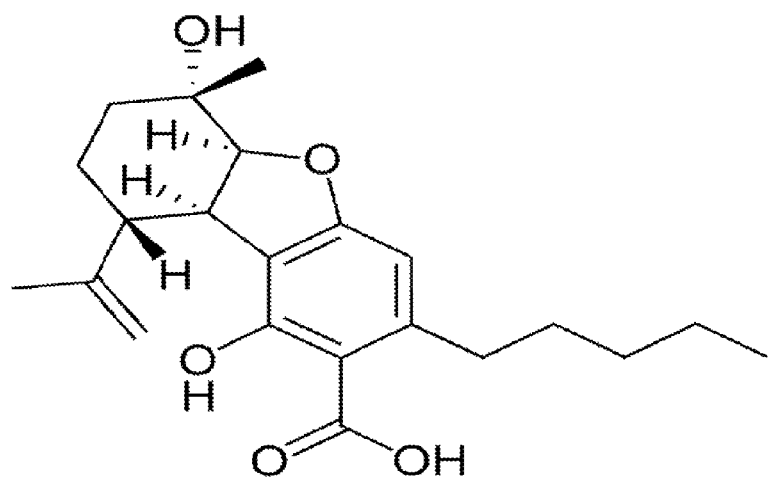
Figure 4I:
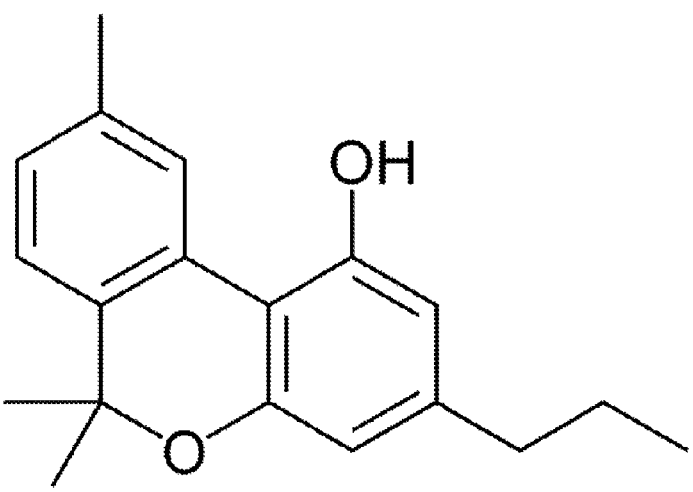
Figure 4I:
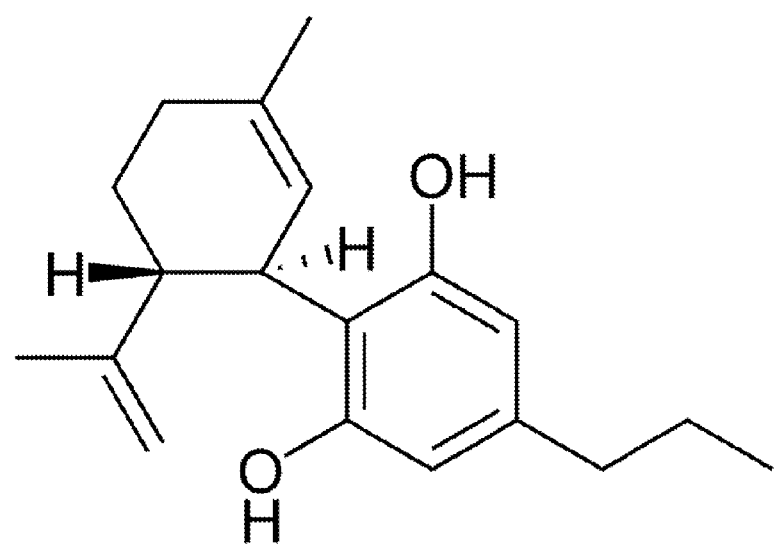
Figure 5A:
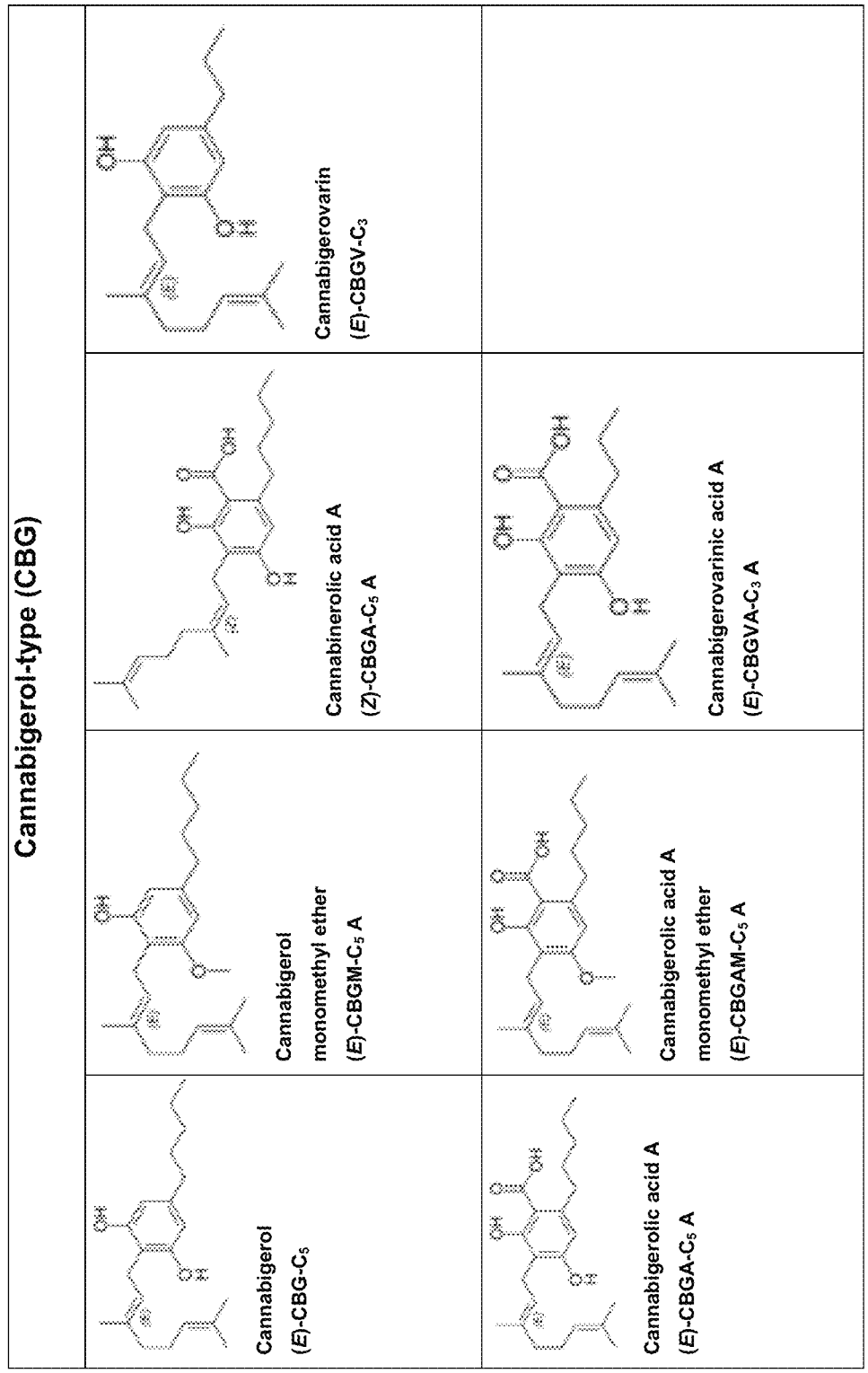
FIGS. 5A-K contain tables showing graphical illustrations of particular cannabinoid receptor binding agents.
Figure 5B:
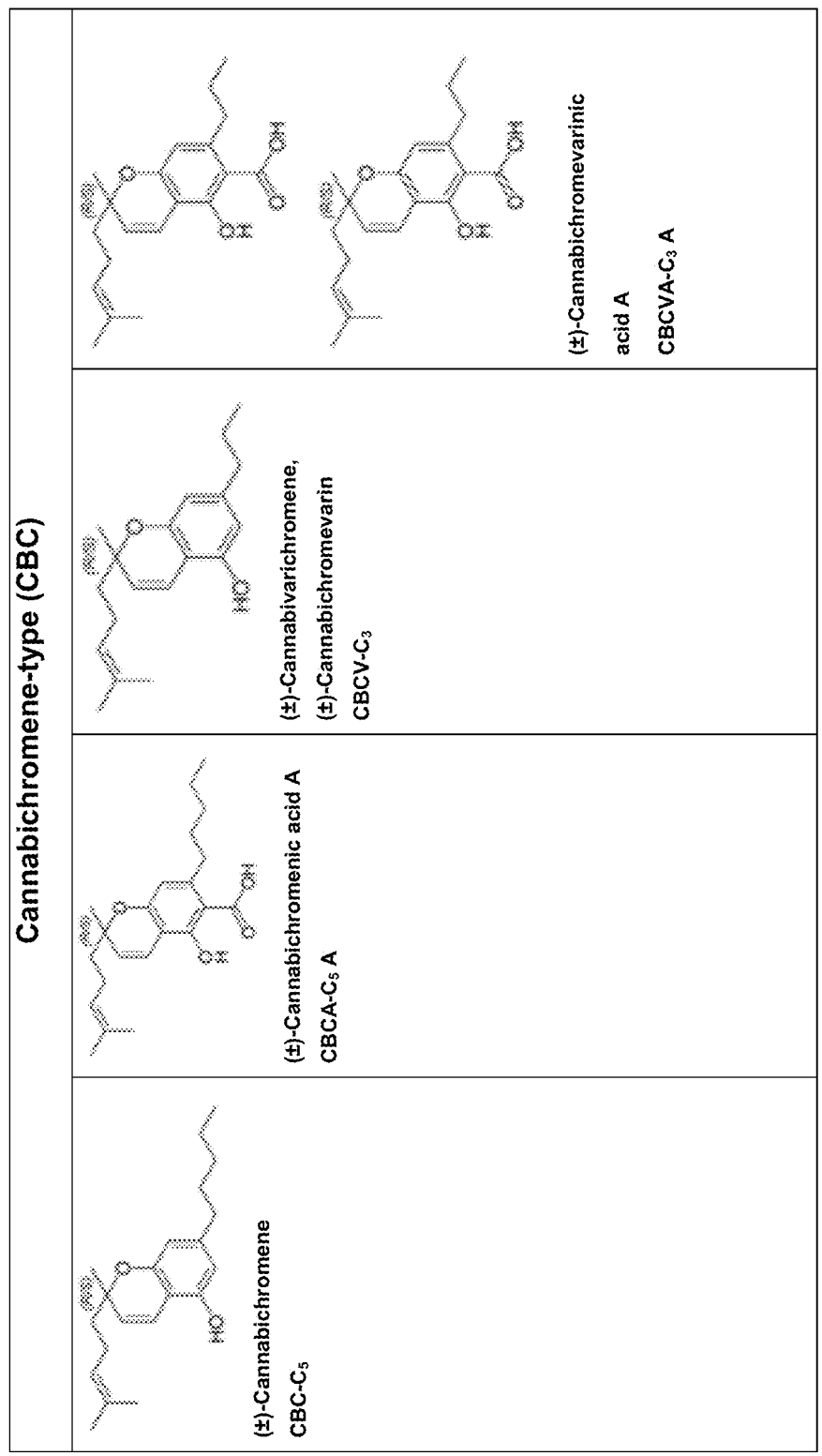
Figure 5C:
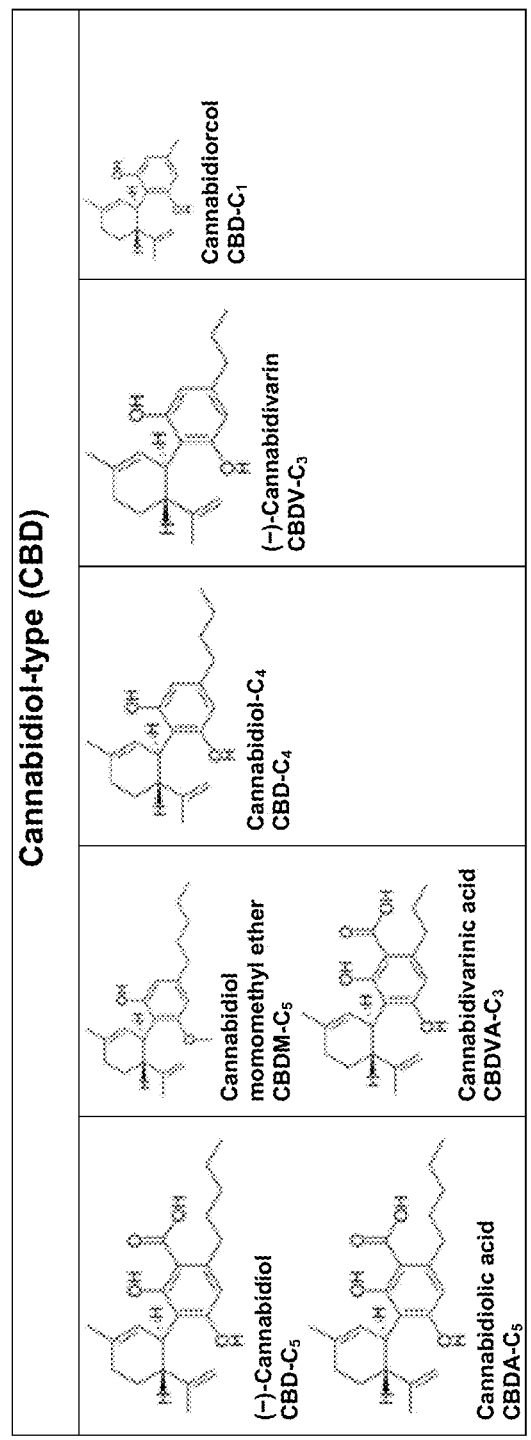
Figure 5D:
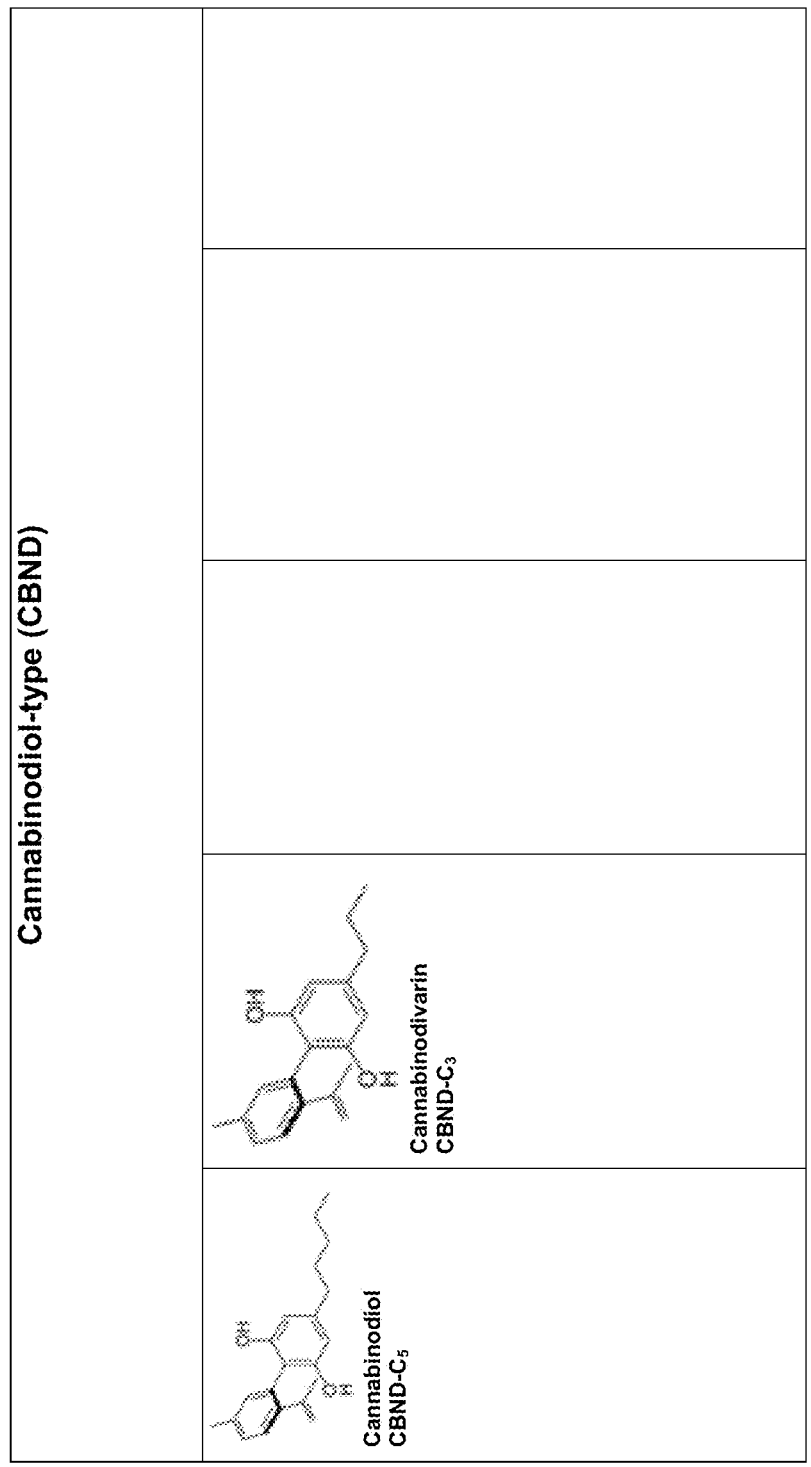
Figure 5E:
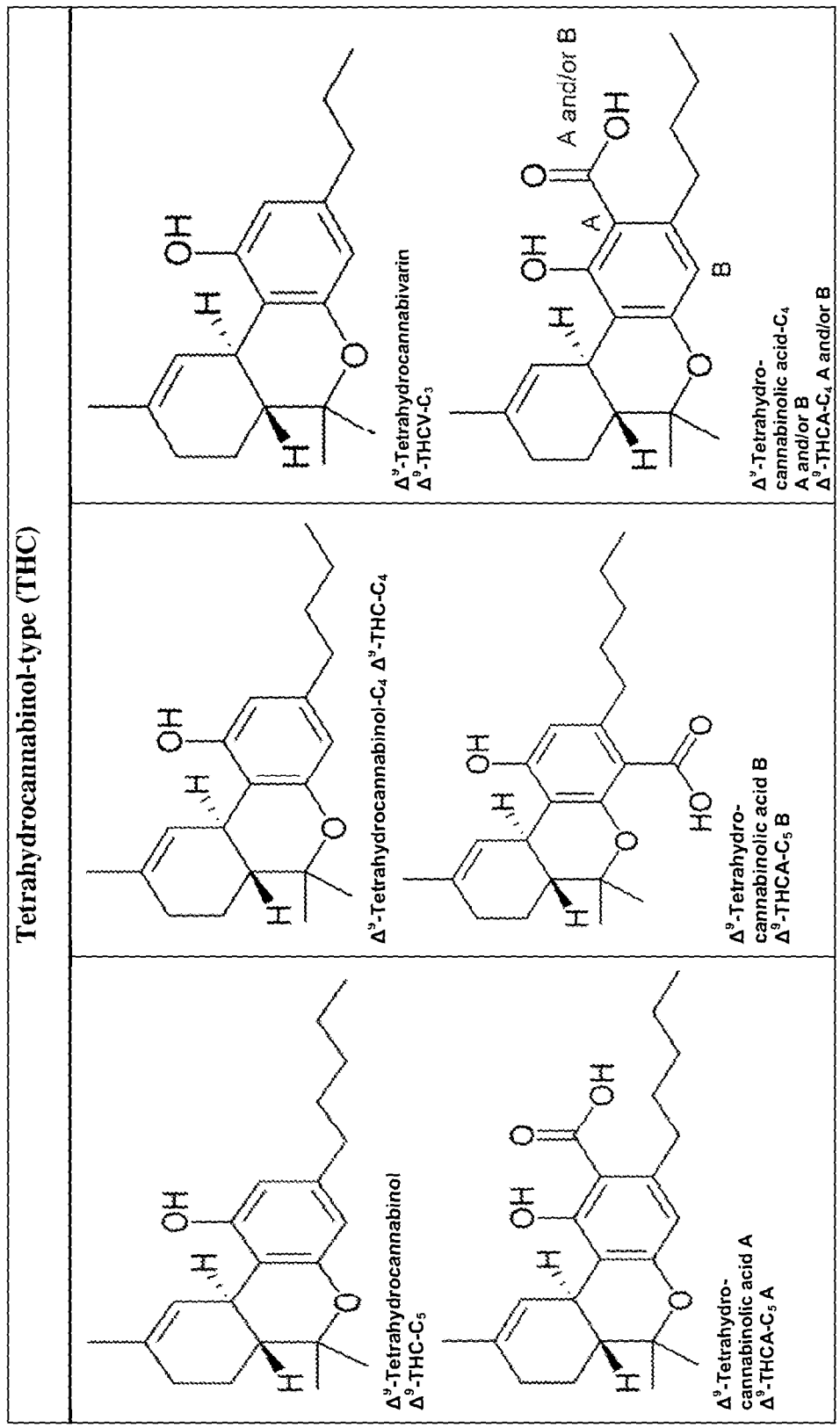
Figure 5F:
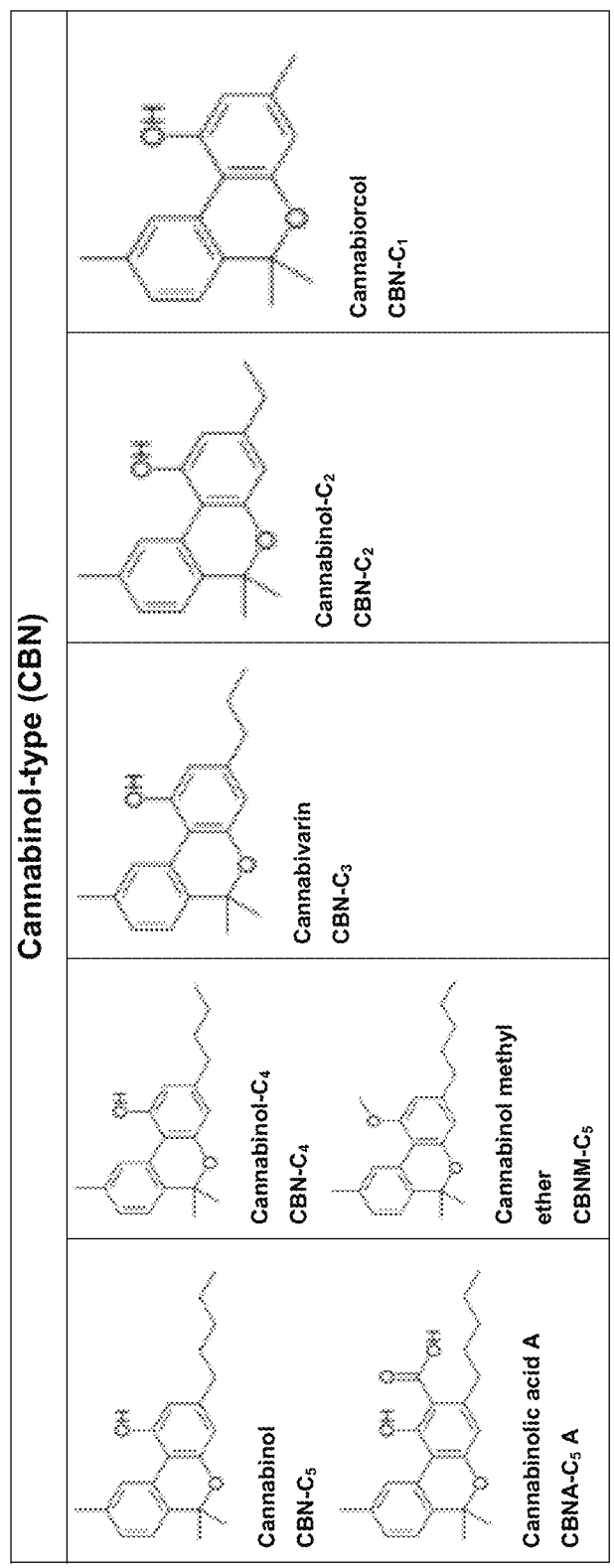
Figure 5G:
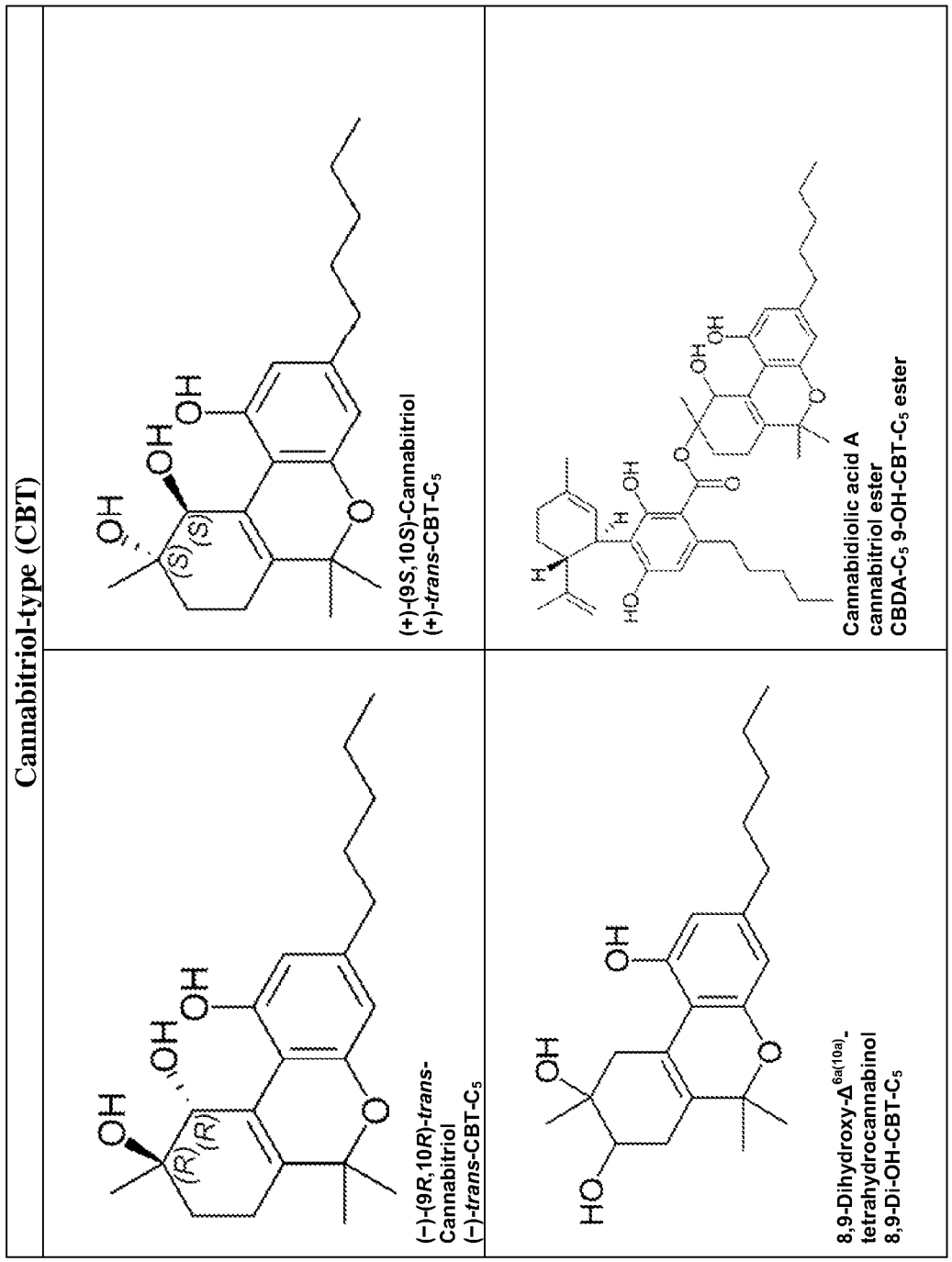
Figure 5H:
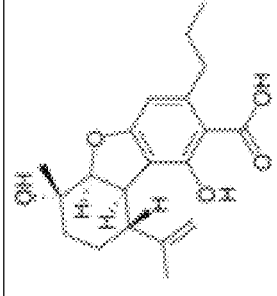
Figure 5I:
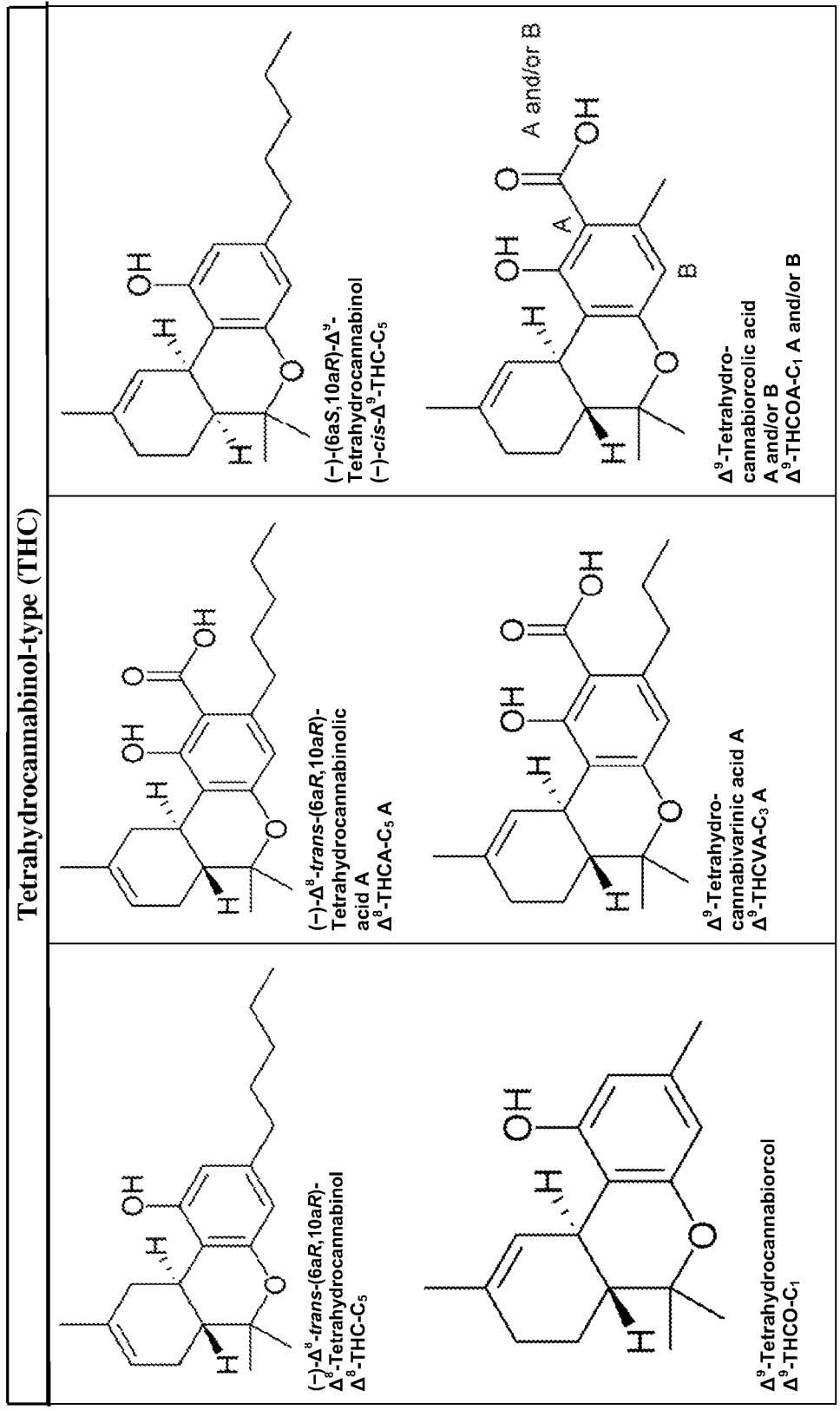
Figure 5J:
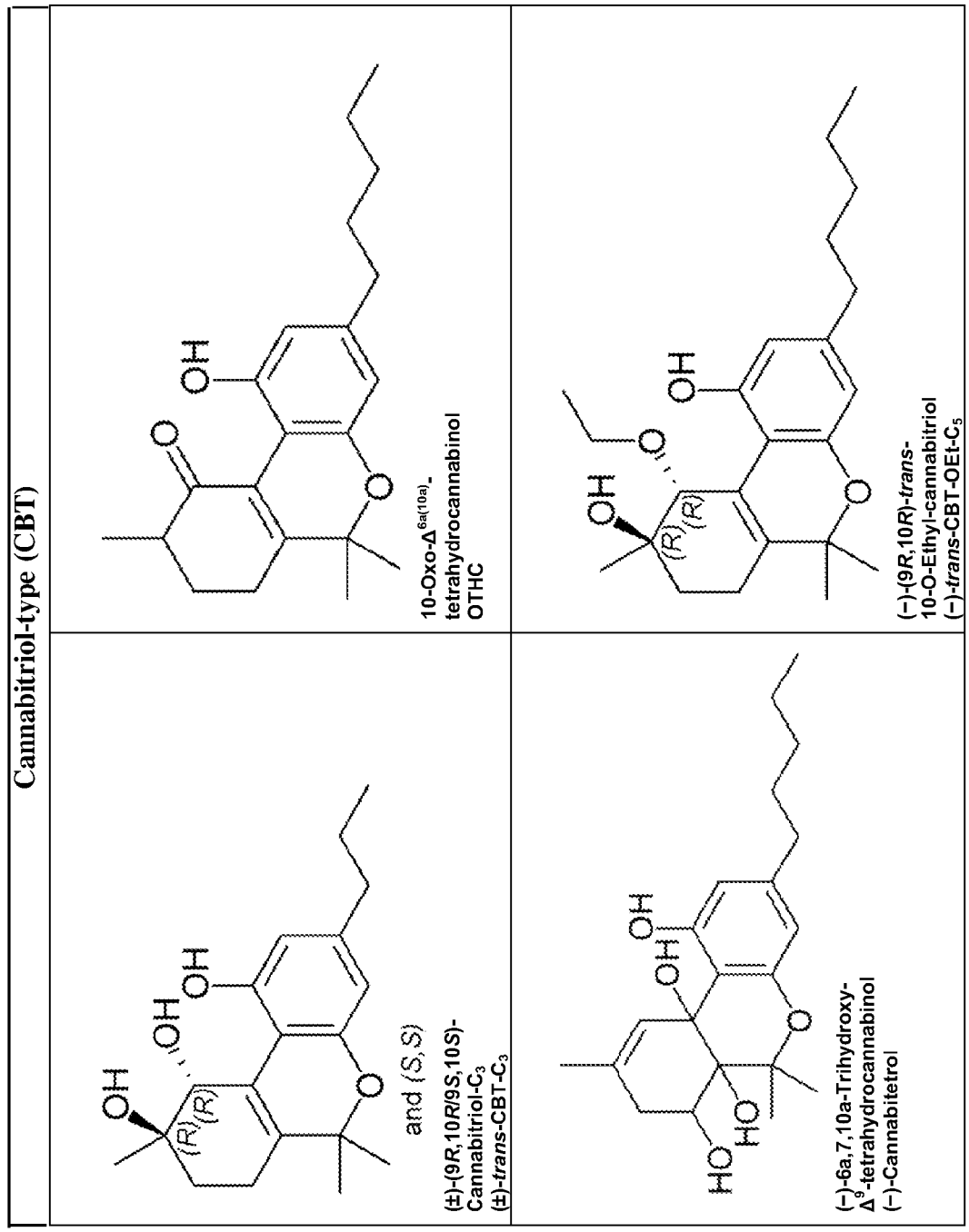
Figure 5K:
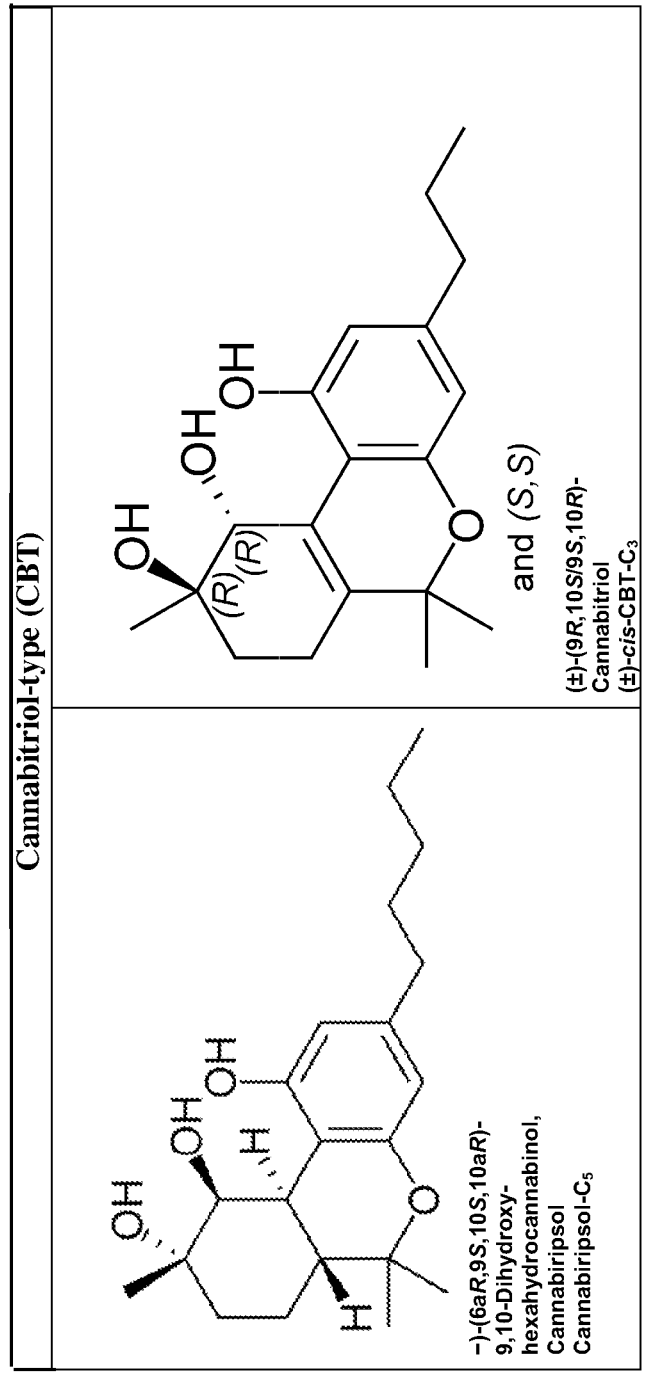

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present compositions and methods as described are not limited to particular embodiments described, and as such may, of course, vary. It is also to be understood that the terminology used herein is for the purpose of describing particular embodiments only, and is not intended to be limiting, as the scope of the present invention will be limited only by the appended claims.

As used herein and in the appended claims, the singular forms "a", "an", and "the" include plural referents unless the context clearly dictates otherwise. Thus, for example, a reference to "a polymer" includes a plurality of such polymers and reference to "the adhesive" includes reference to one or more adhesives and equivalents thereof known to those skilled in the art, and so forth.

Unless otherwise indicated, and from time to time expressly stated, all numbers expressing quantities of ingredients, properties such as molecular weight, reaction conditions, and so forth used in the specification and claims are to be understood as being modified in all instances by the term "about."

All methods described herein can be performed in any suitable order unless otherwise indicated or otherwise clearly contradicted by context. The use of any and all examples, or exemplary language (e.g., "such as") is intended merely to better illuminate the invention and does not pose a limitation on the scope of the invention otherwise claimed.

Groupings of alternative elements or embodiments of the invention disclosed are not to be construed as limitations. Each group member may be referred to and claimed individually or in any combination with other members of the group or other elements found. It is contemplated that one or more members of a group may be included in, or deleted from, a group. When any such inclusion or deletion occurs, the specification is herein deemed to contain the group as modified unless specifically noted.

Unless defined otherwise, all technical and scientific terms used herein have the same meaning as commonly understood by one of ordinary skill in the art to which this invention belongs.

Materials and Methods, Generally
Cannabinoid Receptor Binding Agents

A "cannabinoid receptor binding agent" refers to a moiety that binds, fully or partially, to a human or non-human cannabinoid receptor, as further described below. Briefly, human endocannabinoid receptors include cannabinoid receptors 1 and 2, and putative cannabinoid receptor GPR55 and GPR119. A cannabinoid receptor binding agent may bind to particular regions with selected affinity and dissociation kinetics, and have a number of characteristics as further defined below. The use of various cannabinoid receptor binding agents are contemplated herein, including but not limited to those set forth in any of FIGS. 2, 3, 4, and 5A-D. One may combine cannabinoid receptor binding agents in a single cannabinoid receptor binding agent delivery vehicle (as described herein), and further, formulate for desired characteristics, such as practicability in manufacture, desired physiologic or therapeutic characteristics, or release profile.

One may use, for instance, a natural extract from *Cannabis sativa*, containing the phytocannabinoid receptor binding agents so produced by the plant in its natural state. While such composition may be relatively undefined, such extracts typically contain a mixture of moieties that bind to CB1, CB2 as well as other moieties. Such extracts have been used historically, with varying degrees of success. See, review, "*Cannabis* and *Cannabis* Extracts: Greater Than the Sum of Their Parts?" McPartland, John M., and Ethan B Russo. Co-published simultaneously in Journal of *Cannabis* Therapeutics (The Haworth Integrative Healing Press, an imprint of The Haworth Press, Inc.) Vol. 1, No. 3/4, 2001, pp. 103-132; and: *Cannabis* Therapeutics in HIV/AIDS (ed: Ethan Russo) The Haworth Integrative Healing Press, an imprint of The Haworth Press, Inc., 2001, pp. 103-132. Despite the relatively undefined nature of some of the extracts, this form may be particularly advantageous to both producers and consumers, in ease and practicability of administration.

More generally, a cannabinoid may be selected from among an endocannabinoid, a phytocannabinoid and a synthetic cannabinoid. An endocannabinoid compound refers to a compound structurally similar to that made endogenously in animals, regardless of the method of synthesis, including those in FIG. 2. Phytocannabinoids include Δ9-tetrahydrocannabinol ("Δ9-THC"—the primary psychoactive compound of *cannabis*), Δ8-THC as well as a number of other cannabinoids structurally similar to those have been isolated from *Cannabis sativa* (or other species), including, cannbigerol, channabichromene, cannabicyclol, cannabivarin, tetrahydrocannabivarin, cannabidivarin, cannabichromevarin, cannabigerovarin, cannabigerol monoethyl ether. Synthetic cannabinoid receptor binding agents are available. These may be, for instance, particular isomers of natural cannabinols. Nabilone and dronabinol are synthetic forms that are licensed for therapeutic use by relevant governmental authorities. HU-210 ("HU" for "Hebrew University") is reported to have 100 times the potency of THC. See, Understanding the 'Spice' phenomenon, European Monitoring Center for Drugs and Drug Addiction publication, Lisbon, November 2009. Exemplary cannabinoid receptor binding agents are set forth in FIGS. 2, 3, 4, and 5A-D.

One may prepare a cannabinoid receptor binding agent with desired characteristics by empirically testing against the desired receptor, and it is contemplated that cannabinoid receptor biology and chemistry will permit the development of novel cannabinoid receptor binding agents. One may, for instance, select for a cannabinoid receptor binding agent that selectively binds one or more of the transmembrane regions of CB1, CB2, or other receptors. See, Shim, J-Y., "Understanding Functional Residues of the Cannabinoid CB1 Receptor for Drug Discovery," Current Topics in Medicinal Chemistry 10: 779-798 (2010) (CB1). Transmembrane domains of CB1 and CB2 are homologous to some extent, and some cannabinoids bind both CB1 and CB2. Such binding may be with the same affinity, or different affinities, and may have the same or different dissociation constants, and may act similarly or differentially as agonists, antagonists, reverse antagonists, etc. on receptors so bound. One may prepare the product of a process of contacting a composition to a cannabinoid receptor and selecting a composition that binds to the receptor with a predetermined selectivity or affinity. One may test against synthetic cannabinoid receptors (or regions thereof), such as consensus receptor sequences having those amino acids identical in CB1 and CB2 transmembrane regions, and non-charged (or neutral) amino acids selected for those that are non-identical between the two. Similarly one may select a receptor binding agent selective for a consensus sequence among various species having similar, but not identical transmembrane regions.

The cannabinoid receptor binding agent may be selective for a cholesterol interaction recognition conserved sequence CRAC [L/V-X-Y-X-R/K], as present in the last 11 amino acids of the transmembrane helix 7 of both CB1 and CB2. The highly conserved CRAC region (82% amino acid identity) demonstrates CB1 differences from CB2 for one residue only: lysine 402 of CB1 corresponds to glycine 304 in CB2. See, Maccarrone, M., "Membrane environment and endocannabinoids signaling," Frontiers in Physiology doi: 10.3389/fphys.2010.00140 (2010). One may select for a cannabinoid receptor binding agent selective for the K402 region (for CB1) or G304 (of CB2) of the transmembrane helix 7 domain.

Particular cannabinoid receptor polymorphisms may be of particular interest. For instance, cannabinoid receptor gene polymorphisms, such as the CB1/poly AAT polymorphism, may play a role in particular conditions, and antagonizing this particular receptor form may treat, ameliorate, or alleviate such conditions. See, review, Yao, B. and Makie, K., "Endocannabinoid Receptor Pharmacology," In: D. Kendall and S. Alexander (eds.), Behavioral Neurobiology of the Endocannabinoid System, Current Topics in Behavioral Neurosciences 1, DOI: 10.1007/978-3-540-88955-7_2, Springer-Verlag Berlin Heidelberg 2009. One may use such receptors, or portions thereof, as targets against which to screen for suitable cannabinoid receptor binding agents.

Selection of the cannabinoid receptor binding agent may be determined in consideration of the receptor target (e.g., CB1, CB2, etc.) and whether one also wishes the cannabinoid receptor binding agent to bind to additional targets, such as a vanilloid receptor (e.g., TRPV1), or an epidermal growth factor receptor, for instance.

A cannabinoid receptor binding agent may be an agonist or an antagonist, or some combination (e.g., partial agonist, reverse agonist), and may be full or partial in activity. One will determine if one wishes to activate the target receptor, block the target receptor (that is, render the target receptor inactive), shut off a constitutively signaling target receptor, or other physiologic response. One may therefore select from among a cannabinoid receptor binding agent that acts as an agonist, an antagonist and various other forms (e.g., reverse agonist) as needed. This may be determined empirically, for instance, by ascertaining physiological effects of receptor binding in terms of downstream signal transduction. See, review, Yao, B. and Makie, K., "Endocannabinoid Receptor Pharmacology," In: D. Kendall and S. Alexander (eds.), Behavioral Neurobiology of the Endocannabinoid System, Current Topics in Behavioral Neurosciences 1, DOI: 10.1007/978-3-540-88955-7_2, Springer-Verlag Berlin Heidelberg 2009. The cannabinoid receptor ligands enumerated by Yao and Makie, at part 10 (10.1, Non-Selective CB1/Cb2 Receptor agonists; 10.2, CB1 Receptor antagonists; 10.3, CB2 Receptor Agonists; 10.4 CB2 Receptor Antagonists;) is incorporated herein by reference.

One may select the binding affinity of the cannabinoid receptor binding for the target receptor(s), as well as the dissociation rate or other ligand characteristics. A cannabinoid receptor binding agent may be of a predetermined affinity toward the subject cannabinoid receptor, and may bind all or part of the receptor moiety. For instance, cannabinoid subtypes may selectively have higher binding affinities for one type of cannabinoid receptor over another. Cannabinol is reported to have a 10 fold higher binding affinity to CB2 than to CB1, for instance, Munro S, et al., "Molecular characterization of a peripheral receptor for cannabinoids," Nature 365:61-65 (1993), whereas Δ9-THC, an active component of *Cannabis sativa*, has been shown to act as an agonist for CB1 but as a weak antagonist for CB2, Bayewitch M. et al., "(2)-D9-Tetrahydrocannabinol antagonizes the peripheral cannabinoid receptor mediated inhibition of adenylyl cyclase," Journal of Biological Chemistry 271:9902-9905 (1996). A cannabinoid receptor binding agent may bind part or all of the subject cannabinoid receptor. In terms of dosing, a high affinity cannabinoid receptor binding agent may be used in a relatively low concentration compared to a lower affinity cannabinoid receptor binding agent, for the same receptor activation resulting in a physiological response. One may prepare a mixture of such cannabinoid receptor binding agents, selective for particular receptors or portions thereof. Moreover, because some cannabinoids also bind to other receptors, one may select a cannabinoid receptor binding agent that binds one or more non-cannabinoid receptors. These include a vanilloid receptor, including a capsaicin receptor, and an epidermal growth factor receptor.

The term "selective," as in "selective cannabinoid receptor binding agent," as used here from time to time, denotes a preference for binding the subject cannabinoid receptor over other moieties. While specificity is included, complete binding specificity for only a single target is not necessary, and, particularly with some lipophilic cannabinoid receptor binding agents, the binding may be non-specific, although selective for a particular cannabinoid receptor. Thus, as discussed above, one may have a cannabinoid receptor binding agent that binds strongly to, for instance, CB1 and weakly to CB2 and even more weakly to a different G-coupled protein receptor.

Chemically Modified Cannabinoid Receptor Binding Agent

One may further chemically modify the binding agent for a variety of reasons, such as for ease in manufacturing, shelf stability, compatibility with substrate, or to have a desired release or pharmacokinetic profile. Modification may include the addition of one or more hydrophilic or hydrophobic polymer molecules, fatty acid molecules, or polysaccharide molecules. Examples of chemical modifiers include polyethylene glycol, alklpolyethylene glycols, DI-poly(amino acids), polyvinylpyrrolidone, polyvinyl alcohol, pyran copolymer, acetic acid/acylation, proprionic acid, palmitic acid, stearic acid, dextran, lecithin, carboxymethyl cellulose, pullulan, or agarose.

One may, for instance, seek to alter the hydrophobic properties of a cannabinoid receptor binding agent, by, for instance, chemically attaching a water-soluble moiety. The term "water soluble" denotes that the moiety is soluble to some extent in an aqueous environment, but total solubility is not required. Examples of water soluble polymers include (poly)ethylene glycols, such as those of a desired length, branched or unbranched. One may, for instance, attach a relatively water soluble polymer, such as a polyethylene glycol moiety, to a cannabinoid receptor binding agent. The attachment may be direct (as in a chemical bond) or may be through a linker moiety.

Such chemically modified cannabinoid receptor binding agent may be so modified for a particular formulation. Some cannabinoid compounds are particularly lipophilic. One may attach a water soluble polymer such as polyethylene glycol to alter the hydrophobic/hydrophilic profile of the molecule, while not changing the selectivity. Further, a chemical moiety may be used to sterically hinder binding to a cannabinoid receptor such that binding is sustained with a longer delivery profile.

Chemically Modified Form; Prodrug

Other types of chemical modification include those comprising a prodrug. Pro-drug forms may be used having a moiety that, when detached, permit the cannabinoid receptor binding agent to become active. (The term "active" in this context denotes cannabinoid receptor binding, whether or not the receptor is so activated for signal transduction, for instance).

One may seek to modify the cannabinoid receptor binding agent pharmacokinetic profile or duration in the blood stream, for instance and prepare a pro-drug form. One may prepare, for instance, an esterified cannabinoid receptor binding agent capable of releasing a cannabinoid receptor binding agent upon cleavage of the ester moiety. A number of moieties are available for such prodrug formation.

A linker moiety may permit the release of the cannabinoid receptor binding moiety upon a defined condition, such as in the presence of a second moiety, such as an enzyme. One may, for instance, prepare a mucosal delivered polymeric film comprising a chemically modified cannabinoid receptor binding agent, where the chemically modified cannabinoid receptor binding agent comprises a cannabinoid receptor binding agent linked to a polymer via a linking moiety, where the linking moiety is capable of hydrolysis, such as by an oral hydrolase.

Chemically Modified, Detectable Markers

A cannabinoid receptor binding agent may also be chemically modified by labeling the cannabinoid receptor binding agent, the particle, any chemical moiety or other moiety with a detectable marker, such as an imaging composition, such as a quantum dot. One may use a fluorescent, chemiluminscent, phosphorescent or other light-based detectable marker, or a colorimetric marker, for example. One may determine the presence or amount of cannabinoid receptor binding, the location or degree to which cannabinoid receptor binding ligand is delivered or bound, as well as other parameters in vivo. One may, for instance, attach a reagent for neuroimaging to a cannabinoid receptor binding agent, and administer such agent transmucosally through the nose (nasal mucus membrane), for delivery to brain, and thus detect cannabinoid receptor binding in the brain. A variety of detectable markers are available, including radioactive tags and other tags that may be further detected with an additional moiety, such as the case of using a peptide with a labeled antibody moiety.

Vesicles

Phospholipid, or non-ionic surfactants may aid in transport of the drug into and across the skin. Liposomes, ethosomes, niosomes, transferosome and other vesicles may function to enhance or control the transport of drug through the skin. A vesicle may have a pharmokinetic function as a rate-limiting barrier for absorption through the skin into the systemic circulation. A vesicle may serve as a penetration enhancer. In addition, enclosing an active ingredient in a vesicle along with other moieties may serve to assist in the physicochemical properties of the drug, e.g., enhance solubilization or three dimensional conformation aspects.

A vesicle may have a variety of surface characteristics. One may prepare a multilamellar liposomal vesicle, such that each layer has different properties. One may prepare a vesicle for acoustic drug delivery, such as delivering a sound thereby opening the vesicle via acoustic disruption, and delivering the contents. In addition, one may chemically modify a vesicle, such as adding a moiety for targeted delivery (or otherwise) to the vesicle surface, such as an antibody (or related moiety, such as an antibody fragment or peptibody). One may use a variety of combinations of characteristics in a single vesicle, and further may use a variety of vesicles in a single cannabinoid receptor binding agent delivery vehicle. One may add additional moieties, such as polymers as indicated above, to alter the inner or outer surface characteristics of a vesicle. Moreover, one may attach a detectable label (such as a radio label, florescent, luminescent, phosphorescent, etc. as described above) as desired for detecting the presence or amount of a vesicle, for instance, as a proxy for the presence or amount of cannabinoid receptor binding agent.

The use of vesicles may be particularly advantageous as they apply to lipophilic cannabinoid receptor molecule preparations unsuited for transdermal delivery. One may formulate such lipophilic cannabinoid receptor compositions within a vesicle. Such vesicle may be disposed on or within a solid substrate, or admixed in an activated polymeric composition for solidification in situ.

Nano- and Microparticles

Some embodiments of the present invention involve compositions or use of nano- or microparticles.

As used here, the prefix "nano" denotes a size range in the nanometer ("nm") scale. Sizes of such nanoparticle transdermal delivery vehicles include those in the about 1 to about 100 nm, about 100 to about 200 nm, about 200 to about 400 nm, about 400 to about 600 nm, about 600 to about 800 nm, and about 800 to about 1000 nm and microparticles in the about 1000 to about 2000 nm (1-2 micrometer ("µm") scale). (While the term "nanoparticle" is used in this section as such nanoparticle is widely practicable for drug delivery, similar considerations may apply to micro-sized particles as one of skill in the art will appreciate). Particles of certain sizes may be particularly advantageous for transdermal delivery from topical application. Certain particle sizes may facilitate entry to the lower dermal layers when applied to the surface of the skin. One will appreciate that smaller particles provide for increased surface area over larger particles such that a higher concentration of cannabinoid receptor binding agent may be applied per volume of particles. One may prepare nanoparticle of about 60 nm to about 100 nm in diameter by, for instance, high pressure processing.

A nanoparticle may be metal, lipid, polymer or other materials, or a combination of materials. The particles may be charged (+ or −) or neutral, and one may consider other formulation compositions in determining the nature or degree of charge desired. Biocompatable materials may be preferable for delivery into a living subject if quantities would otherwise result in a deleterious effect. The material may be persistent, or may be biodegradable, or some combination.

Nanoparticles may be functionalized such that another moiety may be attached thereto. Inorganic nanoparticles, for example, may be surface functionalized such that another moiety may be chemically connected to the nanoparticle. Surface functionalization may involve the use of a moiety comprising an anchor group, a spacer and/or a functional group. The anchor group is a moiety attached to the nanoparticle surface. Anchor groups may be trialkoxysilanes, phosphonates, sulfonates or other bidentate ligands. The spacer may be a polymer or any moiety that connects the anchor group to the functional group, with any desired length, charge, or other characteristic. The functional groups attached to the surface of the nanoparticles depend on the further processing. One may use, for example, moieties functionalized for crosslinking One may functionalize a cannabinoid receptor binding agent to bind to a moiety for surface functionalization of a nanoparticle.

Alternatively or in addition, nanoparticles may be coated such that moieties may bind to the coating. For example, a nanoparticle may be coated with albumin, silicone or other agent to which a cannabinoid receptor binding agent may be embedded or chemically attached. Other moieties may be concomitantly so attached, such that the nano (or micro-) particle is a carrier for the active ingredient as well as other moieties. One may encapsulate a nano- (or micro-) particle within a vesicle. One may add additional moieties, such as permeation enhancers, within the vesicle so encapsulating the nano- (or micro-) particle carrying the cannabinoid receptor binding agent. A peptide moiety may be attached, for instance, to assist in cell targeting. A peptide, such as one selective for a cell surface moiety, or a membrane translocation peptide, may be used (the term "peptide" used to denote broadly a composition with a peptide bond and containing an amino acid or amino acid mimetic moiety).

One may prepare a combination of materials to deliver active moieties in phases, such as a temporal fashion, also referred to as phasic delivery. One may prepare a particle with an outer coating that is dissolvable at a predetermined rate, to deliver the present cannabinoid receptor binding agents. Various combinations of coatings and degradable chemical attachment moieties may be used to deliver a cannabinoid receptor binding agent with a particular profile for release or pharmacokinetics.

As mentioned above, a nanoparticle may be comprised of a metal, and this includes those having a metal core. Metal nanoparticles are useful when targeted to a cell for generating hyperthermia, and thus ultimately killing the cell. One may use a metal and a cannabinoid receptor binding agent bound thereto to target such cell for death by hyper-heat. A nanoshell can be designed to absorb and scatter light at a desired wavelength by adjusting the core and shell thickness. For instance, a nanoshell, that is, a central core with a coating, may be prepared having a silica core coated with an ultra-thin metallic layer, such as gold. The metal shell converts absorbed light into heat. For use with tissue, for instance, one may prepare a nanoshell reactive with a light wavelength that penetrates skin, such as near infrared light (NIR). By supplying a NIR from a laser, the particle heats up and kills the tissue in the local environment. In this non-invasive, locally delivered way, nanoshells may be used to destroy a tumor. Local delivery of a cannabinoid receptor binding agent may assist in the treatment, amelioriation or alleviation of such treatment.

One may use a magnetic particle, such as a nano- or micromagnetic particle. The magnetic particle may be used as a carrier for targeted magnetic delivery of a cannabinoid receptor binding agent to a desired area. One may include magnetic micro- or nano-particles as described herein, for purposes of delivering a therapeutic agent (for example) topically, and then releasing such agent transdermally, as for example, to a skin cancerous region (e.g., melanoma or sarcoma).

For instance, one may prepare a composition comprising a magnetic nano- (or micro-) particle having a cannabinoid receptor binding agent attached thereto. The magnetic nano- (or micro-) particle may also have a second therapeutic moiety attached thereto, such as an anti-cell proliferation moiety or a pain reducing moiety. A plurality of the magnetic nano- (or micro-) particles may be encapsulated within a vesicle. The vesicle containing the magnetic nano- (or micro) particles may further contain an adjuvant, excipient or carrier, such as albumin One may then use magnetic guidance to guide the particles to a local area, such as a sarcoma or melanoma. If used on an internal organ, one may use a mucoadhesive to affix a patch, for instance, and use targeted magnetic field for delivery to a desired location.

Albumin, silicone and other materials may be used to prepare nano- (or micro-) particles. Polymers that may be suitable for use as nanoparticle transdermal delivery vehicles include those listed below, as well as polyketals. Nano- or micro-particles formulated from polyketals degrade into neutral (as opposed to acidic) compounds comprised of acetone and diols, and should therefore avoid inflammatory problems associated with some polyester-based materials. Yang, S. C. et al., "Polyketal Copolymers: A New Acid Sensitive Delivery Vehicle for Treating Acute Inflammatory Diseases," Bioconjugate Chemistry 19: 1164-1169 (2008).

A nanoparticie may be in any number of geometric configurations. A nanoparticle may be in the form of a nanosphere (a matrix in which an active ingredient is dispersed throughout) and a nanocapsule (that is, the active ingredient is confined in a cavity surrounded by a polymeric membrane). The materials and methods may vary, depending on the particular characteristics so desired. A particular nanosphere may comprise, consist of, or consist essentially of a composition selected from poly(isohexylcyanoacrylate), poly(methylcyanoacrylate) and biodegradable poly(ethylcyanoacrylate), for example. A nano particle may be coated with a hydrophilic polymer, such as polyethylene glycol, a poloxamine, a poloxamer and a polysaccharide to provide hydrophilic and neutral chains at the particle surface. Dendrimers may be used.

Particular nanoparticles may be in the form of a nanofibers, such as hollow nanofibers and core-shell nanofibers, and nanorods (or a hollow nanorod as a nanotube) may be used (here collectively referred to as "nanofibers" unless otherwise indicated). The present cannabinoid receptor binding agent delivery vehicles may comprise, consist or consist essentially of a cannabinoid receptor binding agent and a nanoparticle in the form of a nanofiber or nanotube. Particularly, nanofiber material such as that produced by electrospinning, may be used. A cannabinoid receptor binding agent may be adsorbed, chemically attached, or incorporated within a nanofiber composition. The nanofiber composition may be comprised of, consist of, or consist essentially of silicon, and may be the product of the process of electrospinning Characterization In general, drug substances formulated for human therapeutic use should be adequately identified. Of particular relevance are physicochemical and biological properties that can influence the performance of the drug product and its manufacturability, or were specifically designed into the drug substance (e.g., solid state properties). Examples of physicochemical and biological properties include solubility, water content, particle size, crystal properties, biological activity, and permeability. These properties could be interrelated and, when appropriate, should be considered in combination.

Excipients, Diluents, Adjuvants, Carriers

A variety of excipients, diluents, adjuvants, carriers, and other non-bioactive agents may be so used. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives. (e.g., Thimersol, benzyl alcohol) and bulking substances (e.g., lactose, mannitol). The excipients chosen, their concentration, and the characteristics that can influence the drug product performance (e.g., stability, bioavailability) or manufacturability should be considered relative to the respective function of each excipient. This should include all substances used in the manufacture of the drug product, whether they appear in the finished product or not (e.g., processing aids). Compatibility of excipients with other excipients, where relevant (for example, combination of preservatives in a dual preservative system), should be established. The ability of excipients (e.g., antioxidants, penetration enhancers, disintegrants, release controlling agents) to provide their intended functionality and to perform throughout the intended drug product shelf life should also be demonstrated.

In particular, one may use a powder, such as talc or silica powder, in combination with a cannabinoid receptor binding agent, optionally disposed on a solid substrate, such as a patch. One may use a gel, or lotion, with which a cannabinoid receptor binding agent is admixed. The cannabinoid receptor binding agent may be chemically modified, or a pro drug, and may be attached to a nano-particle, or within a vesicle, such as a liposome or ethosome. Any suitable combination as described may be used as appropriate.

Localized Delivery Generally

The present invention relates to local delivery of a cannabinoid receptor binding agent and related compositions and methods. The term "delivery vehicle," as used from time to time herein, denotes an item suitable for delivering a cannabinoid receptor binding agent to a desired location. The present invention relates in particular aspects to local, as opposed to systemic, delivery in a body. In other aspects, the present invention relates to local, such as topical, administration for more broad delivery into the systemic circulation. The present invention relates, in particular embodiments, to cannabinoid receptor binding agents on a solid substrate, or on a substrate capable of solidifying in situ.

The local delivery of a cannabinoid receptor binding agent may be via a topical delivery vehicle. Although a topical delivery vehicle may initially deposit a cannabinoid receptor binding agent on the surface of an organ, such as the skin, the cannabinoid receptor binding agent ultimately be delivered through the organ surface to a distal area, such as transdermal delivery and transmucosal delivery. Thus, the present invention, in some aspects, relates to the local delivery of a cannabinoid receptor binding agent including topical application of a cannabinoid receptor binding agent delivery vehicle for topical delivery of a cannabionoid receptor binding agent, transdermal delivery of a cannabinoid receptor binding agent and transmucosal delivery of a cannabinoid receptor binding agent. Such delivery can range from drug-in-adhesive matrix systems to more complex systems that require microelectronics. These include passive systems (e.g., drug in patches, gels, foams, films, and spray-on films) and active systems (e.g., iontophoresis and sonophoresis).

A number of patch-based delivery systems are commercially available, and such systems may have different drug release mechanisms. (The term "patch" denoting at least one solid substrate). Reservoir systems generally hold the drug prior to diffusion through the solid substrates. One may have the drug in a matrix (that is, in a gel or other composition with predetermined passive leaching), and optionally use an additional rate controlling membrane. Patches generally have a backing and a liner, to confine and stabilize the drug containing areas. Because the patch itself is a drug storage unit, packaging and shelf stability should be considered in conjuction with the active ingredients. In addition, appropriate adhesives should be used, particularly where the patch is for chronic delivery and the wearer runs the risk of the patch displacing from the skin. Other concerns relate to irritation from the drug compound or the patch itself in direct contact with the skin.

One may include the present cannabinoid receptor binding agent within such patch, such as with a reservoir or matrix, or further formulate as described herein. The present invention contemplates, for instance, a cannabinoid receptor binding ligand attached to a nanoparticle disposed on or within a solid substrate, such as a patch. The present invention contemplates the use of a patch with a reservoir having a cannabinoid receptor binding agent attached to a nanoparticle disposed within such reservoir. One may further have a cannabinoid receptor binding agent attached to a nanoparticle within a matrix substrate so disposed on the patch. One may formulate the cannabinoid receptor binding agent to be chemically modified such that upon delivery by nanoparticle, the active ingredient enters the tissue at a desired release rate. One may formulate one or more cannabinoid receptor binding molecules attached to a nanoparticle within a vesicle, and then in a reservoir or matrix so disposed on a patch.

Topical Application for Topical Delivery

Topical delivery systems, on the other hand, contain a therapeutically active drug substance. The delivery system itself may come in a wide variety of forms, and the present invention encompasses a variety of topical delivery means, including cannabinoid receptor binding agents associated with a solid substrate, or a substrate that can be solidified in situ.

One such solid substrate is a patch, as described in, for example, U.S. Pat. Nos. 6,113,940 and 6,328,992. Such solid substrates may be used for localized delivery topically on the dermis, or transdermally, to enter the systemic circulation as well.

Briefly, as is well known in the art, the skin is comprised of two layers that cover a third fatty layer, as in FIG. 1. These three layers differ in function, thickness, and strength. The outer layer is called the epidermis; it is a tough protective layer that contains the melanin-producing melanocytes. The second layer (located under the epidermis) is called the dermis; it contains nerve endings, sweat glands, oil glands, and hair follicles. Under these two skin layers is a fatty layer of subcutaneous tissue, known as the subcutis or hypodermis. (For a background on skin anatomy, see, National Cancer Institute SEER Training Module, Skin Cancer: Melanoma, "Anatomy of the Skin," http://training.seer.cancer.gov/melanoma/anatomy/).

For topical application for topical delivery, one may use a cell penetrating agent that is not particularly amenable to transport through the upper layers of the skin to the lower dermis and systemic circulation. Particular materials, such as silica-based material, more particularly, a nano silica, may be advantageous.

For a substrate that can be solidified in situ, the present cannabinoid receptor binding agents may be incorporated into a polymeric composition for delivery as a fluid or gel for injection, for instance, and then solidified after spreading. Some examples include the use of photo-activated crosslinkers that permit properly derivatized polymers to be crosslinked in the presence of predetermined light wavelengths. This permits local delivery of the present compositions as a spreadable gel or paste (for instance), and then solidifying such as to create a solid substrate in situ.

Adhesion

Adhesion can be defined as the bond produced by contact between a pressure-sensitive adhesive and a surface. Bioadhesion is defined as an ability of a material to adhere to a biological tissue for an extended period of time. Suitable adhesives should be used for adhering component layers of a patch, for example, as well as adhering a solid substrate (such as a patch) to the topical location on the body. A particularly viscous cannabinoid receptor binding agent admixture, such as a *Cannabis* sp. extract, may serve as an adhesive, or may be admixed with a suitable adhesive.

Topical Application for Transdermal Delivery

Molecules can penetrate the skin by three routes: through the intact stratum corneum, through sweat ducts, or through the sebaceous follicle. The surface of the stratum corneum presents more than 99% of the total skin surface available for percutaneous drug absorption. Passage through this out most later is the rate limiting step for percutaneous absorption.

Transdermal delivery of a substance applied to the skin is generally stepwise, that is, first, absorption by stratum corneum, second, penetration of drug though viable epidermis, and then, if there is excess drug, uptake of the drug by the capillary network in the dermal papillary layer. Physicochemical properties of drug substances affecting topical permeation include partition coefficient (that is, of a penetrant molecule from a solution on to the stratum corneum), pH-condition, drug solubility, concentration, particle size, polymorphism or uniformity, and molecular weight among other things Permeation enhancers, such as chemical solvents or surfactants, anionic surfactants, cationic surfactants, non-ionic surfactants (e.g., bile salts), may be of practical utility. Also, physical permeation enhancers, such as electrical current (intophorosis, electroporation), sonophoresis, phonophoresis, may also be of practical utility.

Topical Application for Transmucosal Delivery

One may desire delivery on or through mucosal membranes, and this may be particularly advantageous where delivery of lipophilic cannabinoid receptor binding agents is to be delivered.

Transmucosal—Mucoadhesives

In the case of polymer attached to the mucin layer of a mucosal tissue, the term "mucoadhesion" is used. Various commercial adhesives are available, such as the POLYOX™ product line of a mucoadhesive polymers (Dow Chemical, technical data at Form No. 198-02142-1205, The Dow Chemical Company 2005.) Other mucoadhesives may be available and one will consider the location of the desired adhesion, the duration of the adhesion, the composition of the substrated to be adhered, and any other interactions. For example, one may seek to prepare a substrate out of mucoadhesive material into which a cannabinoid receptor binding agent has been admixed.

Transmucosal—Dissolvable

One may further desire a dissolvable delivery vehicle, particularly in association with a mucosal region, and may select a suitable dissolvable biocompatible material, such as dissolvable films. Chitin and related materials may also be so suited. Thus, one may prepare a transmucosal cannabinoid receptor binding agent delivery vehicle comprising a dissolvable substrate, and the dissolvable substrate may comprise a film.

One may, for instance, prepare a delivery for dental pain, to be applied topically in the mouth for delivery of a cannabinoid receptor binding agent to the site of pain, such as the gum or other inner area. The delivery vehicle may be in the form of a mucoadhesive patch, or may be a thin film or lozenge suitable for local delivery if held in place by the user.

Dosages and Drug Delivery

In general, the therapeutic effect is affected by drug delivery rate and the pharmacokinetic response. The drug delivery rate is affected by both the drug release rate from the patch (for example) as well as the skin permeation rate.

For topical medications, a general rule is that 30 g is required to cover the body surface, including carrier (e.g., cream, lotion, etc.). See generally, Fox, L. P., et al., "Chapter 62: Dermatological Pharmacology," page 1679-1706 In: Goodman and Gilman's The Pharmacological Basis of Therapeutics 11 ed. (2006), Brunton, L. L. ed. In general the size of a topical delivery device should be manageable by producers and consumers, and one standard for transdermal patches is 50 cm$^2$. One may consider the application of multiple patches to different areas for a patient in need thereof.

For dermatological conditions, dosages should be determined with regard to regional anatomic variation, altered barrier function, hydration, vehicle, application frequency and other considerations. In general, for diffusion, the higher the concentration the faster the drug delivery rate, and thus one may determine as steady state transdermal rate (that is, the input rate=drug elimination rate). Thus, if one can determine the drug elimination rate after a therapeutically effective amount, one may determine the desired drug input rate, and thus the desired drug concentration. See, for example, U.S. Pat. Nos. 6,113,940 and 6,328,992.

Dosing may be in consideration of the delivery rate of the drug itself. One may have a controlled release version, such as a prodrug, with a preselected delivery rate as determined by physiology availability of the active ingredient itself. With cannabinoids that are hydrophobic, there may be a reservoir effect, such that additional active ingredient is left on the skin/within the dermal layers, even after removal of a patch.

Biocompatibility

In general, the term "biocompatible" as used with terms such as "biocompatible polymer" or "biocompatible compound" and the like refers to materials that, in the amounts employed, are substantially non-toxic and substantially non-immunogenic when used dermally or (if referenced herein) transdermally or internally (in referenced context). A "biocompatible" composition may have some toxicity or immunogenicity or other adverse reaction, and whether or not such composition is useful for its intended purpose is largely a matter within the skill of a practitioner, in consideration of safety and efficacy, as well as commercial acceptability.

Substrate Solidified In Situ

The present invention contemplates the use of substrates in a fluidic state (that is, flowable state such as a gel or paste) that are solidified in situ. These may be particularly advantageous for directed application via injection through a syringe or other applicator, for instance, and then fixing the application location by solidifying the injected. One example is the preparation of a polymeric gel that may be sufficiently flowable through a syringe onto a body surface, and then solidified through cross-linking of the polymeric constituents in situ. This may permit the local, topical delivery to body surfaces that may not be amenable to a patch, such as the surface of the eye, or internal organs.

Solidification may be accomplished by cross-linking polymeric (or potentially, monomeric) moieties, and suitable cross-linking and initiation agents and conditions will be chosen based on the chemical structure of the polymeric composition, the desired properties of the solidified product, and other considerations as described below and further known in the art.

Polymeric Materials

Useful synthetic materials are polylactic acid) (PLA), poly (glycolic acid) (PGA), and their copolymers, poly(lactic-co-glycolic acid) (PLGA) and polyethylene glycol diacrylate monomers ("PEG-diacrylate") may be used as a starting point for selectively customizing the mechanical and persistence (durability) properties. Additionally, monomers such as PEG-DA can be mixed (e.g., 0.1%-10% of the composition by mass could be mixed with PEG-DA monomer). Synthetic hydrogels include polyethylene oxide)(PEO) based polymers and can be found as copolymers such as Pluronic®, a triblock copolymer of polyethylene oxide) and poly(propylene oxide) (PEO-PPO-PEO), or derivatized to be capable of photoinitiated cross-linking, such as polyethylene oxide) diacrylate (PEODA). Some examples of useful synthetic polymers include, but are not limited to polyalkylene oxides, polyethylene glycols, polyethylene oxides, partially or fully hydrolyzed polyvinylalcohols, poly(vinylpyrrolidone), poly(t-ethyloxazoline), polyethylene oxide)-co-poly(propylene oxide) block copolymers (poloxamers and meroxapols), polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), and/or with additional acrylate species such as aminoethyl acrylate and mono-2-(acryloxy)-ethyl succinate; polymaleic acid; polyacrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as polyvinyl pyrrolidone), poly(N-vinyl caprolactam), and copolymers such as polyethylene glycol/poly(N-isopropylacrylarnide)thereof; polyoxazolines, including poly(methyloxazoline) and poly (ethyloxazoline); polyvinylamines, polyacrylamide (PAA), poloxamines, carboxymethyl cellulose, and hydroxyalkylated celluloses such as hydroxyl-ethyl cellulose and methyihydroxypropyl celluloses. One may use various combinations, and further various chemically modified forms or derivatives thereof.

Natural polymers may include glycosaminoglycans such as hyaluronic acid, chondroitin sulfate A, chondroitin sulfate C, dermatan sulfate, keratan sulfate, keratosulfate, chitosan, and derivatives thereof. Therefore, while not exhaustive, examples of natural monomers or polymers which may be used include: polypeptides, polysaccharides or carbohydrates such as polysucrose, hyaluronic acid, dextran, heparin sulfate, chondroitin sulfate, heparin, or alginate, and proteins such as gelatin, collagen, albumin or ovalbumin or copolymers or blends thereof. Celluloses include cellulose and derivatives, dextrans include dextran and similar derivatives. Extracellular matrix proteins, such as collagens, elastins, laminins, gelatins, and fibronectins include all the various types found naturally (e.g., Collagen I-IV) as well as those same collagens as produced by and purified from a recombinant source, fibrin, a naturally occurring peptide important for its a role in wound repair in the body, and alginate, a polysaccharide derived from seaweed containing repeating units of manniironic and guluronic acid, may also be used. One may use various combinations, and may include chemically modified forms, mimetics, or derivatives thereof. For proteins, one may use recombinant forms, analogs, forms containing amino acid mimetics, and other various protein or polypeptide-related compositions.

Crosslinking

One may solidify the subject composition in situ via crosslinking in the presence of suitable activating agents. One may select the type of cross linking reagent desired in conjunction with activating the subject polymer. For example, one may select heterobifunctional crosslinking moieties for use with a temperature sensitive reactive group and a photosensitive reactive group. Or one may have a single reactive moiety, such as light sensitive reactive group activated in a range of light that penetrates the skin, for instance. One may prepare nanoparticles with such functional groups such that a functional nanoparticle similarly crosslinks.

Photoactivated Crosslinking

In some embodiments, cross-linking occurs by irradiation with a light at a wavelength of between about 100-1500 nm, and if in the long wavelength ultraviolet range or visible range, 320 nm or higher, and may be at about 514 or 365 nm.

Chemical Crosslinking

In some embodiments, cross-linking is chemically activated by a chemical activator (rather than a photoactivator) to trigger the polymerization of monofunctional, heterobifunctional, and homo-bifunctional cross-linkers. For example, heterobifunctional crosslinking moieties may be selected from among cross-linkers having at one reactive end an NHS ester or other active ester functionality, and a sulfilydrylreactive group on the other end. The sulfhydryl-reactive groups may be selected from, for example, maleimides, pyridyl disulfides and alpha-haloacetyls. Numerous other sulfhydryl reactive moieties are well known in the art; any suitable sulfhydryl reactive moiety can be used. Further, other orthogonally reactive species are known in the art and can be chosen for use in heterobifunctional crosslinking agents of the invention. In some embodiments, polymerization occurs at conditions such as at body temperatures, suitable chemical moiety interaction conditions, and suitable light conditions.

Temperature

In some embodiments, cross-linking occurs at temperature in the physiologic range (e.g., about 37 degrees C.) and in some embodiments at temperatures warmer or cooler, such as temperature on the surface or just below the surface of the skin, or at a predetermined temperature depending on the initiator used and the desired outcome.

In addition, one may prepare a cannabinoid receptor binding agent delivery vehicle of the present invention using a wax (such as paraffin) that is liquidic with heat, and solidifies with cooling. One may, for instance, use a paraffin composition comprising a cannabinoid receptor binding agent. One may heat the mixture (using a hand wax consumer product or other device that heats the paraffin to a non-burning temperature) and apply to the skin surface for solidification.

Additional Bioactive Agents

Additional moieties may be included in the compositions described herein, such as patches, in situ solidified polymeric compositions, nano- or micro-particles and the like. These may include:

Therapeutic Moieties

Aspects of the present invention contemplate additional therapeutic moieties, such as agents suitable for topical or transdermal delivery simultaneously, before, after, or in seriatim, with the present cannabinoid receptor binding agents. Contemplated are those therapeutic agents that act on inflammation, pruritus, pigmentation disorders, and malignancies as further described herein, as well as other disorders potentially addressed through the cannabinoid receptor pathway. Such therapeutic moieties may be biotherapeutics (e.g., protein based), such as antibody therapeutics or related compositions, such as peptibodies. The amino acid sequence may be found in nature or maybe varied, as one will appreciate, and may include synthetic moieties, such as peptidomimetic regions.

Analgesics

Analgesics may be used in conjunction with the present cannabinoid receptor binding agents. Because some analgesics or anesthetics bind to the same receptors that the cannabinoid receptor binding agents may bind to, such as the vanilloid or capsaicinreceptors (TRPV1, and others), co-administration may alter the pharmacological properties of each. It is worth noting the reports of TRPV1 agonists exhibiting activity dependent ion transport, and thus may serve as selective analgesics. Wang, Li H. et al., "Activity-dependent targeting of TRPV1 with a pore-permeating capsaicin analog," PNAS—USA 108:8497-8502 (2011).

Examples of analgesics that can be used with the compositions and methods of the present invention include, but are not limited to, lidocaine, mepivacaine, bupivacaine, procaine, chloroprocaine, etidocaine, prilocalne dyclonine, hexylcaine, procaine, cocaine, ketamine, morphine, pramoxine, propophol, phenol, naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone), oxymorphone (dihydrohydroxmorphinone), phenadoxone, phenazocine, remifentanil, tramadol, tetracaine, and mixtures thereof, as well as pharmaceutically acceptable salts and esters thereof. In preferred embodiments, a composition includes an analgesic selected from the group consisting of lidocaine, hydromorphone, oxycodone, morphine and pharmaceutically-acceptable salts thereof.

Antibiotics

Antibiotics may be used with the compositions, methods, and kits of the present invention, such as including, but not limited to Acrofloxacin, Amoxicillin plus clavulonic acid (i.e., Augmentin), Amikacin, Amplicillin, Apalcillin, Apramycin, Astromicin, Arbekacin, Aspoxicillin, Azidozillin, Azithromycin, Azlocillin, Bacitracin, Benzathine penicillin, Benzylpenicillin, Carbencillin, Cefaclor, Cefadroxil, Cefalexin, Cefamandole, Cefaparin, Cefatrizine, Cefazolin, Cefbuperazone, Cefcapene, Cefdinir, Cefditoren, Cefepime, Cefetamet, Cefixime, Cefinetazole, Cefminox, Cefoperazone, Ceforanide, Cefotaxinae, Cefotetan, Cefotiam, Cefoxitin, Cefpimizole, Cefpiramide, Cefpodoxime, Cefprozil, Cefradine, Cefroxadine, Cefsulodin, Ceftazidime, Ceftriaxone, Cefuroxime, Chlorarnpenicol, Chlortetracycline, Clilacillin, Cinoxacin, Ciprofloxacin, Clarithromycin, Clemizole. penicillin, Clindamycin, Cloxacillin, Daptomycin, Demeclocycline, Desquinolone, Dibekacin, Dicloxacillin, Dirithromycin, Doxycycline, Enoxacin, Epicillin, Erthromycin, Ethambutol, Fleroxacin, Flomoxef, Flucloxacillin, Flumequine, Flurithromycin, Fosfomycin, Fosmidomycin, Fusidic acid, Gatifloxacin, Gemifloxaxin, Gentamicin, Imipenem, Imipenem plus Cilistatin combination, Isepamicin, Isoniazid, Josamycin, Kanamycin, Kasugamycin, Kitasamycin, Latamoxef, Levofloxacin, Lincomycin, Linezolid, Lomefloxacin, Loracarbaf, Lymecycline, Mecillinam, Meropenem, Methacycline, Methicillin, Metronidazole, Mezlocillin, Midecamycin, Minocycline, Miokamycin, Moxifloxacin, Nafcillin, Nafcillin, Nalidixic acid, Neomycin, Netilmicin, Norfloxacin, Novobiocin, Oflaxacin, Oleandomycin, Oxacillin, Oxolinic acid, Oxytetracycline, Paromycin, Pazufloxacin, Pefloxacin, Penicillin G, Penicillin V, Phenethicillin, Phenoxymethyl pencillin, Pipemidic acid, Piperacillin, Piperacillin and Tazobactam combination, Piromidic acid, Procaine penicillin, Propicillin, Pyrimethamine, Rifabutin, Rifamide, Rifampicin, Rifamycin SV, Rifapentene, Rokitamycin, Rolitetracycline, Roxithromycin, Rufloxacin, Sitafloxaein, Sparfloxacin, Spectinomycin, Spiramycin, Sulfadiazine, Sulfadoxine, Sulfamethoxazole, Sisomicin, Streptomycin, Sulfamethoxazole, Sulfisoxazole, Synercid (Quinupristan-Dalfopristan combination), Teicoplanin, Telithromyein, Temocillin, Tetracycline, Tetroxoprim, Thiamphenicol, Ticarcillin, Tigecycline, Tobramycin, Tosufloxacin, Trimethoprim, Trimetrexate, Trovafloxacin, Vancomycin, and Verdamicin or other known antibiotics.

Enzyme Inhibitors or Enzymes

Enzyme inhibitors which would tend to prevent degradation of relevant constituents may be included. For example, protease inhibitors capable of inhibiting collagenase activity, or hyaluonidase inhibitors capable of inhibiting hyaluronidase activity may be included if appropriate. Alternatively, if controlled biodegradability is desired, enzyme inhibitors for controlled degradation may be included in such a way to have a particular sustained release profile (e.g., encapsulation within a sustained release vehicle). In a further alternative method, selective degradation of a suitably predefined polymeric composition can be initiated by the use of a biologically compatible degradation agent, such as an enzyme which would hasten biodegradation.

Particulate Matter

Particulate matter may be admixed for imparting particular characteristics, such as strengthening, bulking or filling density agent. Materials giving structural strength, and durability, such as calcium containing materials (e.g., hydroxyl apatite) or carbohydrate containing materials, (e.g., chitin or chitosan) may be included as particulate matter, Such particulate matter may add to the persistence of the polymeric material. One may mix solid or semi-solid microparticles, such as silicone or lipid microparticles, to obtain a desired consistency.

Medical or Other Devices

Apart from chemical moieties, devices may be incorporated into the present cannabinoid receptor binding agent delivery vehicle. In one aspect, the present invention contemplates incorporation of micro- or nano-devices, such as pumps, for controlled delivery of a medicament. Similarly contemplated are nanosensors to determine body condition levels, such as temperature or, if suitable, levels of blood substances, such as cannabinoid, or other sensors to communicate information about the local environment to a receiver. For example, a micro device with reservoirs for one or more drugs can be localized within a composition of the present invention. Release of the drug can be triggered by communication with a programmed wireless receiver. Preprogrammed microprocessors, remote controls, or biosensors can be used to open micro reservoirs to achieve intricate chemical release models. One may, for instance, use a pre-filled cannabinoid receptor binding ligand reservoir with release controlled or monitored by devices.

Kits

One may prepare a kit for use by a medical practitioner or by a patient. The kit may include: a container of substrate comprising a cannabinoid receptor binding agent as described herein, optionally chemically modified, and further optionally attached to a nanoparticle, where the substrate is not solidified, but capable of solidifying in the presence of a suitable agent; and, a suitable agent for solidifying said substrate.

The container may be a pre-filled syringe or portion thereof (such as a syringe barrel). The substrate may comprise a composition capable of being injected through a syringe. The composition may be capable of crosslinking in the presence of an activating agent. The composition may be a polymeric composition having moieties capable of crosslinking upon suitable activation.

The activating agent may be a particular wavelength of light, heat, chemical condition or other activating agent. The suitable agent for solidifying the substrate may be a light source for producing such suitable wavelength of light, such as an ultraviolet or near infrared light source; a heat source, or a source for producing the chemical condition.

In particular aspects, the present invention includes a kit comprising: a prefilled syringe barrel containing an injectable composition, the composition comprising, consisting of, or consisting essentially of a substrate capable of solidifying in the presence of a suitable agent selected from among light, heat and a chemical condition; a cannabinoid receptor binding agent attached to a nanoparticle; a source for providing a suitable agent selected from among a light source, a heat source and a source for delivering the chemical condition.

In other aspects, the present invention includes a kit comprising: a container of a plant extract comprising a cannabinoid receptor binding moiety and a nanoparticle; a patch suitable for administration of the plant extract to the skin.

Optionally, the kit may contain any of the other listed compositions presented herein, such as additional analgesics, anesthetics, anti-cancer or anti-cell proliferation compositions (such as a curcumin composition), materials and instruments for disposition on the skin. The kit may be coded such that it may be registered or logged with governmental authorities, such as for prescription purposes.

Therapeutic Aspects

Treating, Ameliorating and Alleviating.

The present invention relates in some aspects to medicament and methods of therapeutic use. Terms used from time to time reflect this. The term "treating" refers to the therapeutic practice of curing or reducing the underlying etiology, e.g., eliminating a tumor cell. The term "ameliorating" refers to reducing the conditions characterizing the underlying condition, such as reducing an inflammatory reaction. "Alleviating" refers principally to alleviating symptoms associated with a condition, such as redness or irritation incident to eczema. The present compositions and methods need not totally eliminate a disease or condition, but rather, may have practical utility in methods of treatment and products pertaining to reducing the severity of a condition or its symptoms. The present invention may be used in conjunction with other therapeutic methods and courses of medical treatment.

While cannabinoid receptor biology is a field of ongoing study, the endocannabinoids system is apparent throughout the animal kingdom. The compositions and methods may be useful in veterinary settings, such as for pets and livestock, including dogs, cats, cows, sheep, horses and other domesticated animals. For humans, the present invention includes compositions and methods that comport with acceptable medical practice, including those having suitable safety and efficacy for regulatory approval for sale. Subjects in need of the present invention thus include animals, and particularly mammals, and more particularly, humans Diagnostic Aspects Aspects of the present invention may also be useful for research reagents, as, for instance, detecting or diagnosing cells or tissues containing cannabinoid receptors. One may so use a detectable marker, as indicated above, or other observable means of detecting the subject cannabinoid receptor binding agent, a cannabinoid receptor (or other receptor, such as vanilloid receptor that may also be bound by a cannabinoid receptor binding agent), or the presence or amount of a physiological response. One may, for instance, use a cannabinoid receptor binding agent with a detectable label disposed on a dermal patch to detect the delivery rate of the cannabinoid receptor binding agent to the target, such as an area of skin.

In particular, one may use the present cannabinoid receptor binding agent on a solid substrate to determine the presence or amount of particular cannabinoid receptor variants. For instance, certain cannabinoid receptor 1 variants are reportedly associated with particular conditions, such as addictive disorders, Benyamina, A. et al., "CNR1 gene polymorphisms in addictive disorders: a systematic review and a meta-analysis," Addiction biology 16: 1-6 (2011).

EXAMPLES

Reference Formulas

The following formulations are Reference Formulas embodying aspects of the present invention. Percentages are weight/weight approximations unless otherwise specified.

Formulation 1 is a composition for a: Cannabinoid Receptor Binding Agent With Hydrogel Polyvinyl Alcohol or Acrylic Acid Delivery Vehicle comprising about 2% to about 10% of polyvinyl alcohol or carbopol 980,934,940 or other crosslinked biocompatible gelling agent, about 0.5% to about 20% of cannabinoid receptor binding agent, about 20% to about 30% of propylene or polyethylene glycol, with the remainder being water.

Formulation 2 is a composition for a: Cannabinoid Receptor Binding Agent With Cross linkable Chitosan Gel Delivery Vehicle comprising about 2% to about 12% of azidobenzoic hydroxypropyl chitosan, about 30% to about 50% of cannabinoid receptor binding agent, about 10% to about 20% of propylene glycol, about 1% to about 5% of phosphatidylcholine or other similar phospholipid, with the remainder being water.

Formulation 3 is a composition for a: Cannabinoid Receptor Binding Agent With PLGA Nanosphere Solution comprising about 50% to about 75% of PLGA (50:50, 25:75, 75:25 polymer combinations), about 25% to about 40% of cannabinoid receptor binding agent, about 1% to about 5% of PVA, with the remainder being water or Polyethylene glycol/propylene glycol.

Formulation 4 is a composition for a: Cannabinoid Receptor Binding Agent PolyKetal Delivery Vehicle comprising about 10% to about 20% of Polyketal, about 10% to about 30% of cannabinoid of choice, about 0% to about 20% of propylene glycol or polyethylene glycol, and about 1% to about 5% of phosphatidylcholine.

Formulation 5 is a composition for a: Cannabinoid Receptor Binding Agent Bound Nano Silica Solution Delivery Vehicle comprising about 1% to 30% of Cannabinoid of choice, about 20% to about 40% of hybrid organic-inorganic $SiO_2$—Polyethylene glycol (calcine and noncalcine), about 1% to about 20% of ethanol, and about 1% to about 5% of lecithin or other phospholipid Formulation 6 is a composition for a: Cannabinoid Receptor Binding Agent Layered Delivery System Delivery Vehicle comprising about 30% to 50% of PLGA cannabinoid loaded nanospheres, hydrogel, or silica, about 20% to about 30% of polyketal, and about 10% to about 20% of propylene glycol or ethanol.

Formulation 7 is a composition for a: Cannabinoid micro polymeric loaded sphere comprising about 10% to 20% of cannabidiol, about 30% to 40% of polyethylene glycol (Sigma®), and about 40% to about 55% of ethyl levulinate (Sigma®). In one embodiment, about 5 g of cannabidiol is dissolved in about 11.55 gram of polyethylene glycol (Sigma®) in a round bottom flask and homogenized with a rotor stator for about 90 seconds. A magnetic stirrer is then added to the flask for agitation. About 15.12 grams of ethyl levulinate (Sigma®) is added to the mixture and the flask is then heated to about 90° C. using an oil bath. The mixture is then pulled to a vacuum of about 20 mmHg and is mixed for about 180 minutes. The resulting mixture is stored under refrigeration for further use.

Formulation 8 is a composition for a: Cross linked structure with cannabinoid loaded micro spheres. In one embodiment, approximately 1.02 grams of 4-azidobenzoic hydroxypropyl chitosan (synthesized) is dissolved in the full quantity of Formulation 1 at 90 C and is allowed to cool to room temperature. Approximately 850 microliter of the mixture is then evenly applied over a 40 $cm^2$ area over the anterior antebrachial region proximal to the anterior wrist crease of the test subject using a modified film applicator blade (Gardco®). An 8 W germicidal UV bulb (254 nm) is then used to irradiate the area for about 40 seconds. The result is a thin solid substrate cannabinoid delivery system employing a range of sub-micron (nanometer) to micron sized drug loaded polymeric spheres cross linked together for an optimal drug delivery system.

Formulation 9 is a composition for a: Cannabidiol nano particle formulation. In one embodiment, about 4 grams of cannabidiol is dissolved in about 16 grams of hexane (Sigma®) in a round bottom flask. About 10 grams of PLGA (50:50 mix, Lactel) is added with about 100 ml of dichloromethane (Sigma®) and high speed homogenization (IKA Turrax T25) for about 30 seconds. The mixture is then added dropwise to a 5% polyvinyl alcohol solution that undergoes constant high speed homogenization while being cooled with an ice bath. Completed mixture is then combined with Tween 85 and solvent evaporation took place (IKA RC10). The resultant powder undergoes multiple washes with water and centrifugation. The final product is dried under a vacuum of about 10 mmHg. Cannabidiol loaded PLGA nano-spheres in the range of about 150-300 nm are obtained.

Formulation 10 is a composition for: Cannabidiol nano particle formulation. In one embodiment, about 4 grams of cannabidiol is dissolved in about 16 grams of hexane (Sigma®) in a round bottom flask. About 3 grams of PLGA (50:50 mix, Lactel) is added with about 100 ml of dichloromethane (Sigma®) and high speed homogenization (IKA Turrax T25) takes place for about 30 seconds. The mixture is then added to a 0.5% polyvinyl alcohol solution that undergoes constant high speed stirring while being fed into an ultrasonic flow through cell (Hielscher®, UIS250). The residence time in the cell is about 14 seconds with a sonicating power of about 32 watts. Solvent evaporation and washing occurs shortly thereafter. Cannabidiol loaded PLGA nanospheres in the range of about 450-650 nm are obtained.

Formulation 11 is a composition for a: PLGA patch. In one embodiment, about 1 gram of the powder of Formulation 9 is then combined with about 1 gram of polyethylene glycol (Sigma®) and about 350 micrograms of a suitable pressure sensitive adhesive (DURO-TAK 87-207A, Henkel®). The resulting mixture is then applied to a laminate backing layer (Scotchpack® 9730, 3M) with a film applicator blade (Gardco®). The resulting solid substrate is then dried under constant flowing air at about 75 C. A release liner is then applied for safe packaging (Scotchpack® 1022, 3M).

Formulation 12 is a composition for a: PLGA patch 2. In one embodiment, about 1 gram of the powder of Formulation 10 is then combined with about 1 gram of polyethylene glycol (Sigma®) and about 350 micrograms of a suitable pressure sensitive adhesive (DURO-TAK 87-207A, Henkel®). The resulting mixture is then applied to a laminate backing layer (Scotchpack® 9730, 3M) with a film applicator blade (Gardco®). The resulting solid substrate is then dried under constant flowing air at about 75 C. A release liner is then applied for safe packaging (Scotchpack® 1022, 3M).

Formulation 13 is a composition for a: Microsphere patch. In one embodiment, about 1 gram of the solution of Formulation 7 is then combined with about 0.5 grams of polyethylene glycol (Sigma®) and about 250 micrograms of a suitable pressure sensitive adhesive (DURO-TAK 87-207A, Henkel®). The resulting mixture is then applied to a laminate backing layer (Scotchpack® 9730, 3M) with a film applicator blade (Gardco®). The resulting solid substrate is then dried under constant flowing air at about 50 C. A release liner is then applied for safe packaging (Scotchpack® 1022, 3M).

Formulation 14 is a composition for: Compressed pills. In one embodiment, about 1 gram of the solution of Formulation 7 is fully dried and combined with about 9 grams of starch (Sigma®) using a mortar and pestle. About 3 grams of a carboxylated polymer (Proloc 20, Henkel®), is mixed in further. About 5 mg tablets are made using a pill compressor. The pill is packaged in sterile foil packaging for further use.

Formulation 15 is a compositions for: PEGylated nano particles with cannabinoids for optimal dermal delivery. In one embodiment, about 10 ml (5 mg/ml) avidin (Sigma®) is reacted with about 100 ml palmitic acid (Sigma®) and is sonicated (18 W,) for about 5 minutes at about 40 C. The avidin-lipid is then extracted using a modified dialyser for about 12 hours with about 0.1% deoxycholase (Sigma®) to remove excess fatty acids. About 3 ml of the remaining solution is then combined with about 3 ml of about 3% poly(vinyl alcohol) (Sigma®) and about 300 milligrams of resulting mixture from Formulation 3 and is sonicated (400 W @ 35% duty, Hielscher®) briefly. The mixture is then centrifuged and washed to obtain avidin-lipid coated PLGA loaded nano spheres.

About 150 mg of polyethylene glycol is mixed into about 9.85 g of saline solution to form a stock solution. About 1 g of the stock solution is then mixed with about 300 mg of biotin (Sigma®) The resulting PEGylated biotin is extracted using a modified dialyser against saline solution for about 12 hours.

About 250 mg of avidin coated PLGA nano particles is combined with about 500 mg of PEGylated biotin and is incubated at about 30 C for about 30 minutes to form PEGylated PLGA loaded nanospheres. Nanospheres are isolated using a centrifuge.

Formulation 16 is a composition for: PLGA patch 3.

In one embodiment, about 1 gram of the solution of Formulation 15 is combined with about 1 gram of polyethylene glycol (Sigma®) and about 350 micrograms of a suitable pressure sensitive adhesive (DURO-TAK 87-207A, Henkel®). The resulting mixture is then applied to a laminate backing layer (Scotchpack® 9730, 3M) with a film applicator blade (Gardco®). The resulting solid substrate is then dryed under constant flowing air at about 75 C. A release liner is then applied for safe packaging (Scotchpack® 1022, 3M).

Dermatological Application

The present invention provides compositions and methods for treating, ameliorating, or alleviating conditions associated with the skin and hair Cannabinoid Receptors in the Skin and Periphery Cannabinoid receptors are found associated with the skin of humans and other animals Table 1 presents immunoreactivity of cannabinoid receptors in different skin cells, from Stander et al., "Distribution of cannabinoid receptor 1 (CB1) and 2 (CB2) on sensory nerve fibers and adnexal structures in human skin," Journal of Dermatological Science 38: 177-188 (2005).

TABLE 1

|  | Epidermis | Nerve Fibers | Adnexal structures, mast cells, macrophages |
|---|---|---|---|
| CB1 | Keratinocytes of the stratum, spinosum, and granulosum | Single epidermal nerve fibers, small unmyleinated subepidermal nerves, large dermal myelinated nerves | Differentiated sebaceous cells, differentiated epithelial cells of the infundibulum and inner root sheath of hair follicles, myoepithelial cells of eccrine sweat glands, sweat gland duct, mast cells, macrophages |
| CB2 | Basal keratinocytes | Single epidermal nerve fibers, small unmelinated subepidermal nerves, large dermal myelinated nerves | Undifferentiated sebaceous cells, undifferentiated infundibular hair follicle cells, myoepithelial cells of eccrine sweat glands, sweat gland duct, mast cells, macrophages |

The present topical applications may be used for dermal conditions, where the cannabinoid receptor binding agent is applied topically, but the active ingredient(s) may be delivered past the stratum corneum (having predominantly non-viable keratinocytes, and thus presenting a barrier) to viable tissue.

Conditions contemplated by the present invention include acne and related disorders (acne vulgaris, rosaceae), bacterial skin infections, benign tumors (moles, vascular lesions), skin cancers (e.g., basal cell carcinoma, melanoma, squamous cell carcinoma), dermatitis (atopic, contact, exfoliative, hand and foot, seborrheic, etc.), hair disorders (alopecia, and loss of hair), hypersensivity and inflammatory disorders (e.g., acute febrile neutrophilic dermatosis), parasitic skin infections (e.g., scabies), pigmentation disorders (albinism, hyperpigmentation, vitiligo), psoriasis, scaling diseases, burns, cuts, abrasions, and other conditions that damage the skin. In addition, the present invention contemplates compositions and methods for tattoo removal and other aesthetic skin conditions.

Depending on the underlying tissue to which a cannabinoid receptor binding agent is to be delivered, one may select among delivery vehicle including a solid substrate, such as a patch, or an activated polymer suitable for solidification in situ, such as by crosslinking in the presence of an activating agent, such as light. The delivery vehicle patch or activated polymer may comprise, consist of or consist essentially of a cannabinoid receptor binding agent optionally formulated with diluent, adjuvant or carrier.

While a delivery vehicle may be applied topically such as applying a patch to the skin surface, a cannabinoid receptor binding agent may be delivered below the skin surface to underlying dermal layers. A transdermal delivery vehicle moiety selected from among a permeation enhancer, a vesicle, and a particle as described herein.

Thus, the present invention encompasses a composition comprising a cannabinoid receptor binding agent for treatment, amelioration, or alleviation of a skin condition. The present invention further encompasses a cannabinoid receptor binding agent delivery vehicle for treatment, amelioration or alleviation of a skin condition, comprising one or more of a particle having a cannabinoid receptor binding agent attached thereto; a particle of (a) wherein the particle is about 10 microns to about 50 microns in size; a particle of (a) or (b) disposed on a substrate; a particle of any of (c) where the substrate is a solid substrate; or a particle of (c) where the substrate is an activated polymer capable of solidification in situ by a suitable activation agent.

In some embodiments, the cannabinoid receptor binding agent may be present at about 1% to about 55% by weight of the total composition. Preferably, the cannabinoid receptor binding agent is present at about 15% to about 40% by weight. If the cannabinoid receptor binding agent is a phytocannabinoid, then it may be present at about 30% to about 40% of the total weight of the composition. If the cannabinoid receptor binding agent is synthetic, then it may be present at about 10% by weight or less.

The particle may be a nanocrystalline cellulose particle that is present at about 75% of the total weight of the composition or less. If the particle is modified with a moiety, it may be present at about 2.5% to about 10% by weight of the composition. When the composition is used in a patch for tissue damage, the particle may be present at about 40% to about 60% by weight of the total composition.

Sample Applications
Dermatological Inflammation

Peripheral cannabinoid receptors are found in the various constituents of the skin, and therefore topical delivery to the skin of a cannabinoid receptor binding agent is contemplated herein for treatment, amelioration or alleviation of skin conditions.

While some keratinocytes are not normally found with physiologically active cannabinoid receptors, other dermal keratinocytes do have such receptors. See, Table 1, Stander et al., above. For instance, human epidermal keratinocyte proliferation and survival is reportedly modulated via sequential engagement of cannabinoid receptor 1, and TRPV1 (transient receptor potential vanniloid 1). Bal, I. T. et al., "Endocannabinoida Modulate Human Epidermal Keratinocyte Proliferation and Survival via the Sequential Engagement of Cannabinoid Receptor 1 and Transient Receptor Potential Vanniloid 1," Journal of Investigative Dermatology 131: 1095-1104 (2011).

Psoriasis

Psoriasis is thought to be a consequence of deleterious inflammation. Because psoriasis involves hyperproliferation of keratinocytes, topical administration of a cannabinoid receptor binding agent that inhibits keratinocyte growth is contemplated herein. See, WO 2008/127459, Pharmacological Treatment of Psoriasis. Topical treatment beyond the top layers of the skin to penetrate the dermis involves additional agents in order to deliver a therapeutically effective mount of a cannabinoid receptor binding agent (the term, "therapeutically effective" here denoting an amount sufficient to reduce silver scaling symptomatic of keratinocyte hyperproliferation). Bal et al. (cited above) report that the endocannabinoids anandamide markedly suppresses certinocyte proliferation and induces cell death, both in vitro and in situ.

One may prepare a topical formulation of a cannabinoid receptor binding agent for the treatment, amelioration, or alleviation of psoriasis. The topical formulation may be disposed on a solid substrate, or may be in a polymeric composition. The polymeric composition may be cross-linkable (and capable of solidifying) in situ by, for instance photoactivated cross linking The cannabinoid receptor binding agent may bind CB1 or CB2 or other cannabinoid receptors. Because activation of the CB1 receptor in seriatim with the TRPV1 receptor is reported to result in keratinocyte cell death, one may prepare a topical formulation of a cannabinoid receptor 1 agonist and a TRPV1 receptor agonist. Each constituent may be individually formulated for sustained release. For instance, the present topical formulation may be prepared so that the CB1 receptor agonist is released first, and then, the TRPV1 receptor agonist is released afterward. The formulation may comprise nano- or microparticles as carriers of a receptor agonist, such that the receptor binding agent (here, the cannabinoid receptor or the vanilloid receptor) is released to the subject keratinocytes. A nanoparticle may be functionalized such that a cannabinoid receptor binding agent is attached, and, particularly for penetration of the outer dermal layers, nanoparticles so functionalized including a cannabinoid receptor binding agent may be of suitable size permit penetration to lower layers of the dermis.

Wound Healing

The present invention, in yet other aspects, may be used to treat, ameliorate, or alleviate conditions associated with muscle wound healing. Skeletal muscle wound healing, in particular, involves a tissue repair process that recruits a number of immune cells, including macrophages and neutrophils, cells reported to display the CB2 receptor. Reportedly, the CB2 receptor is upregulated on skeletal muscle cells during the wound healing process. Yu, T-S. et al., "The cannabinoid receptor type 2 is time-dependently expressed during skeletal muscle wound healing in rats," International Journal of Legal Medicine 124:397-404 (2010). Thus, the present invention relates to a topical delivery preparation comprising a cannabinoid receptor binding moiety for wound healing.

While not wishing to be bound by theory, cannabinoid receptor agonists may treat, ameliorate or alleviate deleterious conditions associated with wounds by mobilizing stem cells that will home in on the wound location. Skin burn injury reportedly is associated with stem cell mobilization, Drukala et al., "Stem Cells, Including a Population of Very Small Embryonic-Like Stem Cells, are Mobilized Into Peripheral Blood in Patients After Skin Burn Injury," Stem Cell Reviews, May 15, 2011 [E Pub ahead of print]. See also, Jiang et al., "Cannabinoid receptor 2 and its agonists mediate hematopoiesis and hematopoietic stem and progenitor cell mobilization," Blood 117:827-838 (2011).

In addition, one may prepare such topical delivery preparation for comprising a cannabinoid receptor binding moiety for wound healing with fibrin, chitosan or other compositions useful as tissue sealants.

Tattoo Removal

Tattoo removal may be via laser ablation in conjunction with an immune modifier (e.g., with Imiquimod), or may be with a tattoo "eraser," to clear pigment. Generally, tattoo removal involves not only removal of pigment, but also generation of immune response to expel the pigment via a wound. Because the present cannabinoid receptor binding agent delivery vehicle may provide additional immune activation through signaling via a cannabinoid receptor, the present invention may be used as an adjunct to tattoo removal.

Anti-Fungal Applications

Because Tinea (sp.) may cause inflammation in the skin, resulting in cracking and suprficial wounding, and subsequent opportunistic infection, one may wish to apply a cannabinoid receptor binding agent delivery vehicle of the present invention to treat, amelioriate, or alleviate such condition. Prophetic compositions include those comprising, consisting of or consisting essentially of:

Table 2 shows a composition for: Localized pain relief (THC) or anti inflammation (CBD) or anti fungal (CBC or CBG) patch.

TABLE 2

| Compound | Concentration |
| --- | --- |
| adhesive | 5-15% |
| ethanol or propylene glycol | 20-30% |
| Tetrahydrocannabinol/Cannabidiol/cannabichromene/cannabigerol | 30-40% |
| phosphatidylcholine or other similar phospholipid | 1-5% |
| nano silica beads/particles/shards/tubes/plates | 1-2% |
| Water | Remainder |

Table 3 shows a composition for: Cannabinoid powder antifungal

TABLE 3

| Compound | Concentration |
| --- | --- |
| zinc oxide | 10-20% |
| cannabinoid of choice(CBG or CBC) | 5-20% |
| Kaolin | 5-20% |
| monoterpene (acyclic, monocyclic, or bicyclic) | 0.5-1% |
| potassium bicarbonate | 10-20% |
| nano silica (optional) | 0.1-2% |

Values vary based on site of powder application, as some areas have more moisture than others Scarring, Fibrosis The present cannabinoid receptor binding delivery vehicle may be used to treat, ameliorate or alleviate dermal fibrosis or conditions associated therewith. Scarring, or fibrosis, may result after inflammation. Cannabinoid receptor signaling is reported to modulate dermal fibrosis. Akhmetshina, A. et al., "The Cannabinoid Receptor CB2 Exerts Antifibrotic Effects in Experimental Dermal Fibrosis," Arthritis & Rheumatism 60:1129-1136 (2009); Garcia-Gonzalez, E. et al., "Cannabinoids inhibit fibrogenesis in diffuse systemic sclerosis fibroblasts," Rheumatology 48:1050-1056 (2009); Balistreri, E. et al., "The cannabinoid WIN55, 212-2 abrogates dermal fibrosis in scleroderma belomycin model," Annals of the Rheumatic Diseases 70: 695-4 (2011).

Pruritus

Itching (pruritus) is generally a symptom associated with skin and other diseases. Generally, because the sensation of "itch" is a product of the central nervous system that communicates with the brain, one can consider that it is really the brain that feels the itch, and not the skin. Cannabinoid receptor CB1 and the vanilloid receptor TRPV1 co localize in sensory neurons and on non-neural cells associated with skin. Co administration of a TRPV1 receptor agonist with a CB1 agonist may act to inhibit itching. EP 1785130 reports (paragraph [0109]) that HU210, reportedly a cannabinoid receptor activating agent, topically applied as described is capable of reducing histamine-induced itch. See generally, review, Paus, R. et al. "Frontiers in pruritus research: scratching the brain for more effective itch therapy," The Journal of Clinical investigation 116: 1174-1185 (2006). Thus, the present invention may be used to treat, ameliorate, or alleviate pruritis.

Some embodiments may include a cannabinoid receptor binding agent, particularly a CB1 receptor agonists, combined with a vanilloid receptor binding agent, such as a TRPV1 agonist, on a solid substrate or in an activated polymeric substrated capable of solidifying in situ. In particular embodiments, the present invention comprises a dermal patch having disposed thereon a cannabinoid receptor binding agent and a vanilloid receptor binding agent, and in other aspects, the cannabinoid receptor binding agent is a CB1 agonist, and the vanilloid receptor binding agent is a TRPV1 agonist. Additional components may include as other known pruritus relief medicaments.

Pigmentation and Hair Growth

Cannabinoid receptor binding agents may use to treat, ameliorate, or alleviate dermatological conditions selected from pigment conditions and hair growth conditions (hair growth follicles being embedded in the skin). See, Magina, S. et al., "Inhibition of basal and ultraviolet B-induced melanogenesis by cannabinoid CB1 receptors: a keratinocyte-dependent effect," Archives of Dermatological Research 303: 201-210 (2011); Telek, A., et al., "Inhibition of human hair follicle growth by endo and exocannabinoids," FASEB 21: 3534-3541 (2007).

Pigmentation

The present cannabinoid receptor binding agent delivery vehicles includes those for treatment, amelioration, or alleviation of pigmentation conditions. Melanogenesis is reportedly inhibited by CB1 receptor activity, presumably in keratinocytes, Magina, S. et al., "Inhibition of basal and ultraviolet B-induced melanogenesis by cannabinoid CB1 receptors: a keratinocyte-dependent effect," Archives of Dermatological Research 303: 201-210 (2011).

Where one wishes melanogenesis inhibition, one may select a cannabinoid receptor agonist (or reverse antagonist), and particularly, a cannabinoid receptor 1 agonist, capable of activating a keratinocyte CB1 receptor. Where one wishes dis-inhibition of melanogenesis, one may select a cannabinoid receptor antagonist (or reverse agonist). One may use a partial agonist (or antagonist) to differ the amplitude of the functional response of receptor activation (or blockage).

Moreover, THC reportedly significantly and dose-dependently suppressed the melanin content of the hair follicle, suggesting THC may also exert inhibitory effects on follicular melanogenesis in situ. Telek, et al., FASEB 21: 3534-3541, cited above. Thus, one may provide a cannabinoid receptor antagonist, or reverse agonist (dis-inhibiting melanogenesis) to provide melanin to hair follicles. The present cannabinoid receptor binding agent delivery vehicle may comprise a cannabinoid receptor antagonist or reverse agonist in an activated polymer substrate to be applied to the scalp, and, upon appropriate activation, deliver the antagonist (or reverse agonist) to the hair follicle to restore melanin production.

Thus, the present invention includes cannabinoid receptor binding agent delivery vehicles for topical delivery comprising a cannabinoid receptor agonist, and in particular embodiments, comprises, consists, or consists essentially of a CB1 receptor agonist capable of activating a CB1 receptor on a keratinocyte of a human subject in need thereof.

Hair Growth

The present invention includes cannabinoid receptor binding compositions and methods for modulating hair growth. The endocannabinoid system is reportedly implicated in the control of human hair growth. See, Telek, A., et al., "Inhibition of human hair follicle growth by endo and exocannabinoids," FASEB 21: 3534-3541 (2007), reporting the endocannabinoid N-arachidonoylethanolamide (anandamide, AEA) as well as the exocannabinoid (9)Δ tetrahydrocannabinol dose-dependently inhibited hair shaft elongation and the proliferation of hair matrix keratinocytes, and induced intraepithelial apoptosis and premature HF regression (catagen).

Thus, the present cannabinoid receptor binding agent compositions and methods may be used to treat a condition selected from among alopecias (such as androgenic, telogen effluvium, alopecia greata, ringworm, scarring alopecia, and hair loss due to cosmetic overprocessing), as well as aesthetic conditions including insufficient hair growth. The present invention thus includes a cannabinoid receptor binding agent for topical delivery for hair growth modulation. In other aspects, the present invention includes a cannabinoid receptor binding agent antagonist on a solid substrate for hair growth promotion. The solid substrate may include nanoparticles enhancing the transmission of the active ingredient through the stratum corneum to the dermis to contact cannabinoid receptors in the hair follicle. If desired, other hair growth modulators, such as minoxidil, may be included.

Because sebaceous and eccrine glands bypass the stratum corneum, this follicular route may be relevant for percutaneous absorption. The opening of the follicular pore, where the hair shaft exits the skin, is relatively large and sebum aids in diffusion of penetrants. An active ingredient may be first partitioned into the sebum, followed by diffusion through the sebum to the lower epidermis. One may use this route for systemic delivery as the vasculature around the hair follicle in the dermis may permit entry into the wider systemic circulation.

In yet other aspects, the present invention includes a cannabinoid receptor binding agent antagonist formulated with a cross-linkable gel, particularly a gel that may be photo cross linked using a predetermined wavelength of light. The gel may contain other moieties, such as water, permeation enhancers, and agents addressing pigment disorders, such as stem cell factor, for example. The present cannabinoid receptor binding agents may be associated with, such as attached to, a nanoparticle. The present embodiment further contemplates a cannabinoid receptor binding agent chemically attached to a nanoparticle and optionally formulated in a crosslinkable gel. The present embodiment contemplates a cannabinoid receptor binding agent chemically attached to a nanoparticle disposed (directly or indirectly, as in a reservoir) on a solid substrate.

Malignancies

The present cannabinoid receptor binding agent delivery vehicle may be used to treat, amelioriate or alleviate abnormal skin growth, including malignancies, such as actinic keratosis, basal cell carcinoma, melanomas, and squamous cell carcinoma.

Cannabinoid receptor binding agents are thought to have anti-proliferative effects, including in the skin. Bíró, T. et al., "The endocannabinoid system of the skin in health and disease: novel perspectives and therapeutic opportunities," Trends in Pharmacologic Sciences, 30:411-420 (2009). Activation of cannabinoid receptors in the skin reportedly selectively resulted in the apoptotic death of tumorigenic epidermal cells (in culture), and in a mouse model. Casanova, M. L. et al., "Inhibition of skin tumor growth and angiogenesis in vivo by activation of cannabinoid receptors," Journal of Clinical Investigation 111:43-50 (2003). Similarly, cannabinoid receptor activation in melanoma cells, melanoma cell lines and in a mouse melanoma model reportedly resulted in decreased growth, proliferation, angiogenesis and metastasis. Blázquez et al., "Cannabinoid receptors as novel targets for the treatment of melanoma," The FASEB Journal 20: 2633-2635 (2009).

The present cannabinoid receptor binding agent delivery vehicles may be comprised of a cannabinoid receptor binding agent and an anti-cancer agent, such as a chemotherapeutic agent or a radiotherapeutic agent. Where one wishes to use only phyto compounds, curcumin is reported to suppress proliferation and induce apoptosis in melanoma cells. Siwak et al., "Curcumin-Induced Antiproliferative and Proapoptotic Effects in Melanoma Cells Are Associated with Suppression of IkB Kinase and Nuclear Factor B Activity and Are Independent of the B-Raf/Mitogen-activated/Extracellular Signal-Regulated Protein Kinase Pathway and the Akt Pathway," Cancer 104: 879-890 (2005).

Thus, in some embodiments, the present invention relates to a cannabinoid receptor binding agent delivery vehicle comprising a cannabinoid receptor binding agent and an anti-cancer agent.

One may further use particles for delivery of the cannabinoid receptor binding agent and optionally the anti-cancer agent. One may, for example prepare a particle having a magnetic core and a functionalized surface to which the cannabinoid receptor binding agent may attach. In this way, a magnetic field could be used to guide the particles to the suitable location. One may further attach an anti-cancer agent to a particle. Albumin or other dispersion compositions may be used. Thus, functionalize magnetic nano particles suitable for transdermal delivery may have a cannabinoid receptor binding agent attached thereto. One may further formulate the functionalized particles having cannabinoid receptor binding agents, as well as albumin or other compositions, within a vesicle, such as a liposome or ethosome, to enhance permeation.

For example, if one prefers phyto-products, one may prepare an extract from *Cannabis* sp. plant material. Such extract may be highly hydrophobic. One may then attach extract moieties to a derivatized particle of suitable size for penetrating the skin. One may further attach curcuminoid or other plant-based curcuminoid anti-proliferative agent. One may then formulate the functionalized nano-particle as above (e.g., in a vesicle, etc.).

One may use a lipid nanoparticle or a polymer nanoparticle similarly, for distribution transdermally to treat, ameliorate, or alleviate a skin cancer condition, such as actinic keratosis, a melanoma, a squamous cell carcinoma, or a basal cell carcinoma.

For cancers below the skin surface, one may use a nanoshell, as described above, particularly for use in converting light energy into heat energy to selectively destroy tumor cells. The light energy may be such wavelength that penetrates the skin. Such nanoshells may be combined with cannabinoid receptor binding agents on the same nanoparticle or where the cannabinoid receptor binding agent is on a separate nanoparticle, such that it is not destroyed by heat. One may further functionalize a nanoparticle, for instance, by attaching a folate molecule thereto that is preferentially bound by tumor cells.

The present invention may be used as a course of anti-cancer therapy, in conjunction with additional anti-cancer agents. One may use, for instance, imiquimod topical cream, in conjunction with the present invention. One may for instance, formulate imiquimod with a cannabinoid receptor binding agent.

Internal Organ Compositions and Methods

The present invention may be used to deliver cannabinoid receptor binding agents locally to a precise location on an internal organ within an animal.

Briefly, the surface of internal organs, such as endothelial cells and tissues, may have cannabinoid receptors that are physiologically responsive upon binding with a cannabinoid receptor binding agent. The present compositions and methods may be used to locally deliver cannabinoid receptor binding agents in suitable quantity and quality for treatment, amelioration or alleviation of particular conditions associated with internal organs.

One may prepare a cannabinoid receptor binding agent on a solid substrate, such as a patch, such that the patch will suitably attach to the internal organ. Various adhesives and other biocompatible materials are known. In some particular embodiments, one may use a dissolvable substrate, such that removal is unnecessary (because the substrate dissolves).

Internal Organ: Liver Inflammation

The present invention may be used to treat, ameliorate or alleviate conditions associated with liver inflammation. The expression of cannabinoid receptors in normal liver is very low, partially because they are not expressed in hepatocytes. However, many studies have demonstrated the up-regulation of the expression of CB1 and CB2 receptors in hepatic myofibroblasts and vascular endothelial cells, as well as increased concentration of endocannabinoids, especially anademide, in liver in the course of chronic progressive liver diseases. Parfieniuk, A. and R. Flisiak, "Role of cannabinoids in chronic liver diseases," Editorial, World Journal of Gastroenterology 14: (2008) See, Pál Pacher and Bin Gao, "Endocannabinoids and Liver Disease. III. Endocannabinoid effects on immune cells: implications for inflammatory liver diseases," American Journal of Physiology, Gastrointestinal and Liver Physiology 294: G850-854 (2008); Hegde, V. L. et al., "Attenuation of Experimental Autoimmune Hepatitis by Exogenous and Endogenous Cannabinoids: Involvement of Regulatory T Cells," Molecular Pharmacology 74:20-33 (2008).

Thus, one may prepare a cannabinoid receptor binding agent delivery vehicle of the present invention suitable for delivery to the surface of the liver. One may prepare a solid substrate, such as a patch, with a suitable adhesive. One may also prepare an injectable activated polymer to be solidified in situ by activation with a suitable reagent, such as photo-crosslinking (light). Such light may be delivered endoscopically.

Internal Organ Pancreas, Islet of Langerhans, Insulin Secretion

The present invention may be used to treat, ameliorate or alleviate conditions associated with insulin secretion. Insulin producing—Islet of Langerhans cells express cannabinoid receptor s, and activation or inhibition of the receptors appears to cross-signal with the insulin receptor. See, Kim, W. et al., "Cannabinoids Inhibit Insulin Receptor Signaling in Pancreatic Beta-Cells: Research Design and Methods," Diabetes 60:1198-1209 (2011); Li, C et al., "Cannabinoid receptor agonists and antagonists stimulate insulin secretion from isolated human islets of Langerhans," Diabetes, Obesity and Metabolism, e-publication May 12, 2011. doi: 10.1111/j.1463-1326.2011.01422.x Thus, the present invention may be used to stimulate insulin secretion. One may, for example, deliver a cannabinoid receptor binding agent delivery vehicle of the present invention to the pancreas to deliver cannabinoid receptor binding agent, such as an agonist (or, antagonist). Such local delivery includes a cannabinoid receptor binding agent composition on a solid substrate suitable for adhering to the surface of the pancreas proximal to islet of Langerhans cells. Such local delivery also includes a cannabinoid receptor binding agent in a polymeric composition capable of solidifying in situ, as described herein. In this way, the present invention contemplates the local delivery of a gel, for instance, to the pancreas, and solidification in situ. Such solidification may be by endoscopic delivery of light in suitable wavelength, for example, if photoactivated crosslinking is used.

Internal Organ Bladder

The present invention may be used to treat, ameliorate or alleviate conditions associated with a bladder condition. Thus, the present invention includes cannabinoid receptor binding agent compositions and methods for local delivery on the bladder. Such local delivery includes a cannabinoid receptor binding agent composition on a solid substrate suitable for adhering to the surface of the bladder or urethral inner or outer surfaces. Such local delivery also includes a cannabinoid receptor binding agent in a polymeric composition capable of solidifying in situ, as described herein. In this way, the present invention contemplates the local delivery of a gel, for instance, to the bladder, and solidification in situ. Such solidification may be by endoscopic delivery of light in suitable wavelength, for example, if photoactivated crosslinking is used.

Briefly, in the bladder, activation of CB1 receptors in the urinary bladder is reported to reduce symptoms related to inflammation. Walczak, J-S., and F. Cervero, "Local activation of cannabinoid CB1 receptors in the urinary bladder reduces the inflammation-induced sensitization of bladder afferents," Molecular Pain 7:31 (2011). Moreover, for conditions involving bladder obstruction, a cannabinoid receptor binding agent is reported to improve bladder emptying in rats with a partial urethral obstruction. Gratzke C. et al., "Cannabinor, a selective cannabinoid −2 receptor agonist improves bladder emptying in rats with partial urethral obstruction," J. Urology 185:731-736 (2011).

Internal Organ: Heart and Cardiovascular

The present invention may be used to treat, ameliorate or alleviate cardiovascular conditions, including tissue damage from heart attacks, or blocked arteries. See, Hiley, R. C., "Endocannabinoids and the Heart," Journal of Cardiovascular Pharmacology, Author manuscript; available in PMC 2009 Oct. 1, published in final edited form as: Journal of Cardiovascular Pharmacology 53: 267-275 (2009); Montecucco F. et al., "CB(2) cannabinoid receptor activation is cardioprotective in a mouse model of ischemia/reperfusion,"

Journal of Molecular Cell Cardiology 46:612-620 (2009). Activation of the CB2 receptor, directly or indirectly, is reported to have cardioprotective effects. (Id.) Thus, the present invention relates to the compositions comprising and methods of using a cannabinoid receptor agonist for cardioprotective therapy.

Moreover, while not wishing to be bound by theory, there are reports that cannabinoid receptor 2 and its agonists mobilize stem cells, e.g., Jiang et al., "Cannabinoid receptor 2 and its agonists mediate hematopoiesis and hematopoietic stem and progenitor cell mobilization," Blood 117:827-838 (2011). As local resident cardiac stem cells may be found in the heart, such stem cells may be recruited for local repair of damaged tissue.

A cannabinoid receptor binding agent may be disposed on a solid substrate. One may, for instance, prepare a cannabinoid receptor binding agent on a vascular stent to ameliorate cardiovascular conditions. One may prepare a cannabinoid receptor binding agent on a solid substrate, such as a patch, to administer to damaged cardiac tissues.

One may, further, prepare a cannabinoid receptor binding agent in an injectable polymeric composition that may be photoactivatable for crosslinking by, for instance, ultraviolet light. One may use arthroscopic or other means to deliver the ultraviolet light or other appropriate cross linking agent on to the desired tissue (e.g., heart or vasculature). One may also include suitable cells (such as stem or pluripotent cells), analgesics, anesthetic, antibacterials, and other therapeutic medicaments in such gel (or disposed on such solid substrate).

For procedures involving anastomosis, such as for blood vessels, and also areas of the gastrointestinal tract, urinary tract and microsurgical techniques (e.g., tubal ligation or vasectomy), one may embed a cannabinoid receptor binding agent at the site where the hollow organs join, such as in a biological glue or coating a surgical staple.

Fertilization Treatment and Reproductive Organs

The present prophetic example relates to the relevance of the endocannabinoids system as relevant to reproduction and fertility. Therefore, the present invention relates to topical delivery of a cannabinoid receptor binding agent on the reproductive organ surface.

The endocannabinoid system as it relates to fertility and reproduction is the subject of much study, and cannabinoid receptor binding plays a role. Although excess intake of cannabinoids is reported to have adverse reproductive effects, the endocannabiniod system reportedly has modulating effects on gamete production and quality, fertilization, embryo implantation and development. See, e.g., review, Wang, H., Dey, S. K, and Maccarrone, M., "Jekyll and Hyde: Two Faces of Cannabinoid Signaling in Male and Female Fertility," Endocrine Reviews 27: 427-448 (2006); Sun et al, "Endocannabiniod signaling directs differentiation of trophoblast cell lineages and placentation," PNAS-USA 107:16887-16892 (2010); El-Talatini M. R., et al. Localisation and Function of the Endocannabiniod System in the Human Ovary. PLoS ONE 4(2): e45799 (2009); Gervasi, M. G. et al. "Anandamide Capacitates Bull Spermatozoa through CB1 and TRPV1 Activation," PLoS ONE 6(2): e16993. (2011).

The present invention provides topical delivery of a cannabinoid receptor binding agent disposed on a solid substrate, such as a patch or bandage, within the oviduct, vagina or ultimately uterus and placenta. Adhesion, such as mucoadhesion, may localize the solid substrate to mucosal surfaces. Intra-vaginal/oviduct delivery also includes vaginal suppositories (also referred to as pessaries or ovules), tablets, creams, ointments, gels, foams, films, medicated tampons, sponges and diaphragms. Additional moieties that may be included, depending on the purpose, are those useful for birth control (e.g., spermicides) as well as those useful for controlling infectious disease (anti-viral and anti-bacterial agents). A cannabinoid receptor binding agent that is an antagonist may be used in conjunction with pregnancy, to prevent harm to the fetus from maternal deleterious THC ingestion.

The present invention also contemplates methods for enhancing sperm fertilization prior to in vitro fertilization. Blocking the CB1 receptor with the cannabinoid receptor binding agent SR141716 (USAN:rimonabant) is reported to enhance sperm motility. Aquilia et al., "Rimonabant (SR141716) induces metabolism and acquisition of fertilizing ability in human sperm," British Journal of Pharmacology 159: 831-841 (2010). On the other hand, activating the CB1 and vanilloid receptors on the sperm surface are reported to play a role in modifying the sperm cell surface so as to enhance fertilization capacity, at least in bovines. Gervasi, M. G. et al. Anandamide Capacitates Bull Spermatozoa through CB1 and TRPV1 Activation. PLoS ONE 6(2): e16993. (2011). Thus the present invention includes using cannabinoid receptor binding agents that agonize a cannabinoid receptor, as well as those that antagonize a cannabinoid receptor. The present methods and compositions include using these agents simultaneously, or in seriatim.

Such cannabinoid receptor binding agent as described could be localized to a solid surface (e.g., dispersed within a solid substrate that is adhered to a solid surface of a container, such as a petri dish), or dispersed throughout a solution containing the sperm to be treated. Sperm may be pre- or post-selected, such as by motility, and microfluidic devices and techniques may be used.

Ophthalmic Conditions

The present invention contemplates the use of cannabinoid receptor binding agents to treat, ameliorate or alleviate eye disorders. CB1 and TRPV1 activation are reported to be instrumental in eliciting wound healing in human corneal epithelial cells. See, Yang et al, "Epidermal growth factor receptor transactivation by the cannabinoid receptor (CB1) and transient receptor potential vanilloid 1 (TRPV1) induces differential responses in corneal epithelial cells," Experimental Eye Research 91: 462-471 (2010). Thus, a liquid formulation comprising a cannabinoid receptor binding agent, including a cannabinoid receptor binding agent agonist for epithelial CB1 receptors in the eye, is contemplated herein.

The present cannabinoid receptor binding agent delivery vehicle may be formulated as an eye drop. Another alternative may be to prepare an eye covering substrate, such as an ocular lens, such as a contact lens.

Also contemplated is localized delivery for ocular purposes, for instance, as a moiety in ocular bandages. For example, U.S. Pat. No. 5,024,742, Nesburn et al., "Method of Crosslinking Amino Acid Containing Polymers Using Photoactivatable Chemical Crosslinkers" (1991) reports forming highly crosslinked amino acid-containing polymers (such as collagen) in situ using photo activated cross linking agents. E.g., Col. 7, lines 9-19. Suitable polymeric compositions may applied to the eye in liquid form, and then solidified (fully or partially) by, for instance, crosslinking, such as with a crosslinking agent, such as a photoactivated crosslinking agent. Polymeric eye coverings solidified in situ protect the eye during wound healing, for instance, and may be formulated to hydrate they eye, such as by using polymeric hydrogel material including water.

As indicated above, other agents may be included such formulations for alkali burns, anti-allergic compositions, antibiotic compositions, antibiotics with steroids, anti-fungals, anti-inflammatory NSAIDS, anti-inflammatory steroids, artificial tears, astringents, local anesthetics, mydriatics and cycloplegics. The present cannabinoid receptor binding agent delivery vehicles may be prepared as a retinal product, for gonioscopic examinations, or as cataract surgical products, for example.

The present compositions may be used as a method of treating, ameliorating, or alleviating eye conditions incident to eye conditions, such as dry eye, allergic reactions or injury due to frictional materials, and eye surgeries (such as corneal transplants, or laser eye surgery (such as LASIK procedures)), wounds from surgeries for various cancers (carcinomas, melanomas, blastomas). Numerous other ophthalmic conditions will be apparent to those of skill in the art.

Musculo-Skeletal: Bone Conditions

The present invention contemplates the use of cannabinoid receptor binding agents to treat, ameliorate or alleviate bone conditions, such as osteoporosis. Bone is maintained in dynamic equilibrium by bone growth (predominantly osteoblasts) and bone degradation (predominantly osteoclasts). Recent studies report the involvement of endocannabinoids and their receptors in skeletal bone growth and resorption. See, review, Idris, A. I., "Cannabinoid receptors as target for treatment of osteoporosis: a tale of two therapies," Current Neuropharmacology 8:243-253 (2010). While the timing and duration of cannabinoid receptor effects on bone remodeling vis-à-vis osteoblastic/osteoclast activity is not fully understood, the present invention encompasses, in some aspects, a solid substrate biocompatible with bone comprising a cannabinoid receptor binding agent. The solid substrate may contain hydroxylapatite or other suitable polymeric scaffolding to encourage support of bone growth.

Bone remodeling may be incident to osteoporosis, as well as osteoarthritis, and bone metastatic conditions. Additional bone remodeling therapeutic agents, such as those affecting RANK, RANK-ligand, and osteoprotogerin, such as denosomab, may be co-administered simultaneously, or in seriatim.

In addition to bone remodeling, the present invention may be beneficial as an adjunct to bone prosthetic devices. One of the drawbacks of a metallic prosthetic (hip, knee, or other prosthetic) is that, over time, wear produces particles, and frequently deleterious particle induced inflammation. Reportedly, a cannabinoid receptor selective antagonist inhibited titanium particle induced inflammatory reaction by reducing pro-inflammatory cytokines in vitro and in vivo. Zhou, F. et al, "Effects of a cannabinoid receptor 2 selective antagonist on the inflammatory reaction to titanium particles in vivo and in vitro," Journal of International Medical Research 38:2023-32 (2010); Geng et al., "Protection against titanium particle induced osteolysis by cannabinoid receptor 2 selective antagonist," Biomaterials, 31:1996-2000 (2010). The present invention, in yet other aspects, includes a method of inhibiting inflammation resulting from particle induced inflammation from wear of prosthetic implant by providing a cannabinoid receptor 2 antagonist to the site of inflammation. More particularly, the present invention includes a prosthetic implant having a surface coating containing a cannabinoid receptor 2 antagonist. One may apply a cannabinoid receptor binding agent to a prosthetic in situ, particularly by the presently provided solid substrate, such as a patch, or by local delivery of a gel to be solidified in situ, for instance. Thus, the present invention provides for a prosthetic comprising a cannabinoid receptor binding agent, and related methods and compositions.

Musculo-Skeletal: Muscle Tissue Conditions

The present invention, in some embodiments, may be used to treat, amelioriate, or alleviate conditions associated with muscle tissue. In particular, one may apply the present cannabinoid receptor binding agent compositions topically to permit delivery through the dermis to the tissue below. Cannabinoid receptor binding agents adsorbed, chemically attached to, or encapsulated in nanotubes may penetrate below the dermis for delivery to the deeper muscle tissue. In particular, one may prepare a substrate comprising such cannabinoid receptor binding agent and nanotube composition, in the form of a glove, sock, wrap, etc. such that the wearer has continual delivery of a cannabinoid receptor binding agent. One may further chemically modify the binding agent such that Internal Organ Mucosal Immune Conditions One may prepare a solid substrate for adhesion to a mucosal region for delivery of a cannabinoid receptor binding agent through a mucosal region to a desired location.

For example, one may seek to prepare a cannabinoid receptor binding agent as a nasal patch comprising a cannabinoid receptor binding agent for delivery into the brain. One may prepare a dissolvable nasal patch with the compositions and methods described herein. One contemplated embodiment is a cannabinoid receptor binding agent nasal patch comprising, consisting of or consisting essentially of chitosan or a related composition. The nasal patch may comprise a cannabinoid receptor binding agent within a vesicle, such as a liposome or ethosome. The cannabinoid receptor binding agent may be associated with or attached to a nanoparticle, and that composition may optionally be within a vesicle as described. One may also prepare a nose drop or spray capable of solidifying in situ within the nose.

Intestinal tract disorders may be treated, ameliorated or alleviated by the use of a cannabinoid receptor binding agent. De Sabatino, A. et al., The endogenous cannabinoid system in the gut of patients with inflammatory bowel disease, Mucosal Immunity," doi: 10.1038/mi.2011.18 (advance publication, April 2011); Marquez L., et al., "Ulcerative coitis induces changes on the expression of the endocannabinoids system in the human colonic tissue," PLoS One 4:36893 (2009).

In addition, mucosal immunity has a variety of components. Transferrins, such as lactoferrin, are found in milk and mucosal secretions and are thought to be instrumental in such mucosal immunological systems. Lactoferrin, for instance, may have anti-viral or anti-microbial properties. Such transferrins may be used in the present compositions and methods.

Thus, one may prepare a composition comprising a cannabinoid receptor binding agent and a mucosal adhesive for the treatment of an intestinal disorder, such as colitis. The topical delivery system may comprise a patch, and the patch may optionally have a cannabinoid binding agent active ingredient disposed in a reservoir or in a matrix.

The above applications are not intended to limit the scope of the present invention, and are presented for illustrative purposes.

WORKING EXAMPLES

Psoriasis Treatment

Ten grams of purified cannabidiol (CBD) was obtained through extraction of plant material. Purification was achieved using a rotary evaporator (IKA, RC-10). Raw extract was combined with 10 grams of isopropyl alcohol, 4 grams of Henkel Duro-Tak transdermal adhesive, 1.5 grams raw nanocrystalline cellulose, and 1.5 grams of PEGylated nanocrystalline cellulose (NCC) to make a slurry. The slurry was then homogenized using an IKA Homogenizer. Homogenized preparation was sonicated at 400 W for 60 seconds. The final preparation was placed in a syringe for storage/usage.

Patch samples were prepared by applying 10 ml of final preparation to 3M Scotchpak® polyester backing film and grading it to form a 100 micron layer using a Gradco Gardner blade. Film was then dried at 150 C for 180 seconds. An acrylic backing layer was then applied for storage of completed nanocrystalline cellulose enhanced transdermal cannabinoid receptor patch.

In a second embodiment, ten grams of purified CBD was obtained through extraction of plant material and purification was achieved using a rotary evaporator (IKA, RC-10). Raw extract was combined with 10 grams of isopropyl alcohol, 4 grams of Henkel Duro-Tak transdermal adhesive, and 4.5 grams of PEGylated silica nano powder 5-15 nm (Sigma) to make a slurry. The slurry was then homogenized using an IKA Homogenizer.

Patch samples were prepared by applying 10 ml of final preparation to 3M Scotchpak® polyester backing film and grading it to form a 100 micron layer using a Gradco Gardner blade. Film was then dried at 150 C for 180 seconds. An acrylic backing layer was then applied for storage of completed Nano silica enhanced transdermal cannabinoid receptor patch.

Figure 6A:
FIGS. 6A-C are photographs of a patient with psoriasis.
Figure 6B:
Figure 6C:

A test subject with moderate psoriasis (FIGS. 6A-6C) was used to test the difference between a control of no patch (control patch), a standard patch containing CBD as the active ingredient (standard patch), a control patch without an active (non-active patch), and a patch with CBD as the active and enhanced with various methods of bio compatible nano-particulate compounds (nano-enhanced patch). An Ocean Optics Jazz Spectrophotometer was used to quantify the reduction of inflammation to the affected area before and after each treatment at a standardized distance of 1 cm.

A 2 cm×4 cm patch was applied to affected areas on 12 different locations on the body, 3 for each test group. Sample data was taken and used as baseline. Patches were left on the test subject for 6 hours to show the difference in effect of each patch in relation to time.

Figure 7A:
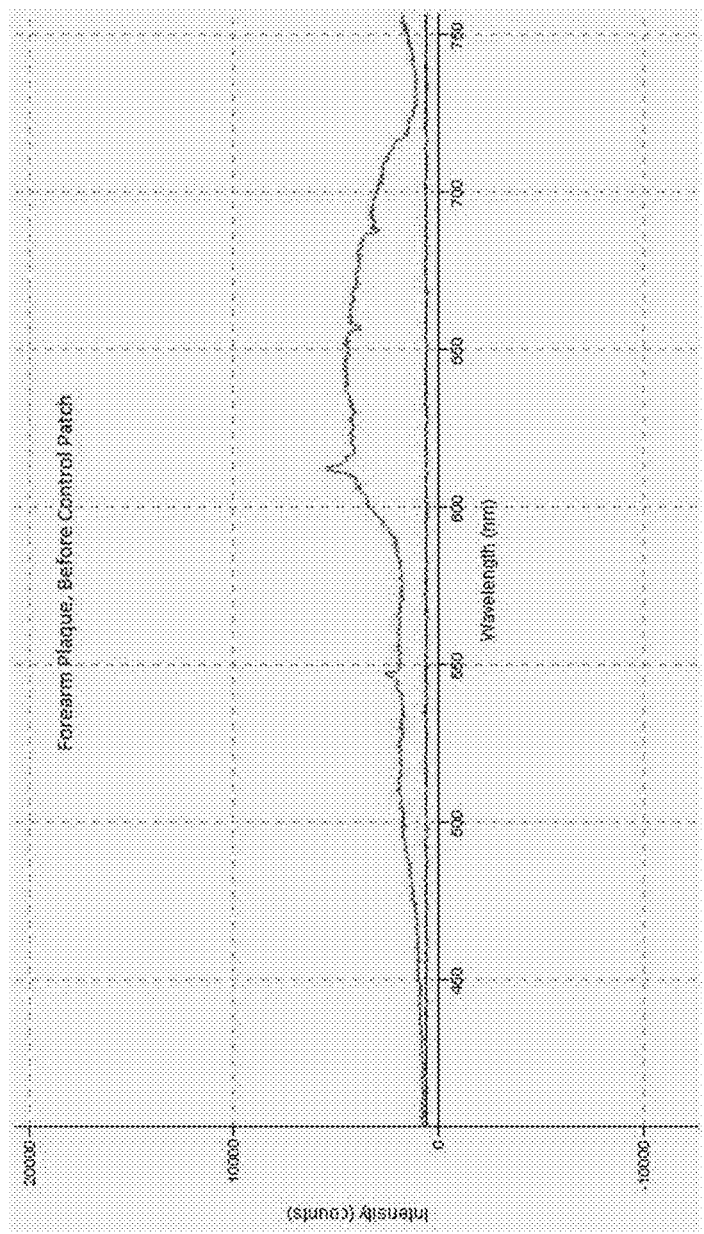
FIGS. 7A and 7B are graphs of spectrophotometric data of an affected area of the skin of a patient before and after treatment with a control patch.
Figure 7B:
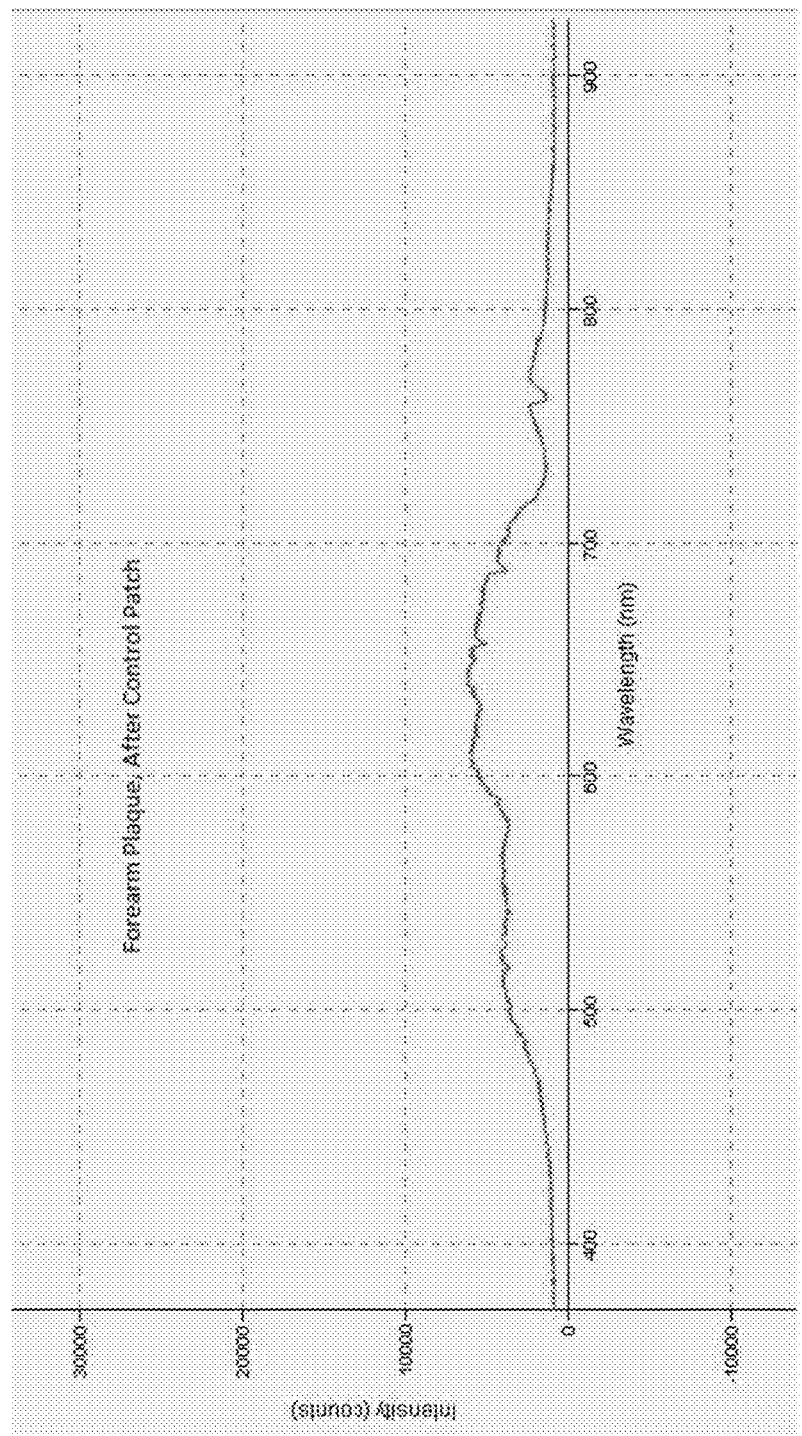
Figure 8A:
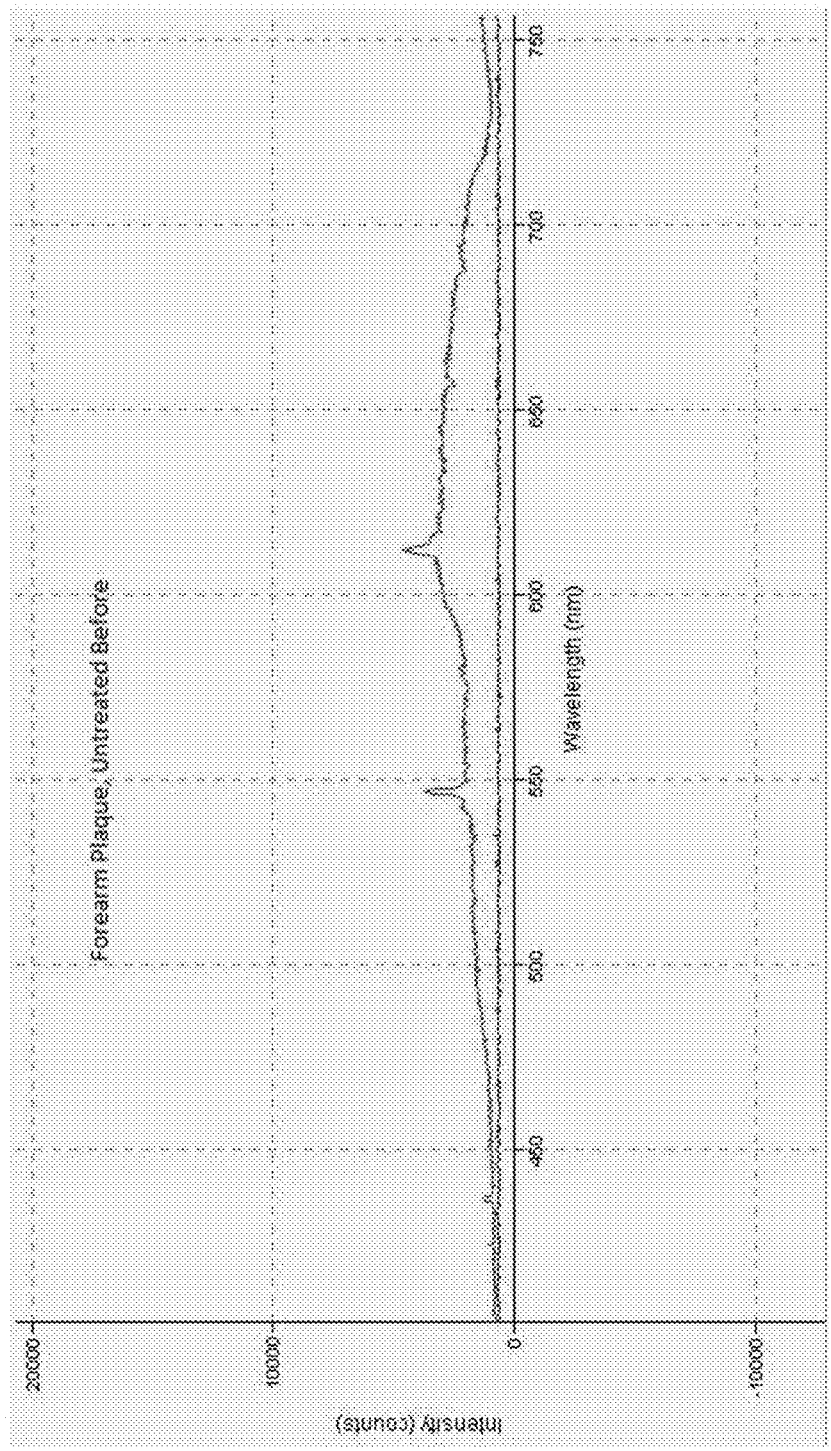
FIGS. 8A and 8B are graphs of spectrophotometric data of an affected area of the skin of the patient before and after the other affected areas were treated.
Figure 8B:
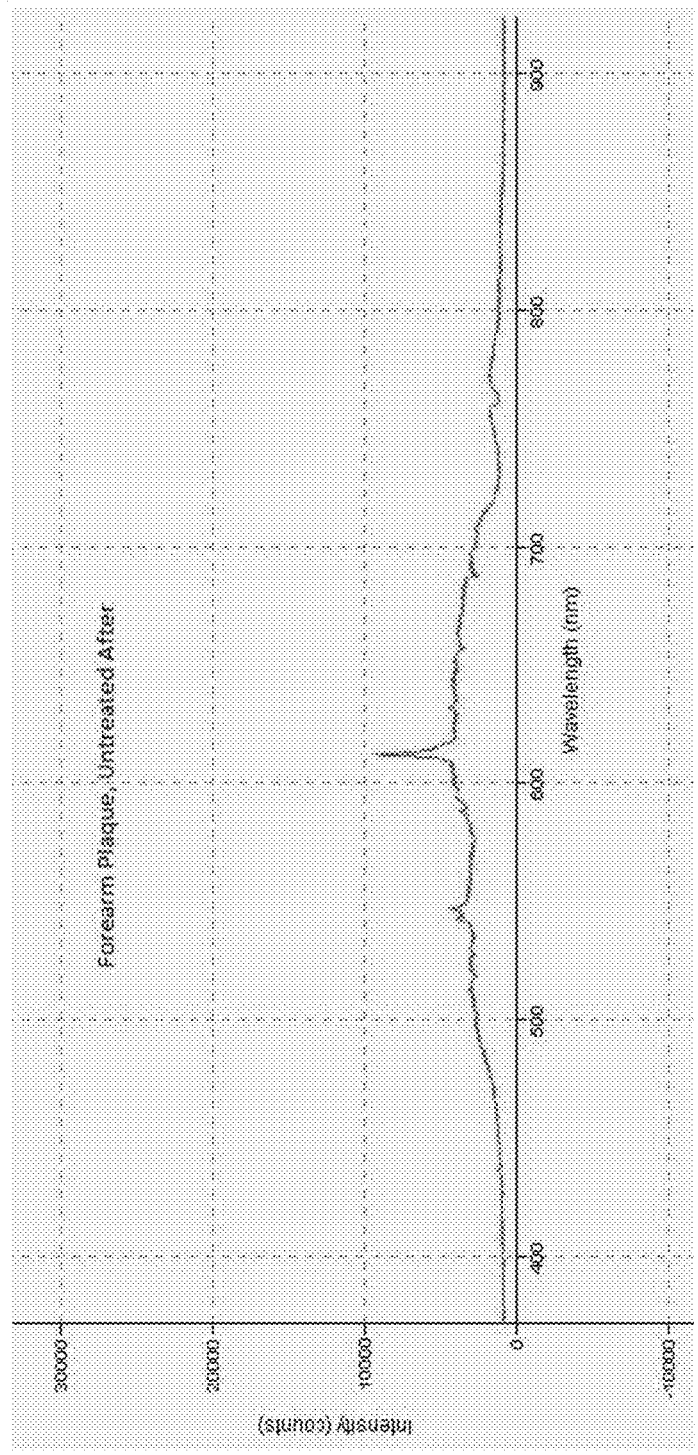

Localized inflammation reduction was present on the standard and nano-enhanced patches. Pictographic and spectrographic data of the treated regions supporting these results are shown in FIGS. 7A-11B. In regards to the control regions and non-active patches, it is apparent that there was really no change., As shown in FIGS. 7A and 7B, there was no noticeable changes in the peaks before and after the treatment of control (non-active) patches. Similarly, the forearm locations that went untreated also showed no change as shown in FIGS. 8A and 8B.

Figure 9A:
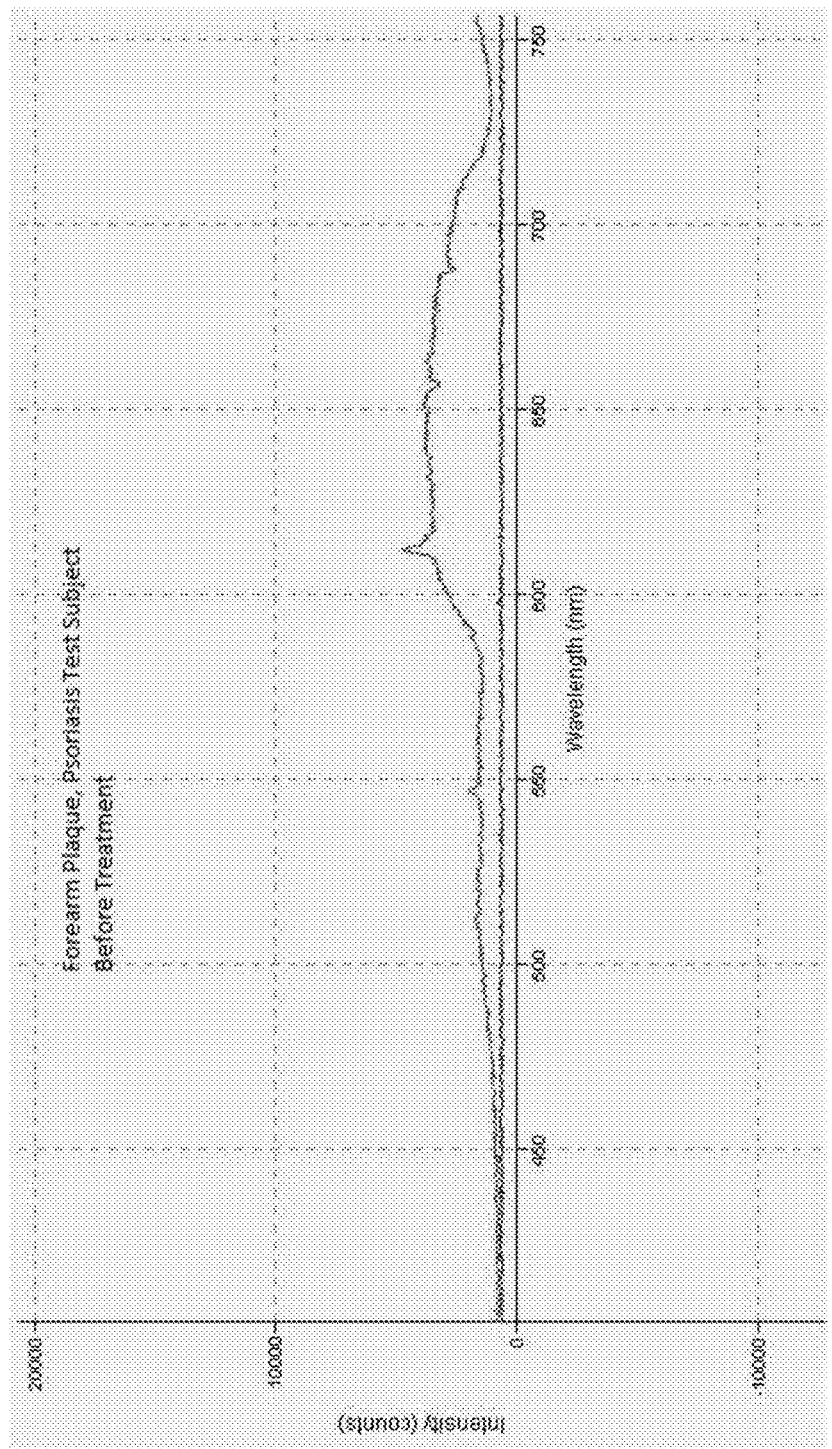
FIGS. 9A and 9B are graphs of spectrophotometric data of an affected area of the skin of the patient before and after treatment with a standard patch.
Figure 9B:
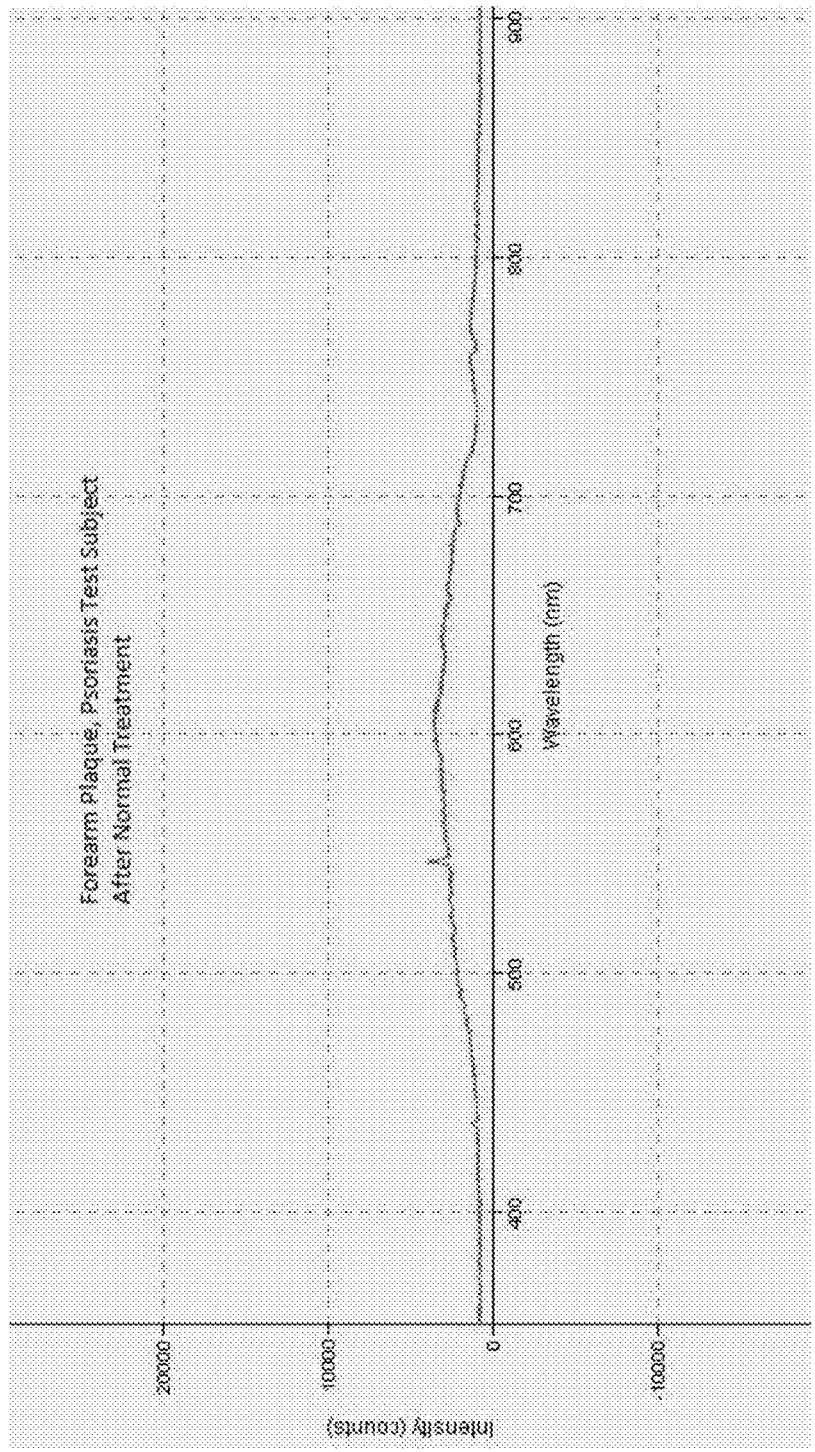
Figure 10A:
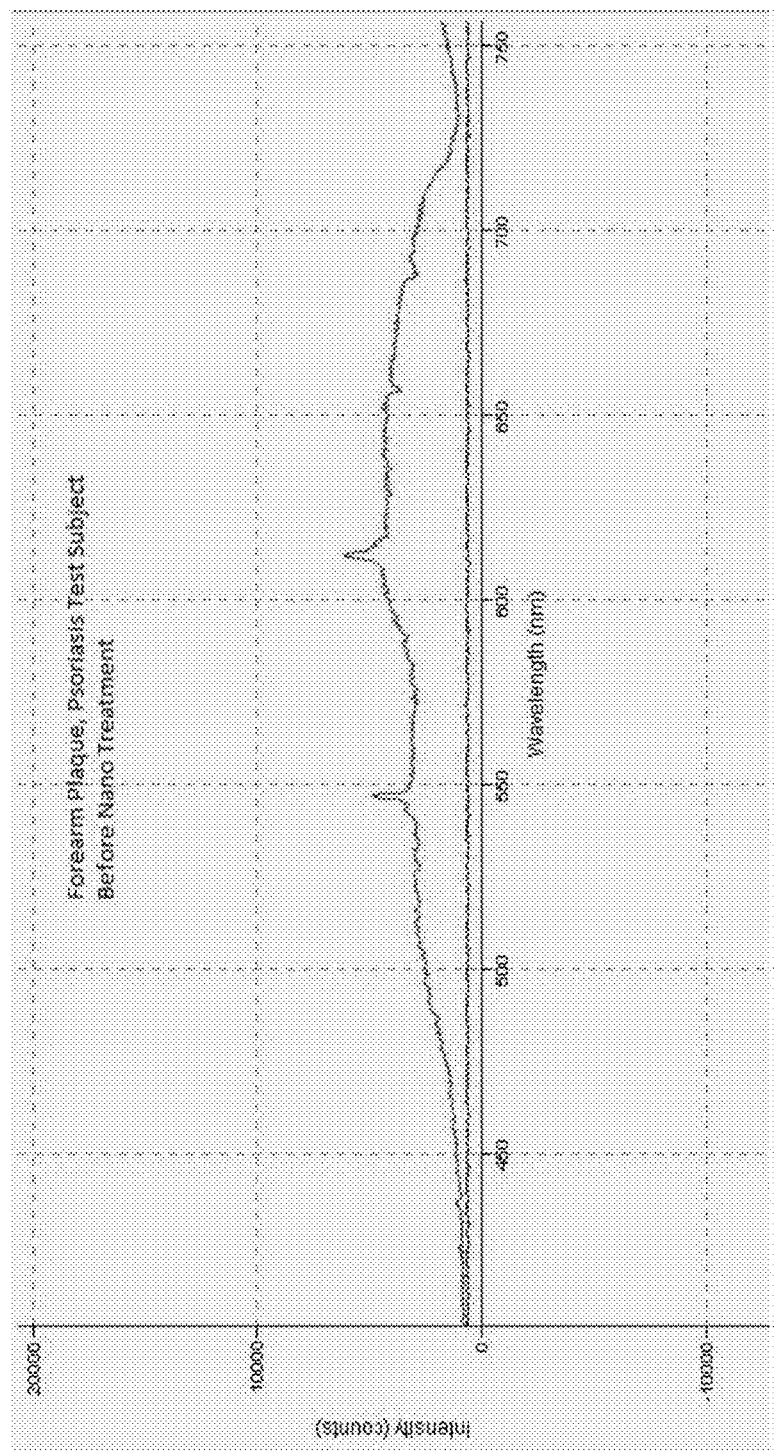
FIGS. 10A and 10B are graphs of spectrophotometric data of an affected area of the skin of the patient before and after treatment with a nano-enhanced patch.
Figure 10B:
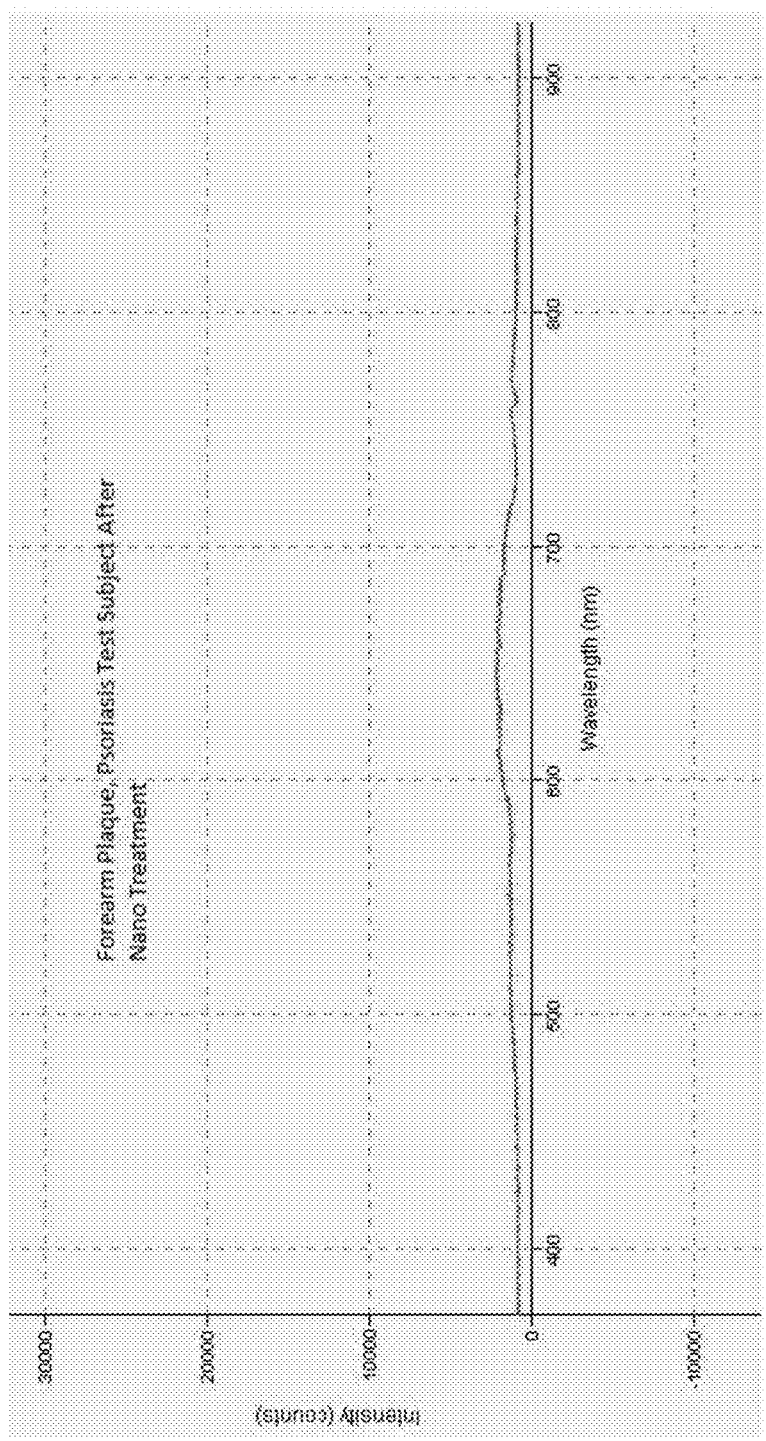
Figure 11A:
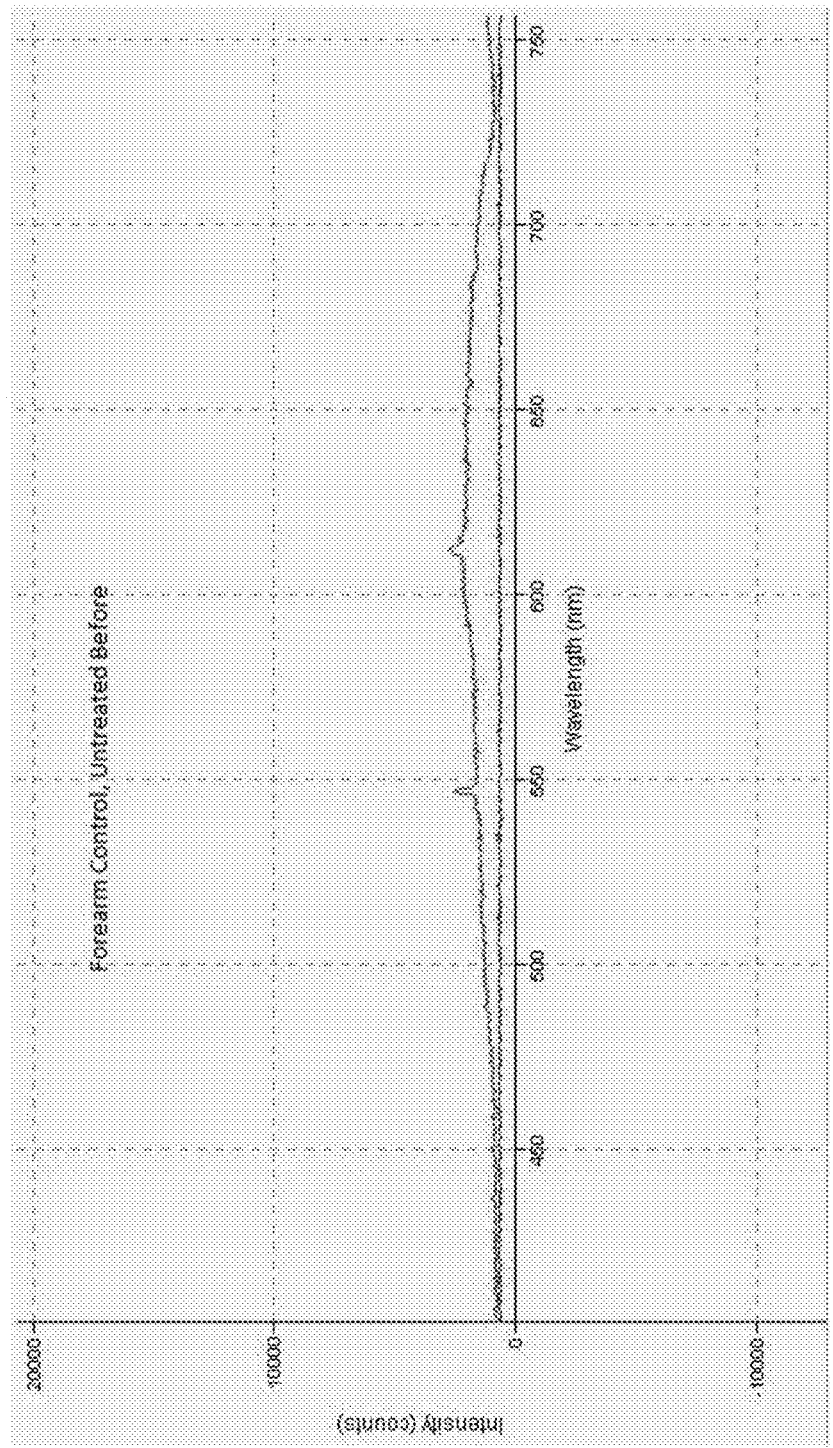
FIGS. 11A and 11B are graphs of spectrophotometric data of an unaffected area of the skin of the patient before and after the affected areas were treated.
Figure 11B:
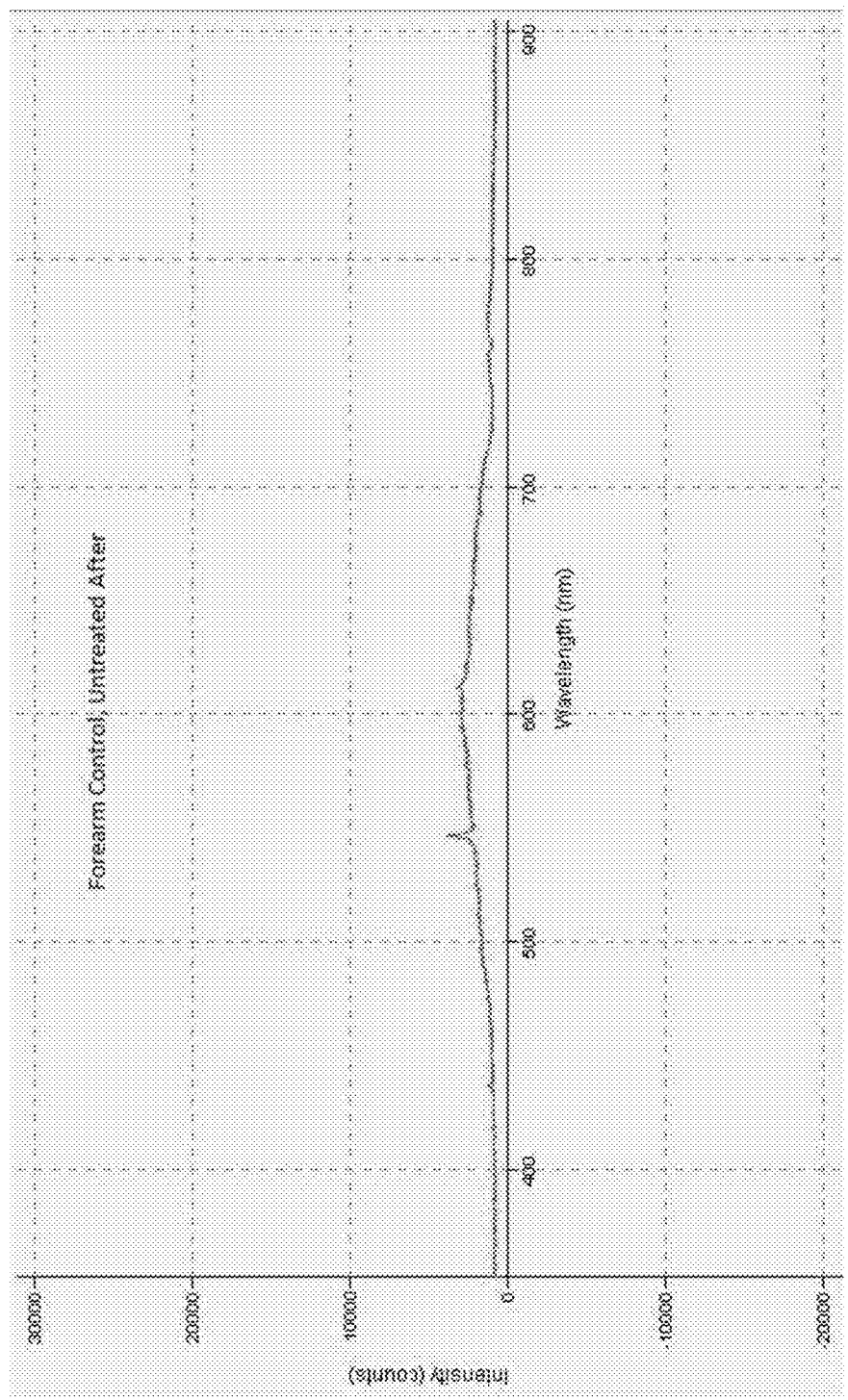

On the other hand, there was an effect from the standard cannabinoid receptor patch. As shown in FIGS. 9A and 9B, after the treatment, the spectrum shifted more into the yellow region (530-600 nm) indicating that there was some reduction in the redness of the skin from the standard patch group. What is most noticeable is that the nanocrystalline cellulose enhanced patches, not only resulted in a shift toward the yellow region but also reduced the overall intensity of color produced as shown in FIGS. 10A and 10B. Without being bound by theory, this could mean that due to the size of the nanocrystal (10×100 nm), the crystals could have inhibited the production of lipocortins, resulting in a limited production of arachidonic acid. What this really means is that the nanoparticles could have a synergistic effect not because of chemical interactions but because of physical inhibition (nanoparticles clogging up protein production by binding to various portions of the protein). Proteins are known for being quite large and can be affected by many things, including steroids that affect cells chemically. A control region without any psoriasis did not show any significant changes during the study as shown in FIGS. 11A and 11B.

Burn Treatment

Figure 12A:
FIGS. 12A and 12B are photographs of a patient suffering second-degree burns before and after treatment.
Figure 12B:

An enthusiastic test subject volunteered to sustain 2 moderate second degree burns to the forearm (see FIGS. 12A and 12B) to test the difference between a Nanomaterial enhanced patch and a standard patch. A control area of skin was used to test a standard patch for irritation. An Ocean Optics Jazz Spectrophotometer was used to quantify the reduction of inflammation to the affected area before and after each treatment at a standardized distance of 1 cm.

A 2 cm×4 cm patch was applied to affected areas on 3 different locations on the forearm, a second degree burn, a control section of skin, and another burn as unenhanced. Patches were left on the test subject for 6 hours to show the difference in effect of each patch in relation to time.

Figure 13A:
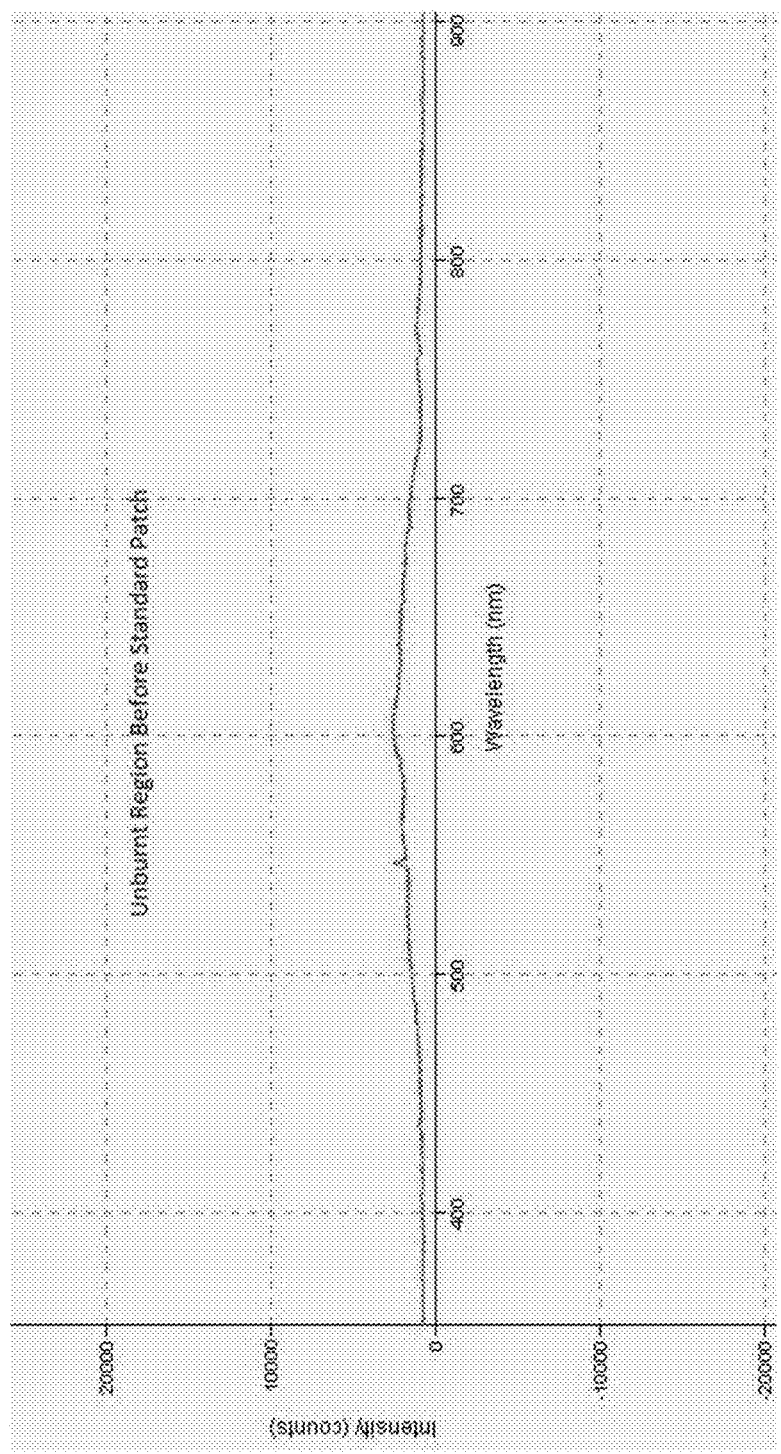
FIGS. 13A and 13B are graphs of spectrophotometric data of an unburnt area before and after treatment with a standard patch.
Figure 13B:
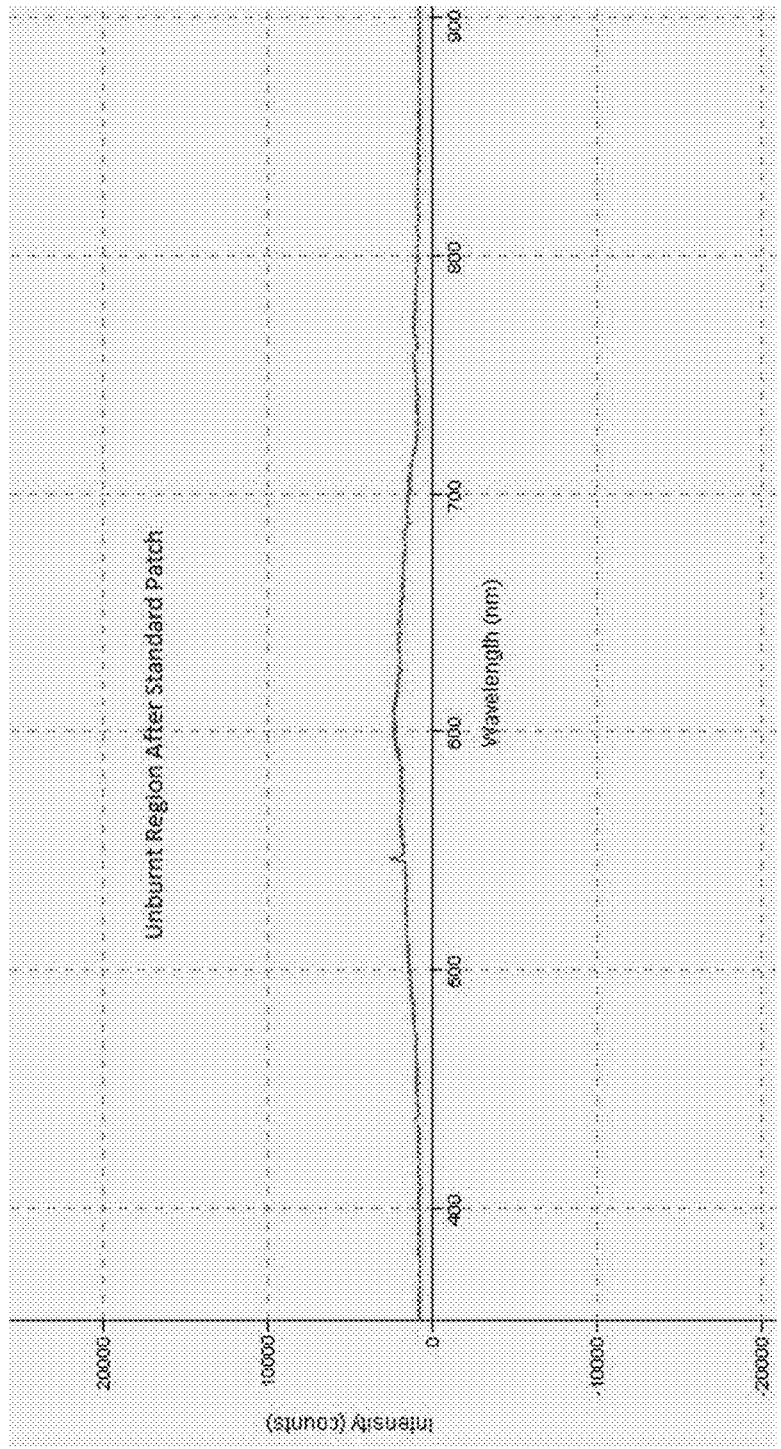
Figure 14A:
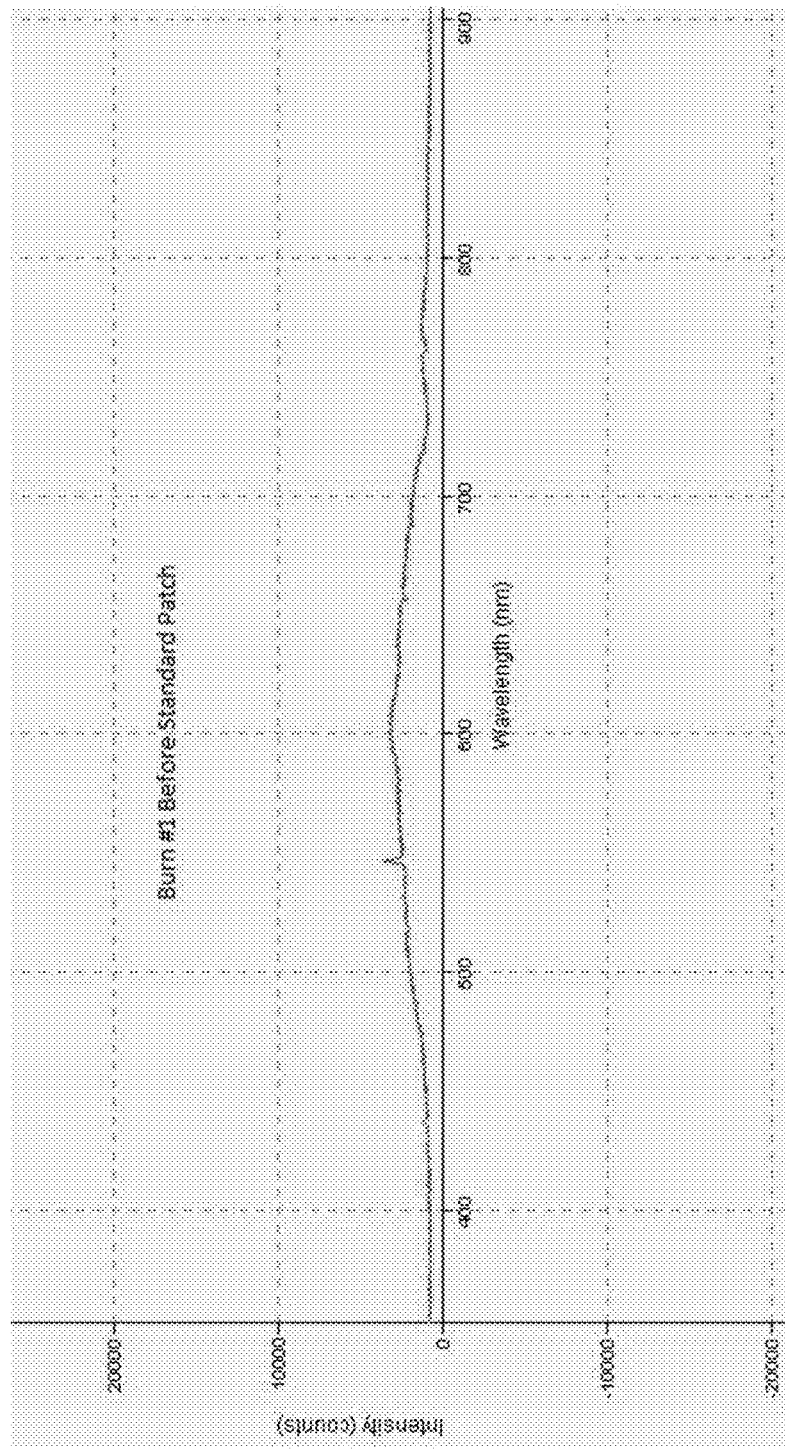
FIGS. 14A and 14B are graphs of spectrophotometric data of a burnt area before and after treatment with a standard patch.
Figure 14B:
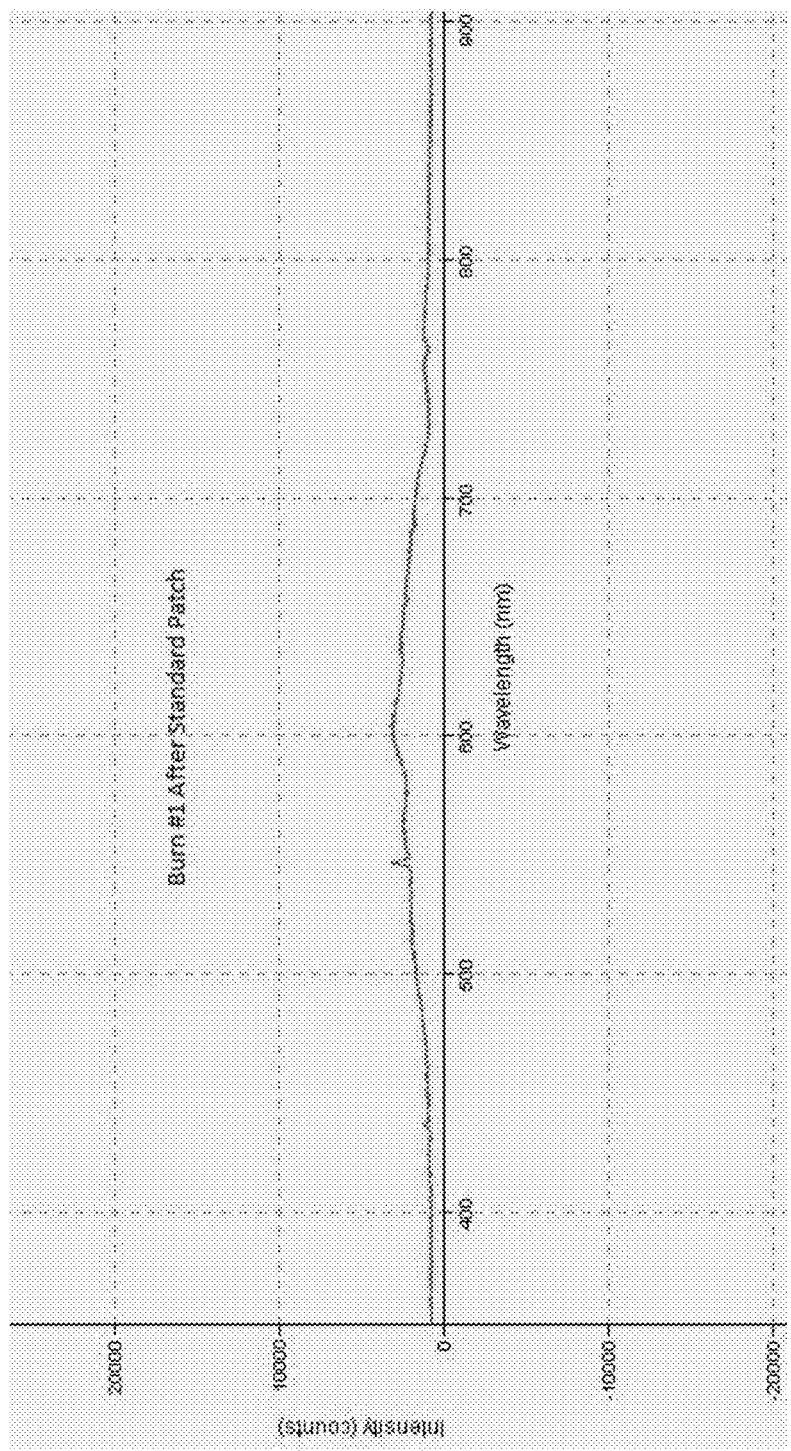
Figure 15A:
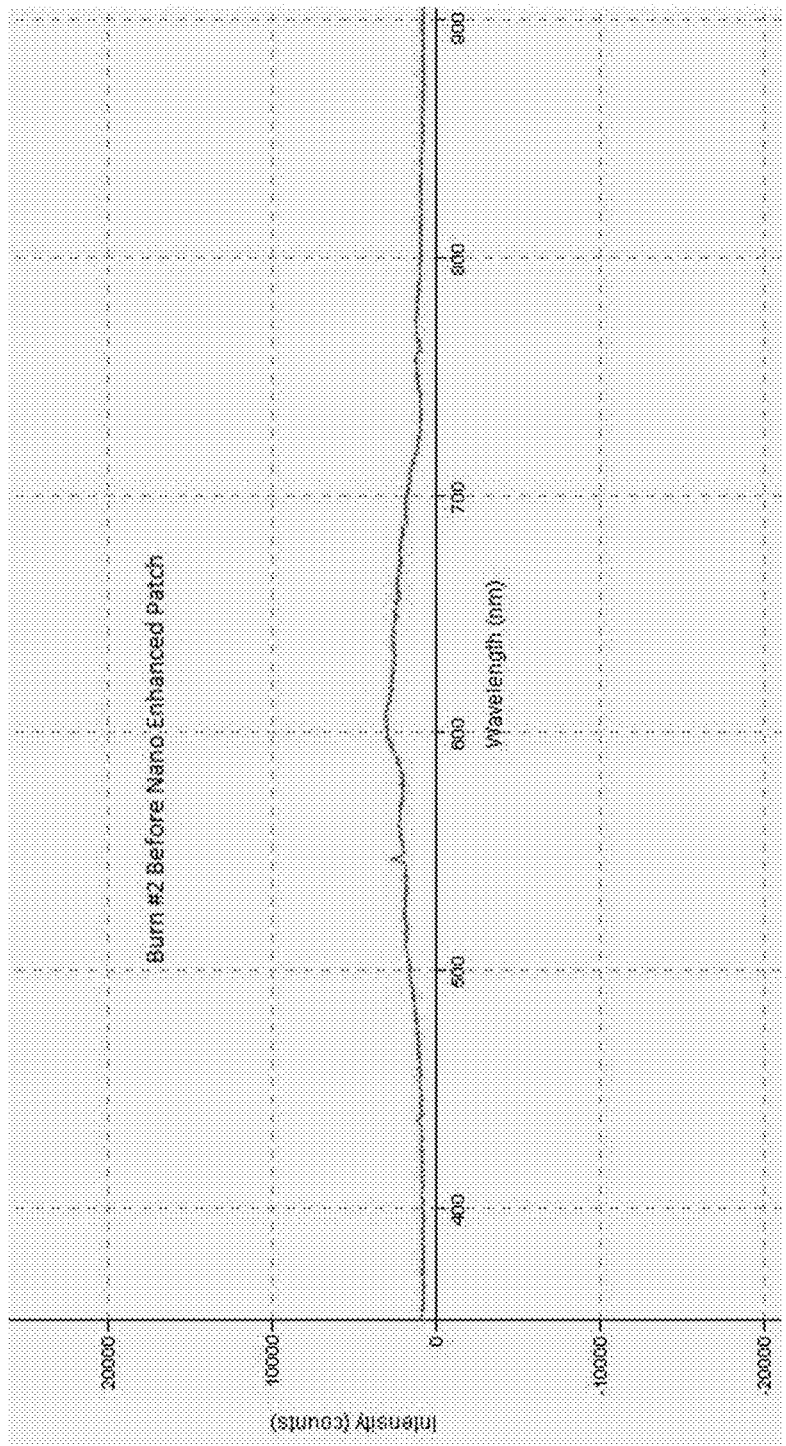
FIGS. 15A and 15B are graphs of spectrophotometric data of a burnt area before and after treatment with a nano-enhanced patch.
Figure 15B:
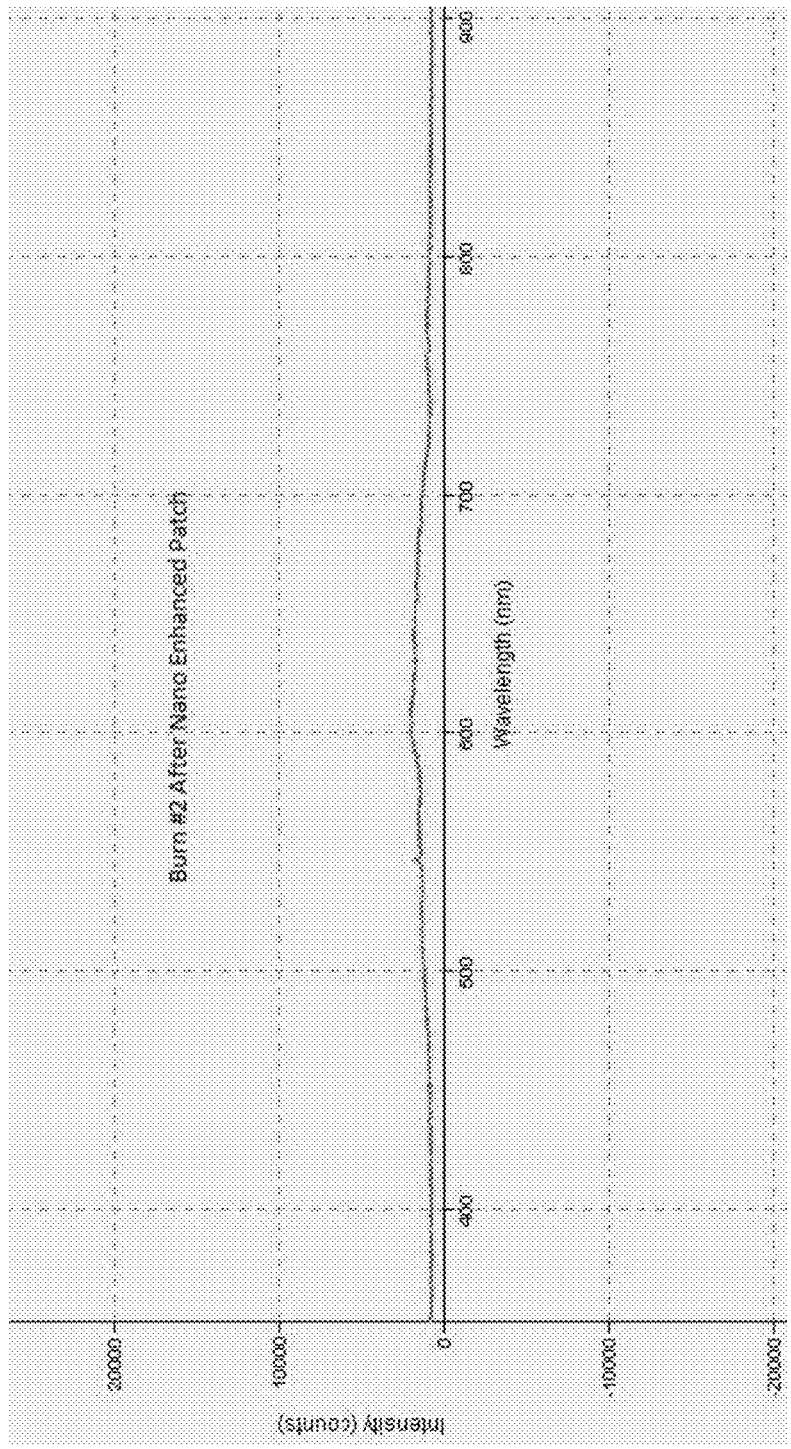

Burn results show that the area exposed to the standard patch treatment was not as effective as area treated with the nano-enhanced patch as shown in FIGS. 13A-13B There was a favorable response to the standard patches at the sites of the burns; however, a large variance was noticed with the nanocrystalline cellulose enhanced patch.

Initially the nanocrystalline cellulose was intended as an excipient/flux enhancer; however, it seemed to reduce not only redness and color but the visible swelling of the burn as well. There was also an unexpected result that had never been seen before. As time elapsed on a patients arm there was a noticeable change in healing time compared to the other variants tested. The nanocrystalline cellulose, a strong nano sized crystal, could have possible been acting as a scaffold for skin regrowth, coupled with the anti-inflammatory effect of the cannabinoid receptor modifier it resulted in the skin healing itself at double the rate of the non-active treated burn! This is a never before seen reaction using cannabinoids and could be directly applicable to severe burn victims as the only effect of the active is as a localized anti-inflammatory.

The affect could be attributed to a variety of characteristics that nanocrystalline cellulose exhibits as a material. It holds a significant amount of water as its surface area to volume ratio is extremely high, resulting in proper hydration of the affected burn region. It is also a physical crystal that forms a layered lattice structure that is naturally resorbable.

The effect of measurable redness reduction could have also been to saturation of NCC in the skin tissue.

This result could theoretically be applied to any tissue, internal or external, and being that multiple variants of patches can be made from cellulose films all of the material is resorbable, meaning that the material can be safely introduced into any area in the body.

What is claimed is:

1. A composition, comprising:
   a. cannabidiol present at about 1% to about 55% by weight of the composition, wherein the cannabidiol is selected from the group consisting of cannabidiol-C5, cannabidiol momomethyl ether, cannabidiol-C4, cannabidivarin, cannabidiorcol, cannabidiolic acid, and cannabidivarinic acid;
   b. a polymeric nano article containing the cannabidiol wherein the particle at its largest dimension is smaller than 400 nanometers and greater than 0 nanometers, wherein the polymeric nanoparticle comprises a biodegradable polymer, wherein the polymeric nanoparticle is attached to a functional moiety, wherein the polymeric nanoparticle is present at 75% or less and greater than 1% by weight of the composition to alter a pharmacokinetic property of the cannabidiol, and wherein the biodegradable polymer is selected from the group consisting of polylactides, polyglycolides, poly(lactide-co-glycolide)s, polylactic acids, polyglycolic acids, poly(lactic acid-co-glycolic acid)s, copolymers of polylactides and poly(lactide-co-glycolide)s, poly(amino acids), polyacrylates polyketals, collagen, chitin, chitosan, dextran alginate, gelatin, albumin, ovalbumin, elastin, laminin, fibronectin, polymerized starches, chondroitin sulfate, polysucrose, hyaluronic acid, and heparin;

c. a vesicle for carrying the cannabidiol and the particle; and d. a substrate for delivering the cannabidiol and the particle in the vesicle, wherein the substrate is selected from the group consisting of a patch and a non-solid composition that is solidified when exposed to a suitable agent selected from the group consisting of light, heat, and a chemical activating agent.

2. The composition of claim 1, wherein the composition comprises cannabidiol present at approximately 15% to about 40% by weight of the total composition.

3. The composition of claim 1, wherein the cannabidiol is present at about 30% to about 40% by weight of the composition.

4. The composition of claim 1, wherein the cannabidiol is present at about 1% to about 10% by weight of the composition.

5. The composition of claim 1, wherein the polymeric nanoparticle comprises a nanocrystalline cellulose present at about 5% to about 40% by weight of the composition.

6. A composition, comprising:
a. cannabidiol present at about 1% to about 55% by weight of the composition, wherein the cannabidiol is selected from the group consisting of cannabidiol-C5, cannabidiol momomethyl ether, cannbidiol-C4, cannabidivarin, cannabidiorcol, cannabidiolic acid, and cannabidivarinic acid; and
b. a polymeric nanoparticle containing the cannabidiol, wherein the polymeric nanoparticles are present at about 75% or less and greater than 1% by weight of the composition, wherein the particles at their largest dimensions are smaller than 400 nanometers and greater than zero nanometers, and wherein the polymeric nanoparticles comprise a biodegradable polymer selected from the group consisting of polylactides, polyglycolides, poly(lactide-co-glycolide)s, polylactic acids, polyglycolic acids, poly(lactic acid-co-glycolic acid)s, copolymers of polylactides, and poly(lactide-co-glycolide)s, poly(amino acids) polyacrylates, polyketals, collagen, chitin, chitosan dextran, alginate gelatin, albumin, ovalbumin, elastin, laminin, fibronectin, polymerized starches, chondroitin sulfate, polysucrose, hyaluronic acid, and heparin; and
c. a substrate for delivering the cannabidiol and the particle, wherein the substrate is selected from the group consisting of a patch and a non-solid composition that is solidified when exposed to a suitable agent selected from the group consisting of light, heat, and a chemical activating agent.

7. The composition of claim 6, wherein the composition comprises about 15% to about 40% by weight of the cannabidiol.

8. The composition of claim 6, wherein the cannabidiol s present at about 30% to about 40% by weight of the composition.

9. The composition of claim 6, wherein the cannabidiol is present at about 10% by weight of the composition or less.

10. The composition of claim 6, wherein the polymeric nanoparticles are nanocrystalline cellulose recent at about 5 to about 40% by weight of the composition.

11. The composition of claim 6, further comprising a patch to deliver the composition to an affected area.

12. The composition of claim 6, further comprising a non-solid substrate that solidifies after administration when exposed to a suitable agent selected from the group consisting of a light, a temperature, and a chemical activating agent after administration.

13. The composition of claim 6, further comprising a vesicle to encapsulate the cannabidiol and polymeric nanoparticles to modify a property of the composition, the vesicle selected from the group consisting of liposomes, ethosomes, niosomes, and transferosomes.

14. The composition of claim 6, wherein the polymeric nanoparticle is attached to a moiety, wherein the moiety, comprises:
a. a sulfonate attached to the polymeric nanoparticle,
b. a spacer attached to the sulfonate, and
c. a functional group attached to the sulfonate via the spacer.

15. The composition of claim 14, wherein the polymeric nanoparticie further comprises a coating selected from the group consisting of albumin and silicone.

16. The composition of claim 1, further comprising a second biodegradable polymer selected from the group consisting of poloxamines, polyalkylene oxides, polyethylene oxides, and poly(propyl oxides).

17. The composition of claim 6, further comprising a second biodegradable polymer selected from the group consisting of poloxamines, polyalkylene oxides, polyethylene oxides, and poly(propylene oxides).

* * * * *